(12) United States Patent
Banner et al.

(10) Patent No.: US 7,964,594 B1
(45) Date of Patent: Jun. 21, 2011

(54) AMINO OXAZINE DERIVATIVES

(75) Inventors: David Banner, Basel (CH); Hans Hilpert, Muenchenstein (CH); Harald Mauser, Birsfelden (CH); Alexander V. Mayweg, Basel (CH); Mark Rogers-Evans, Bottmingen (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 12/958,436

(22) Filed: Dec. 2, 2010

(30) Foreign Application Priority Data

Dec. 10, 2009 (EP) .................................... 09178642

(51) Int. Cl.
*C07D 265/04* (2006.01)
*A61K 31/33* (2006.01)
(52) U.S. Cl. .................... 514/228.8; 544/88; 544/96
(58) Field of Classification Search ............ 544/88, 544/96; 514/228.8
See application file for complete search history.

(56) References Cited

U.S. PATENT DOCUMENTS

| 6,759,402 B2 * | 7/2004 | Macdonald et al. .......... 514/183 |
| 2007/0027199 A1 | 2/2007 | Malamas | |

FOREIGN PATENT DOCUMENTS

WO 2006/009653 1/2006

* cited by examiner

*Primary Examiner* — Kahsay T Habte
(74) *Attorney, Agent, or Firm* — George W. Johnston; Patricia S. Rocha-Tramaloni; Gene J. Yao

(57) ABSTRACT

This invention relates to 5,6-dihydro-4H-[1,3]oxazin-2-ylamine compounds of the formula

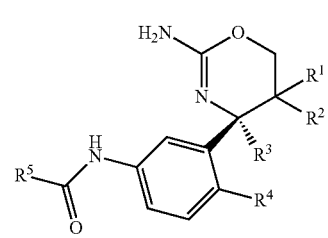

wherein $R^1$ to $R^5$ are as defined in the description and in the claims, as well as pharmaceutically acceptable salts thereof. These compounds are BACE2 inhibitors and can be used as medicaments for the treatment or prevention of diseases such as diabetes.

30 Claims, No Drawings

AMINO OXAZINE DERIVATIVES

PRIORITY TO RELATED APPLICATION(S)

This application claims the benefit of European Patent Application No. 09178642.6 filed Dec. 10, 2009, which is hereby incorporated by reference in its entirety.

FIELD OF THE INVENTION

The present invention relates to compounds useful in the treatment of type 2 diabetes and other metabolic disorders.

BACKGROUND

Type 2 diabetes (T2D) is caused by insulin resistance and inadequate insulin secretion from pancreatic beta-cells leading to poor blood-glucose control and hyperglycemia (M Prentki & C J Nolan, "Islet beta-cell failure in type 2 diabetes." J. Clin. Investig. 2006, 116(7), 1802-1812). Patients with T2D have an increased risk of microvascular and macrovascular disease and a range of related complications including diabetic nephropathy, retinopathy and cardiovascular disease. In 2000 an estimated 171 million people had the condition with the expectation that this figure will double by 2030 (S Wild, G Roglic, A Green, R. Sicree & H King, "Global prevalence of diabetes", Diabetes Care 2004, 27(5), 1047-1053) making the disease a major healthcare problem. The rise in prevalence of T2D is associated with an increasingly sedentary lifestyle and high-energy food intake of the world's population (P Zimmet, K G M M Alberti & J Shaw, "Global and societal implications of the diabetes epidemic" Nature 2001, 414, 782-787).

Beta-cell failure and consequent dramatic decline in insulin secretion and hyperglycemia marks the onset of T2D (M Prentki & C J Nolan, "Islet beta-cell failure in type 2 diabetes." J. Clin. Investig. 2006, 116(7), 1802-1812). Most current treatments do not prevent the loss of beta-cell mass characterising overt T2D. However, recent developments with GLP-1 analogues, gastrin and other agents show that preservation and proliferation of beta-cells is possible to achieve, leading to an improved glucose tolerance and slower progression to overt T2D (L L Baggio & D J Drucker, "Therapeutic approaches to preserve islet mass in type 2 diabetes", Annu Rev. Med. 2006, 57, 265-281).

Tmem27 has been identified as a protein promoting beta-cell proliferation (P Akpinar, S Kuwajima, J Krützfeldt, M Stoffel, "Tmem27: A cleaved and shed plasma membrane protein that stimulates pancreatic β cell proliferation", Cell Metab. 2005, 2, 385-397) and insulin secretion (K Fukui, Q Yang, Y Cao, N Takahashi et al., "The HNF-1 target Collectrin controls insulin exocytosis by SNARE complex formation", Cell Metab. 2005, 2, 373-384). Tmem27 is a 42 kDa membrane glycoprotein which is constitutively shed from the surface of beta-cells, resulting from a degradation of the full-length cellular Tmem27. Overexpression of Tmem27 in a transgenic mouse increases beta-cell mass and improves glucose tolerance in a DIO model of diabetes [K Fukui, Q Yang, Y Cao, N Takahashi et al., "The HNF-1 target Collectrin controls insulin exocytosis by SNARE complex formation", Cell Metab. 2005, 2, 373-384, P Akpinar, S Kuwajima, J Kriitzfeldt, M Stoffel, "Tmem27: A cleaved and shed plasma membrane protein that stimulates pancreatic β cell proliferation", Cell Metab. 2005, 2, 385-397). Furthermore, siRNA knockout of Tmem27 in a rodent beta-cell proliferation assay (eg using INS1e cells) reduces the proliferation rate, indicating a role for Tmem27 in control of beta-cell mass.

In vitro, BACE2 cleaves a peptide based on the sequence of Tmem27. The closely related protease BACE1 does not cleave this peptide and selective inhibition of BACE1 alone does not enhance proliferation of beta-cells. BACE1 (BACE for beta-site APP-cleaving enzyme, also known as beta-secretase) has been implicated in the pathogenesis of Alzheimer disease and in the formation of myelin sheaths in peripheral nerve cells.

The close homolog BACE2 is a membrane-bound aspartyl protease and is colocalised with Tmem27 in rodent pancreatic beta-cells (G Finzi, F Franzi, C Placidi, F Acquati et al., "BACE2 is stored in secretory granules of mouse and rat pancreatic beta cells", Ultrastruct Pathol. 2008, 32(6), 246-251). It is also known to be capable of degrading APP (I Hussain, D Powell, D Howlett, G Chapman et al., "ASP1 (BACE2) cleaves the amyloid precursor protein at the β-secretase site" Mol Cell Neurosci. 2000, 16, 609-619), IL-1R2 (P Kuhn, E Marjaux, A Imhof, B De Strooper et al., "Regulated intramembrane proteolysis of the interleukin-1 receptor II by alpha-, beta-, and gamma-secretase" J. Biol. Chem. 2007, 282(16), 11982-11995).

Inhibition of BACE2 is therefore proposed as a treatment for type 2 diabetes with the potential to preserve and restore beta-cell mass and stimulate insulin secretion in pre-diabetic and diabetic patients. It is therefore an object of the present invention to provide selective BACE2 inhibitors. Such compounds are useful as therapeutically active substances, particularly in the treatment and/or prevention of diseases which are associated with the inhibition of BACE2.

The compounds of the present invention exceed the compounds known in the art, inasmuch as they are strong and selective inhibitors of BACE2. They are expected to have an enhanced therapeutic potential compared to the compounds already known in the art and can be used for the treatment and prevention of diabetes, particularly type 2 diabetes, metabolic syndrome and a wide range of metabolic disorders.

SUMMARY

The present invention relates to compounds of formula I,

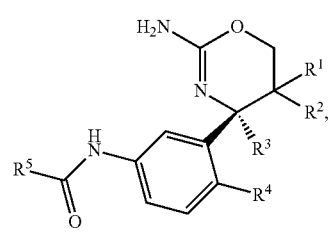

wherein
R¹ is hydrogen or $C_{1-7}$-alkyl;
R² is hydrogen or $C_{1-7}$-alkyl;
or R¹ and R² together with the C atom they are attached to form a $C_{3-7}$-cycloalkyl ring;
R³ is $C_{1-7}$-alkyl or $C_{3-7}$-cycloalkyl;
or R² and R³ together with the C atoms they are attached to form a $C_{3-7}$-cycloalkyl or a 3- to 7-membered O-heterocyclyl ring;
R⁴ is selected from the group consisting of hydrogen, $C_{1-7}$-alkyl, halogen, cyano and $C_{1-7}$-alkoxy; and $R^5$ is selected from the group consisting of:
  i) aryl, unsubstituted or substituted by one, two or three groups selected from the group consisting of $C_{1-7}$-alkyl, halogen, halogen-$C_{1-7}$-alkyl, $C_{1-7}$-alkoxy, halogen-$C_{1-7}$-alkoxy, cyano, hydroxy-$C_{1-7}$-alkyl, oxo and phenyl,
  ii) heteroaryl, unsubstituted or substituted by one, two or three groups selected from the group consisting of $C_{1-7}$-alkyl, halogen, halogen-$C_{1-7}$-alkyl, $C_{1-7}$-alkoxy, halogen-$C_{1-7}$-alkoxy, cyano, hydroxy-$C_{1-7}$-alkyl, oxo and phenyl,
  iii) $C_{1-7}$-alkyl, unsubstituted or substituted by one, two, three, four or five groups individually selected from the group consisting of halogen, halogen-$C_{1-7}$-alkyl, $C_{1-7}$-alkoxy, halogen-$C_{1-7}$-alkoxy, cyano and hydroxy-$C_{1-7}$-alkyl,
  iv) a $C_{3-7}$-cycloalkyl ring, unsubstituted or substituted by one, two or three groups selected from the group consisting of $C_{1-7}$-alkyl, halogen, halogen-$C_{1-7}$-alkyl, $C_{1-7}$-alkoxy, halogen-$C_{1-7}$-alkoxy, cyano and hydroxy-$C_{1-7}$-alkyl, and
  v) 3- to 7-membered O-heterocyclyl ring, unsubstituted or substituted by one, two or three groups selected from the group consisting of $C_{1-7}$-alkyl, halogen, halogen-$C_{1-7}$-alkyl, $C_{1-7}$-alkoxy, halogen-$C_{1-7}$-alkoxy, cyano and hydroxy-$C_{1-7}$-alkyl, or pharmaceutically acceptable salts thereof.

The invention is also concerned with the manufacture of compounds of formula I, with pharmaceutical compositions containing them and their use as medicaments. The compounds of formula I are inhibitors of BACE2 and may therefore be useful in the treatment of type 2 diabetes and other metabolic disorders.

DETAILED DESCRIPTION OF THE INVENTION

Unless otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described below.

All publications, patent applications, patents, and other references mentioned herein are incorporated by reference in their entirety.

The nomenclature used in this Application is based on IUPAC systematic nomenclature, unless indicated otherwise.

Unless otherwise indicated, the following definitions are set forth to illustrate and define the meaning and scope of the various terms used to describe the invention.

The term "compound(s) of this invention" and "compound(s) of the present invention" refers to compounds of formula I and stereoisomers, tautomers, solvates, and salts (e.g., pharmaceutically acceptable salts) thereof.

Structures depicted herein are also meant to include compounds that differ only in the presence of one or more isotopically enriched atoms. For example wherein one or more hydrogen atoms are replaced by deuterium, or one or more carbon atoms are replaced by a 13C- or 14C-enriched carbon are within the scope of this invention.

The term "halogen" refers to fluorine (fluoro, F), chlorine (chloro, Cl), bromine (bromo, Br) and iodine (iodo, I), with fluorine, chlorine and bromine being particular, and with fluorine and chlorine being more particular. Most particular is F.

The term "lower alkyl" or "$C_{1-7}$-alkyl", alone or in combination, signifies a straight-chain or branched-chain alkyl group with 1 to 7 carbon atoms, particularly a straight or branched-chain alkyl group with 1 to 6 carbon atoms and particularly particular a straight or branched-chain alkyl group with 1 to 4 carbon atoms. Examples of straight-chain and branched $C_{1-7}$ alkyl groups are methyl (Me), ethyl (Et), propyl, isopropyl, butyl, isobutyl, tert.-butyl, the isomeric pentyls, the isomeric hexyls and the isomeric heptyls, particularly methyl and ethyl and most particular methyl.

The term "lower alkoxy" or "$C_{1-7}$-alkoxy" refers to the group R'—O—, wherein R' is lower alkyl and the term "lower alkyl" has the previously given significance. Examples of lower alkoxy groups are methoxy (MeO, OMe), ethoxy, n-propoxy, isopropoxy, n-butoxy, isobutoxy, sec.-butoxy and tert.-butoxy, particularly methoxy and ethoxy.

The term "lower halogenalkyl" or "halogen-$C_{1-7}$-alkyl" refers to lower alkyl groups as defined above wherein at least one of the hydrogen atoms of the lower alkyl group is replaced by a halogen atom, particularly fluoro or chloro, most particularly fluoro. Among the particular lower halogenalkyl groups are trifluoromethyl, difluoromethyl, trifluoroethyl, 2,2-difluoroethyl, fluoromethyl and chloromethyl, with trifluoromethyl or difluoromethyl being especially particular.

The term "lower halogenalkoxy" or "halogen-$C_{1-7}$-alkoxy" refers to lower alkoxy groups as defined above wherein at least one of the hydrogen atoms of the lower alkoxy group is replaced by a halogen atom, particularly fluoro or chloro, most particularly fluoro. Among the particular halogenated lower alkoxy groups are trifluoromethoxy, difluoromethoxy, fluormethoxy and chloromethoxy, with trifluoromethoxy being especially particular.

The term "lower hydroxyalkyl" or "hydroxy-$C_{1-7}$-alkyl" refers to lower alkyl groups as defined above wherein at least one of the hydrogen atoms of the lower alkyl group is replaced by a hydroxy group. Among the particular lower hydroxyalkyl groups are hydroxymethyl or hydroxyethyl.

The term "oxo" means the group "=O" bound to a ring atom.

The term "cycloalkyl" or "$C_{3-7}$-cycloalkyl" denotes a saturated carbocyclic group containing from 3 to 7 carbon atoms, such as cyclopropyl, cyclobutyl, cyclopentyl, cyclohexyl or cycloheptyl. Especially particular are cyclopropyl, cyclobutyl and cyclopentyl. Specific is cyclopropyl.

The term "3- to 7-membered O-heterocyclyl ring" denotes a saturated 3- to 7-membered heterocyclyl ring containing at least one oxygen atom, such as oxirane, oxetane, tetrahydrofurane, tetrahydropurane and oxepane. A tetrahydrofurane (furyl) ring is particular. Specific is oxetanyl.

The term "aryl" refers to an aromatic monocyclic or multicyclic ring system having 6 to 14 carbon atoms, particularly 6 to 10 carbon atoms. Particular aryl groups are phenyl and naphthyl, with phenyl being most particular.

The term "heteroaryl" refers to an aromatic or partly unsaturated 5- or 6-membered ring which comprises at least one heteroatom selected from nitrogen, oxygen and/or sulphur, and can in addition comprise one or three atoms selected from nitrogen, oxygen and/or sulphur, such as pyridyl, pyrazinyl, pyrimidinyl, pyridazinyl, 6-oxo-1,6-dihydropyridazinyl, 5-oxo-4,5-dihydropyrazinyl, pyrrolyl, furyl, thienyl, oxazolyl, isoxazolyl, oxadiazolyl, thiadiazolyl, tetrazolyl, pyrazolyl, imidazolyl, triazolyl and thiazolyl. The term "heteroaryl" further refers to bicyclic aromatic or partly unsaturated groups comprising two 5- or 6-membered rings, in which one or both rings can contain one, two or three atoms selected from nitrogen, oxygen or sulphur, such as quinolinyl, isoquinolinyl, cinnolinyl, pyrazolo[1,5-a]pyridyl, imidazo[1,2-a]pyridyl, thieno[2,3-c]pyridyl, quinoxalinyl, benzo[b]thienyl, benzothiazolyl, benzotriazolyl, indolyl, indazolyl and 3,4-dihydro-1H-isoquinolinyl. Particular heteroaryl groups are thienyl, oxazolyl, isoxazolyl, pyrazolyl, pyridyl, pyrimidinyl, pyrazinyl, 6-oxo-1,6-dihydropyridazinyl, 5-oxo-4,5-dihydropyrazinyl and imidazo[1,2-a]pyridyl, with thienyl, oxazolyl, pyrazolyl, pyridyl, pyrimidinyl and pyrazinyl being more particular and pyridyl being most particular. Specific are 1H-pyrazolyl, benzo[b]thiophenyl, isoxazolyl, oxazolyl, pyrazinyl, pyridinyl, pyrimidinyl, thiazolyl, thieno[2,3-c]pyridinyl and thiophenyl, more specific are 1H-pyrazole-3-yl, benzo[b]thiophene-2-yl, isoxazole-3-yl, oxazole-4-yl, pyrazine-2-yl, pyridine-2-yl, pyrimidine-2-yl, thiazol-4-yl, thieno[2,3-c]pyridine-7-yl and thiophene-2-yl.

Compounds of formula I can form pharmaceutically acceptable salts. The term "pharmaceutically acceptable salts" refers to those salts which retain the biological effectiveness and properties of the free bases or free acids, which are not biologically or otherwise undesirable. Particularly, the pharmaceutically acceptable salts of the compounds of formula I are the acid addition salts with physiologically compatible mineral acids, such as hydrochloric acid, sulfuric acid, sulfurous acid or phosphoric acid; or with organic acids, such as methanesulfonic acid, ethanesulfonic acid, p-toluenesulfonic acid, formic acid, acetic acid, propionic acid, glycolic acid, pyruvic acid, oxylic acid, lactic acid, trifluoroacetic acid, citric acid, fumaric acid, maleic acid, malonic acid, tartaric acid, benzoic acid, cinnamic acid, mandelic acid, succinic acid or salicylic acid. Particularly particular pharmaceutically acceptable salts of compounds of formula I are the acid addition salts such as the hydrochloride salts, the formate salts or trifluoroacetate salts.

The compounds of formula I can also be solvated, e.g., hydrated. The solvation can be effected in the course of the manufacturing process or can take place e.g. as a consequence of hygroscopic properties of an initially anhydrous compound of formula I (hydration). The term "pharmaceutically acceptable salts" also includes physiologically acceptable solvates.

"Isomers" are compounds that have identical molecular formulae but that differ in the nature or the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images are termed "enantiomers", or sometimes optical isomers. A carbon atom bonded to four non-identical substituents is termed a "chiral center". The term "chiral" denotes the ability of non-superimposability with the mirror image, while the term "achiral" refers to embodiments which are superimposable with their mirror image. Chiral molecules are optically active, i.e., they have the ability to rotate the plane of plane-polarized light. Compounds of present invention can have one or more chiral centers and can exist in the form of optically pure enantiomers, mixtures of enantiomers such as, for example, racemates, optically pure diastereoisomers, mixtures of diastereoisomers, diastereoisomeric racemates or mixtures of diastereoisomeric racemates. Whenever a chiral center is present in a chemical structure, it is intended that all stereoisomers associated with that chiral center are encompassed by the present invention.

In detail, the invention relates to compounds of formula I,

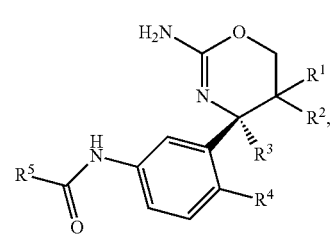

wherein
$R^1$ is hydrogen or $C_{1-7}$-alkyl;
$R^2$ is hydrogen or $C_{1-7}$-alkyl;
or $R^1$ and $R^2$ together with the C atom they are attached to form a $C_{3-7}$-cycloalkyl ring;
$R^3$ is $C_{1-7}$-alkyl or $C_{3-7}$-cycloalkyl;
or $R^2$ and $R^3$ together with the C atoms they are attached to form a $C_{3-7}$-cycloalkyl or a 3- to 7-membered O-heterocyclyl ring;
$R^4$ is selected from the group consisting of hydrogen, $C_{1-7}$-alkyl, halogen, cyano and $C_{1-7}$-alkoxy; and
$R^5$ is selected from the group consisting of:
  i) aryl, unsubstituted or substituted by one, two or three groups selected from the group consisting of $C_{1-7}$-alkyl, halogen, halogen-$C_{1-7}$-alkyl, $C_{1-7}$-alkoxy, halogen-$C_{1-7}$-alkoxy, cyano, hydroxy-$C_{1-7}$-alkyl, oxo and phenyl,
  ii) heteroaryl, unsubstituted or substituted by one, two or three groups selected from the group consisting of $C_{1-7}$-alkyl, halogen, halogen-$C_{1-7}$-alkyl, $C_{1-7}$-alkoxy, halogen-$C_{1-7}$-alkoxy, cyano, hydroxy-$C_{1-7}$-alkyl, oxo and phenyl,
  iii) $C_{1-7}$-alkyl, unsubstituted or substituted by one, two, three, four or five groups individually selected from the group consisting of halogen, halogen-$C_{1-7}$-alkyl, $C_{1-7}$-alkoxy, halogen-$C_{1-7}$-alkoxy, cyano and hydroxy-$C_{1-7}$-alkyl,
  iv) a $C_{3-7}$-cycloalkyl ring, unsubstituted or substituted by one, two or three groups selected from the group consisting of $C_{1-7}$-alkyl, halogen, halogen-$C_{1-7}$-alkyl, $C_{1-7}$-alkoxy, halogen-$C_{1-7}$-alkoxy, cyano and hydroxy-$C_{1-7}$-alkyl, and
  v) 3- to 7-membered O-heterocyclyl ring, unsubstituted or substituted by one, two or three groups selected from the group consisting of $C_{1-7}$-alkyl, halogen, halogen-$C_{1-7}$-alkyl, $C_{1-7}$-alkoxy, halogen-$C_{1-7}$-alkoxy, cyano and hydroxy-$C_{1-7}$-alkyl,
or pharmaceutically acceptable salts thereof.

In a particular embodiment, the invention relates to compounds of formula I, wherein
$R^1$ is hydrogen or $C_{1-7}$-alkyl;
$R^2$ is hydrogen or $C_{1-7}$-alkyl;
or $R^1$ and $R^2$ together with the C atom they are attached to form a $C_{3-7}$-cycloalkyl ring;
$R^3$ is $C_{1-7}$-alkyl or $C_{3-7}$-cycloalkyl;
or $R^2$ and $R^3$ together with the C atoms they are attached to form a $C_{3-7}$-cycloalkyl or a 3- to 7-membered O-heterocyclyl ring;
$R^4$ is selected from the group consisting of hydrogen, $C_{1-7}$-alkyl, halogen, cyano and $C_{1-7}$-alkoxy; and
$R^5$ is aryl or heteroaryl, said aryl or heteroaryl being unsubstituted or substituted by one, two or three groups selected from the group consisting of $C_{1-7}$-alkyl, halogen, halogen- $C_{1-7}$-alkyl, $C_{1-7}$-alkoxy, halogen-$C_{1-7}$-alkoxy, cyano, hydroxy-$C_{1-7}$-alkyl, oxo and phenyl;

or pharmaceutically acceptable salts thereof.

In a particular embodiment, the invention relates to compounds of formula I, wherein $R^1$ is hydrogen;

$R^2$ is hydrogen;

$R^3$ is $C_{1-7}$-alkyl;

$R^4$ is halogen; and $R^5$ is selected from the group consisting of 1H-pyrazolyl, benzo[b]thiophenyl, isoxazolyl, oxazolyl, pyrazinyl, pyridinyl, pyrimidinyl, thiazolyl, thieno[2,3-c]pyridinyl, thiophenyl, phenyl, ethyl, cyclopropyl and oxetanyl being unsubstituted or substituted as defined herein;

or pharmaceutically acceptable salts thereof.

In a particular embodiment, the invention relates to compounds of formula I as herein described, wherein $R^1$ and $R^2$ together with the C atom they are attached to form a $C_{3-7}$-cycloalkyl ring.

In a particular embodiment, the invention relates to compounds of formula I as herein described, wherein $R^2$ and $R^3$ together with the C atom they are attached to form a $C_{3-7}$-cycloalkyl ring.

In a particular embodiment, the invention relates to compounds of formula I as herein described, wherein $R^2$ and $R^3$ together with the C atom they are attached to form furyl.

In a particular embodiment, the invention relates to compounds of formula I as herein described, wherein $R^1$ and $R^2$ together with the C atom they are attached to form a cyclopropyl.

In a particular embodiment, the invention relates to compounds of formula I as herein described, wherein $R^1$ and $R^2$ are each hydrogen.

In a particular embodiment, the invention relates to compounds of formula I as herein described, wherein $R^1$ is hydrogen.

In a particular embodiment, the invention relates to compounds of formula I as herein described, wherein $R^2$ is hydrogen.

In a particular embodiment, the invention relates to compounds of formula I as herein described, wherein $R^3$ is $C_{1-7}$-alkyl.

In a particular embodiment, the invention relates to compounds of formula I as herein described, wherein $R^3$ is methyl.

In a particular embodiment, the invention relates to compounds of formula I as herein described, wherein $R^3$ is ethyl.

In a particular embodiment, the invention relates to compounds of formula I as herein described, wherein $R^4$ is hydrogen or halogen.

In a particular embodiment, the invention relates to compounds of formula I as herein described, wherein $R^4$ is halogen.

In a particular embodiment, the invention relates to compounds of formula I as herein described, wherein $R^4$ is fluoro.

In a particular embodiment, the invention relates to compounds of formula I as herein described, wherein $R^5$ is heteroaryl, said heteroaryl being unsubstituted or substituted by one, two or three groups selected from the group consisting of $C_{1-7}$-alkyl, halogen, halogen-$C_{1-7}$-alkyl, $C_{1-7}$-alkoxy, halogen-$C_{1-7}$-alkoxy, cyano, hydroxy-$C_{1-7}$-alkyl, oxo and phenyl.

In a particular embodiment, the invention relates to compounds of formula I as herein described, wherein $R^5$ is heteroaryl selected from the group consisting of pyridyl, pyrazinyl, pyrimidinyl, pyridazinyl, 6-oxo-1,6-dihydropyridazinyl, 5-oxo-4,5-dihydropyrazinyl, pyrrolyl, furyl, thienyl, oxazolyl, isoxazolyl, oxadiazolyl, thiadiazolyl, tetrazolyl, pyrazolyl, imidazolyl, triazolyl, thiazolyl, quinolinyl, isoquinolinyl, cinnolinyl, pyrazolo[1,5-a]pyridyl, imidazo[1,2-a]pyridyl, thieno[2,3-c]pyridyl, quinoxalinyl, benzo[b]thienyl, benzothiazolyl, benzotriazolyl, indolyl, indazolyl and 3,4-dihydro-1H-isoquinolinyl, said heteroaryl being unsubstituted or substituted by one, two or three groups selected from the group consisting of $C_{1-7}$-alkyl, halogen, halogen-$C_{1-7}$-alkyl, $C_{1-7}$-alkoxy, halogen-$C_{1-7}$-alkoxy, cyano, hydroxy-$C_{1-7}$-alkyl, oxo and phenyl.

In a particular embodiment, the invention relates to compounds of formula I as herein described, wherein $R^5$ is heteroaryl selected from the group consisting of thienyl, oxazolyl, isoxazolyl, pyrazolyl, pyridyl, pyrimidinyl, pyrazinyl, 6-oxo-1,6-dihydropyridazinyl, 5-oxo-4,5-dihydropyrazinyl and imidazo[1,2-a]pyridyl, said heteroaryl being unsubstituted or substituted by one, two or three groups selected from the group consisting of $C_{1-7}$-alkyl, halogen, halogen-$C_{1-7}$-alkyl, $C_{1-7}$-alkoxy, halogen-$C_{1-7}$-alkoxy, cyano, hydroxy-$C_{1-7}$-alkyl, oxo and phenyl.

In a particular embodiment, the invention relates to compounds of formula I as herein described, wherein $R^5$ is heteroaryl selected from the group consisting of thienyl, oxazolyl, pyridyl, pyrimidinyl and pyrazinyl, said heteroaryl being unsubstituted or substituted by one, two or three groups selected from the group consisting of $C_{1-7}$-alkyl, halogen, halogen-$C_{1-7}$-alkyl, $C_{1-7}$-alkoxy, halogen-$C_{1-7}$-alkoxy, cyano, hydroxy-$C_{1-7}$-alkyl, oxo and phenyl.

In a particular embodiment, the invention relates to compounds of formula I as herein described, wherein $R^5$ is heteroaryl selected from the group consisting of thienyl, oxazolyl, pyridyl, pyrimidinyl and pyrazinyl substituted by one, two or three groups selected from the group consisting of $C_{1-7}$-alkyl, halogen, halogen-$C_{1-7}$-alkyl, $C_{1-7}$-alkoxy, halogen-$C_{1-7}$-alkoxy, cyano, hydroxy-$C_{1-7}$-alkyl, oxo and phenyl.

In a particular embodiment, the invention relates to compounds of formula I as herein described, wherein $R^5$ is heteroaryl selected from the group consisting of 1H-pyrazolyl, benzo[b]thiophenyl, isoxazolyl, oxazolyl, pyrazinyl, pyridinyl, pyrimidinyl, thiazolyl, thieno[2,3-c]pyridinyl and thiophenyl, said heteroaryl being unsubstituted or substituted by one or two groups selected from the group consisting of $C_{1-7}$-alkyl, halogen, halogen-$C_{1-7}$-alkoxy, halogen-$C_{1-7}$-alkyl, $C_{1-7}$-alkoxy, cyano and phenyl.

In a particular embodiment, the invention relates to compounds of formula I as herein described, wherein $R^5$ is heteroaryl selected from the group consisting of 1H-pyrazolyl, thiazolyl, oxazolyl, pyridinyl, substituted by one or two substituents selected from the group consisting of $C_{1-7}$-alkyl, halogen and cyano.

In a particular embodiment, the invention relates to compounds of formula I as herein described, wherein $R^5$ is 1H-pyrazolyl.

In a particular embodiment, the invention relates to compounds of formula I as herein described, wherein $R^5$ is thiazolyl.

In a particular embodiment, the invention relates to compounds of formula I as herein described, wherein $R^5$ is oxazolyl.

In a particular embodiment, the invention relates to compounds of formula I as herein described, wherein $R^5$ is pyridinyl.

In a particular embodiment, the invention relates to compounds of formula I as herein described, wherein $R^5$ is heteroaryl selected from the group consisting of 1H-pyrazole-3-yl, benzo[b]thiophene-2-yl, isoxazole-3-yl, oxazole-4-yl, pyrazine-2-yl, pyridine-2-yl, pyrimidine-2-yl, thiazol-4-yl, thieno[2,3-c]pyridine-7-yl and thiophene-2-yl, said heteroaryl being unsubstituted or substituted by one or two groups selected from the group consisting of methyl, fluoro, chloro, difluoromethoxy, trifluoroethoxy, trifluoromethyl, methoxy, cyano and phenyl.

In a particular embodiment, the invention relates to compounds of formula I as herein described, wherein $R^5$ is phenyl, said phenyl being unsubstituted or substituted by one, two or three groups selected from the group consisting of $C_{1-7}$-alkyl, halogen, halogen-$C_{1-7}$-alkyl, $C_{1-7}$-alkoxy, halogen-$C_{1-7}$-alkoxy, cyano, hydroxy-$C_{1-7}$-alkyl, oxo and phenyl.

In a particular embodiment, the invention relates to compounds of formula I as herein described, wherein $R^5$ is phenyl, substituted by one or two halogens.

In a particular embodiment, the invention relates to compounds of formula I as herein described, wherein $R^5$ is $C_{1-7}$-alkyl, unsubstituted or substituted by one, two, three, four or five halogens.

In a particular embodiment, the invention relates to compounds of formula I as herein described, wherein $R^5$ is ethyl, substituted by one, two, three, four or five fluoros.

In a particular embodiment, the invention relates to compounds of formula I as herein described, wherein $R^5$ is $C_{3-7}$-cycloalkyl ring, unsubstituted or substituted by one, two or three groups selected from the group consisting of halogen and halogen-$C_{1-7}$-alkyl.

In a particular embodiment, the invention relates to compounds of formula I as herein described, wherein $R^5$ is cyclopropyl, by one or two groups selected from the group consisting of fluoro and trifluoromethyl.

In a particular embodiment, the invention relates to compounds of formula I as herein described, wherein $R^5$ is 3- to 7-membered O-heterocyclyl ring, unsubstituted or substituted by one, two or three groups selected from the group consisting of $C_{1-7}$-alkyl, halogen, halogen-$C_{1-7}$-alkyl, $C_{1-7}$-alkoxy, halogen-$C_{1-7}$-alkoxy, cyano and hydroxy-$C_{1-7}$-alkyl.

In a particular embodiment, the invention relates to compounds of formula I as herein described, wherein $R^5$ is oxetanyl, substituted by methyl.

In a particular embodiment, the invention relates to compounds of formula I as herein described, selected from the group consisting of 3,5-Dichloro-pyridine-2-carboxylic acid [3-((S)-2-amino-4-methyl-5,6-dihydro-4H-[1,3]oxazin-4-yl)-4-fluoro-phenyl]-amide, 5-Chloro-pyridine-2-carboxylic acid [3-((S)-2-amino-4-methyl-5,6-dihydro-4H-[1,3]oxazin-4-yl)-4-fluoro-phenyl]-amide, 5-Fluoro-pyridine-2-carboxylic acid [3-((S)-2-amino-4-methyl-5,6-dihydro-4H-[1,3]oxazin-4-yl)-4-fluoro-phenyl]-amide, Pyridine-2-carboxylic acid [3-((S)-2-amino-4-methyl-5,6-dihydro-4H-[1,3]oxazin-4-yl)-4-fluoro-phenyl]-amide, 5-Trifluoromethyl-pyridine-2-carboxylic acid [3-((S)-2-amino-4-methyl-5,6-dihydro-4H-[1,3]oxazin-4-yl)-4-fluoro-phenyl]-amide, 3-Fluoro-pyridine-2-carboxylic acid [3-((S)-2-amino-4-methyl-5,6-dihydro-4H-[1,3]oxazin-4-yl)-4-fluoro-phenyl]-amide, 5-Fluoro-thiophene-2-carboxylic acid [3-((S)-2-amino-4-methyl-5,6-dihydro-4H-[1,3]oxazin-4-yl)-4-fluoro-phenyl]-amide, 2-Methyl-oxazole-4-carboxylic acid [3-((S)-2-amino-4-methyl-5,6-dihydro-4H-[1,3]oxazin-4-yl)-4-fluoro-phenyl]-amide, 4-Chloro-pyridine-2-carboxylic acid [3-((S)-2-amino-4-methyl-5,6-dihydro-4H-[1,3]oxazin-4-yl)-4-fluoro-phenyl]-amide, 5-Chloro-thiophene-2-carboxylic acid [3-((S)-2-amino-4-methyl-5,6-dihydro-4H-[1,3]oxazin-4-yl)-4-fluoro-phenyl]-amide, Thieno[2,3-c]pyridine-7-carboxylic acid [3-((S)-2-amino-4-methyl-5,6-dihydro-4H-[1,3]oxazin-4-yl)-4-fluoro-phenyl]-amide, 3-Phenyl-pyridine-2-carboxylic acid [3-((S)-2-amino-4-methyl-5,6-dihydro-4H-[1,3]oxazin-4-yl)-4-fluoro-phenyl]-amide, Benzo[b]thiophene-2-carboxylic acid [3-((S)-2-amino-4-methyl-5,6-dihydro-4H-[1,3]oxazin-4-yl)-4-fluoro-phenyl]-amide, 5-Chloro-pyrazine-2-carboxylic acid [3-((S)-2-amino-4-methyl-5,6-dihydro-4H-[1,3]oxazin-4-yl)-4-fluoro-phenyl]-amide, 5-Methyl-pyridine-2-carboxylic acid [3-((S)-2-amino-4-methyl-5,6-dihydro-4H-[1,3]oxazin-4-yl)-4-fluoro-phenyl]-amide, 3-Trifluoromethyl-pyridine-2-carboxylic acid [3-((S)-2-amino-4-methyl-5,6-dihydro-4H-[1,3]oxazin-4-yl)-4-fluoro-phenyl]-amide, 5-Methyl-thiophene-2-carboxylic acid [3-((S)-2-amino-4-methyl-5,6-dihydro-4H-[1,3]oxazin-4-yl)-4-fluoro-phenyl]-amide, Pyridine-2-carboxylic acid [3-((S)-2-amino-4-ethyl-5,6-dihydro-4H-[1,3]oxazin-4-yl)-4-fluoro-phenyl]-amide, 5-Chloro-pyridine-2-carboxylic acid [3-((S)-2-amino-4-ethyl-5,6-dihydro-4H-[1,3]oxazin-4-yl)-4-fluoro-phenyl]-amide, 5-Methyl-thiophene-2-carboxylic acid [3-((S)-2-amino-4-ethyl-5,6-dihydro-4H-[1,3]oxazin-4-yl)-4-fluoro-phenyl]-amide, 5-Chloro-thiophene-2-carboxylic acid [3-((S)-2-amino-4-ethyl-5,6-dihydro-4H-[1,3]oxazin-4-yl)-4-fluoro-phenyl]-amide, 3,5-Dichloro-pyridine-2-carboxylic acid [3-((S)-2-amino-4-ethyl-5,6-dihydro-4H-[1,3]oxazin-4-yl)-4-fluoro-phenyl]-amide, 5-Chloro-3-methyl-pyridine-2-carboxylic acid [3-((S)-2-amino-4-ethyl-5,6-dihydro-4H-[1,3]oxazin-4-yl)-4-fluoro-phenyl]-amide, 2-Methyl-oxazole-4-carboxylic acid [3-((S)-2-amino-4-ethyl-5,6-dihydro-4H-[1,3]oxazin-4-yl)-4-fluoro-phenyl]-amide, 5-Cyano-pyridine-2-carboxylic acid [3-((S)-2-amino-4-methyl-5,6-dihydro-4H-[1,3]oxazin-4-yl)-4-fluoro-phenyl]-amide, 5-Chloro-3-methyl-pyridine-2-carboxylic acid [3-((S)-2-amino-4-methyl-5,6-dihydro-4H-[1,3]oxazin-4-yl)-4-fluoro-phenyl]-amide, 3-Methoxy-pyridine-2-carboxylic acid [3-((S)-2-amino-4-methyl-5,6-dihydro-4H-[1,3]oxazin-4-yl)-4-fluoro-phenyl]-amide, 2-Methyl-thiazole-4-carboxylic acid [3-((S)-2-amino-4-methyl-5,6-dihydro-4H-[1,3]oxazin-4-yl)-4-fluoro-phenyl]-amide, 1-Methyl-1H-pyrazole-3-carboxylic acid [3-((S)-2-amino-4-methyl-5,6-dihydro-4H-[1,3]oxazin-4-yl)-4-fluoro-phenyl]-amide, 5-Methoxy-pyridine-2-carboxylic acid [3-((S)-2-amino-4-methyl-5,6-dihydro-4H-[1,3]oxazin-4-yl)-4-fluoro-phenyl]-amide, 3-Chloro-5-trifluoromethyl-pyridine-2-carboxylic acid [3-((S)-2-amino-4-methyl-5,6-dihydro-4H-[1,3]oxazin-4-yl)-4-fluoro-phenyl]-amide, 6-Chloro-pyridine-2-carboxylic acid [3-((S)-2-amino-4-methyl-5,6-dihydro-4H-[1,3]oxazin-4-yl)-4-fluoro-phenyl]-amide,
3,5-Difluoro-pyridine-2-carboxylic acid [3-((S)-2-amino-4-methyl-5,6-dihydro-4H-[1,3]oxazin-4-yl)-4-fluoro-phenyl]-amide,
3-Methyl-thiophene-2-carboxylic acid [3-((S)-2-amino-4-methyl-5,6-dihydro-4H-[1,3]oxazin-4-yl)-4-fluoro-phenyl]-amide,
3-Chloro-5-fluoro-pyridine-2-carboxylic acid [3-((S)-2-amino-4-methyl-5,6-dihydro-4H-[1,3]oxazin-4-yl)-4-fluoro-phenyl]-amide,
5-Chloro-pyridine-2-carboxylic acid [3-((S)-6-amino-8-methyl-5-oxa-7-aza-spiro[2.5]oct-6-en-8-yl)-4-fluoro-phenyl]-amide,
3-Fluoro-pyridine-2-carboxylic acid [3-((S)-6-amino-8-methyl-5-oxa-7-aza-spiro[2.5]oct-6-en-8-yl)-4-fluoro-phenyl]-amide,
5-Chloro-3-methyl-pyridine-2-carboxylic acid [3-((S)-6-amino-8-methyl-5-oxa-7-aza-spiro[2.5]oct-6-en-8-yl)-4-fluoro-phenyl]-amide,
5-Methoxy-pyridine-2-carboxylic acid [3-((S)-6-amino-8-methyl-5-oxa-7-aza-spiro[2.5]oct-6-en-8-O-4-fluoro-phenyl]-amide,
5-Fluoro-pyridine-2-carboxylic acid [3-((S)-6-amino-8-methyl-5-oxa-7-aza-spiro[2.5]oct-6-en-8-yl)-4-fluoro-phenyl]-amide,
5-Cyano-pyridine-2-carboxylic acid [3-((S)-6-amino-8-methyl-5-oxa-7-aza-spiro[2.5]oct-6-en-8-yl)-4-fluoro-phenyl]-amide,
5-Difluoromethoxy-pyridine-2-carboxylic acid [3-((S)-6-amino-8-methyl-5-oxa-7-aza-spiro[2.5]oct-6-en-8-yl)-4-fluoro-phenyl]-amide,
Pyridine-2-carboxylic acid [3-((S)-6-amino-8-methyl-5-oxa-7-aza-spiro[2.5]oct-6-en-8-yl)-4-fluoro-phenyl]-amide,
5-Chloro-pyrimidine-2-carboxylic acid [3-((S)-6-amino-8-methyl-5-oxa-7-aza-spiro[2.5]oct-6-en-8-O-4-fluoro-phenyl]-amide,
N-[3-((S)-2-Amino-4-methyl-5,6-dihydro-4H-[1,3]oxazin-4-yl)-4-fluoro-phenyl]-2,3,3,3-tetrafluoro-propionamide,
2,2-Difluoro-cyclopropanecarboxylic acid [3-((S)-2-amino-4-methyl-5,6-dihydro-4H-[1,3]oxazin-4-yl)-4-fluoro-phenyl]-amide,
(S)—N-(3-(6-amino-8-methyl-5-oxa-7-azaspiro[2.5]oct-6-en-8-yl)-4-fluorophenyl)-2,6-difluorobenzamide,
(S)—N-(3-(6-amino-8-methyl-5-oxa-7-azaspiro[2.5]oct-6-en-8-yl)-4-fluorophenyl)-3-chloropicolinamide,
(S)—N-(3-(6-amino-8-methyl-5-oxa-7-azaspiro[2.5]oct-6-en-8-yl)-4-fluorophenyl)-3,5-difluoropicolinamide,
(S)—N-(3-(6-amino-8-methyl-5-oxa-7-azaspiro[2.5]oct-6-en-8-yl)-4-fluorophenyl)-3-chloro-5-(trifluoromethyl)picolinamide,
(S)—N-(3-(6-amino-8-methyl-5-oxa-7-azaspiro[2.5]oct-6-en-8-yl)-4-fluorophenyl)-3-(trifluoromethyl)picolinamide,
(S)—N-(3-(6-amino-8-methyl-5-oxa-7-azaspiro[2.5]oct-6-en-8-yl)-4-fluorophenyl)-3-chloro-5-fluoropicolinamide,
(S)—N-(3-(6-amino-8-methyl-5-oxa-7-azaspiro[2.5]oct-6-en-8-yl)-4-fluorophenyl)-3,5-dichloropicolinamide,
(S)—N-(3-(6-amino-8-methyl-5-oxa-7-azaspiro[2.5]oct-6-en-8-yl)-4-fluorophenyl)-1-(trifluoromethyl)cyclopropanecarboxamide,
N-(3-((S)-6-amino-8-methyl-5-oxa-7-azaspiro[2.5]oct-6-en-8-yl)-4-fluorophenyl)-2,2-difluorocyclopropanecarboxamide,
(S)—N-(3-(6-amino-8-methyl-5-oxa-7-azaspiro[2.5]oct-6-en-8-yl)-4-fluorophenyl)-4-chloro-1-methyl-1H-pyrazole-3-carboxamide,
(S)—N-(3-(6-amino-8-methyl-5-oxa-7-azaspiro[2.5]oct-6-en-8-yl)-4-fluorophenyl)-5-chloro-4-methylisoxazole-3-carboxamide,
1-Trifluoromethyl-cyclopropanecarboxylic acid [3-((S)-2-amino-4-methyl-5,6-dihydro-4H-[1,3]oxazin-4-yl)-4-fluoro-phenyl]-amide,
N-[3-((S)-2-Amino-4-methyl-5,6-dihydro-4H-[1,3]oxazin-4-yl)-4-fluoro-phenyl]-3,3,3-trifluoro-propionamide,
(S)—N-(3-(2-amino-4-methyl-5,6-dihydro-4H-1,3-oxazin-4-yl)-4-fluorophenyl)-3-(2,2,2-trifluoroethoxy)picolinamide,
5-Difluoromethoxy-pyridine-2-carboxylic acid [3-((S)-2-amino-4-methyl-5,6-dihydro-4H-[1,3]oxazin-4-yl)-4-fluoro-phenyl]-amide,
(S)—N-(3-(2-amino-4-methyl-5,6-dihydro-4H-1,3-oxazin-4-yl)-4-fluorophenyl)-3-methyloxetane-3-carboxamide,
(S)—N-(3-(2-amino-4-methyl-5,6-dihydro-4H-1,3-oxazin-4-yl)-4-fluorophenyl)-4-methylisoxazole-3-carboxamide,
4-Chloro-1H-pyrazole-3-carboxylic acid [3-((S)-2-amino-4-methyl-5,6-dihydro-4H-[1,3]oxazin-4-yl)-4-fluoro-phenyl]-amide, and
5-Chloro-pyridine-2-carboxylic acid [3-((4aS,7aS)-2-amino-4a,5-dihydro-4H-furo[3,4-d][1,3]oxazin-7a-yl)-4-fluoro-phenyl]-amide,
or pharmaceutically acceptable salts thereof.

In a particular embodiment, the invention relates to compounds of formula I as herein described, selected from the group consisting of
3,5-Dichloro-pyridine-2-carboxylic acid [3-((S)-2-amino-4-methyl-5,6-dihydro-4H-[1,3]oxazin-4-yl)-4-fluoro-phenyl]-amide,
5-Chloro-pyridine-2-carboxylic acid [3-((S)-2-amino-4-methyl-5,6-dihydro-4H-[1,3]oxazin-4-yl)-4-fluoro-phenyl]-amide,
5-Fluoro-pyridine-2-carboxylic acid [3-((S)-2-amino-4-methyl-5,6-dihydro-4H-[1,3]oxazin-4-yl)-4-fluoro-phenyl]-amide,
Pyridine-2-carboxylic acid [3-((S)-2-amino-4-methyl-5,6-dihydro-4H-[1,3]oxazin-4-yl)-4-fluoro-phenyl]-amide,
5-Trifluoromethyl-pyridine-2-carboxylic acid [3-((S)-2-amino-4-methyl-5,6-dihydro-4H-[1,3]oxazin-4-yl)-4-fluoro-phenyl]-amide,
3-Fluoro-pyridine-2-carboxylic acid [3-((S)-2-amino-4-methyl-5,6-dihydro-4H-[1,3]oxazin-4-yl)-4-fluoro-phenyl]-amide,
5-Fluoro-thiophene-2-carboxylic acid [3-((S)-2-amino-4-methyl-5,6-dihydro-4H-[1,3]oxazin-4-yl)-4-fluoro-phenyl]-amide,
2-Methyl-oxazole-4-carboxylic acid [3-((S)-2-amino-4-methyl-5,6-dihydro-4H-[1,3]oxazin-4-yl)-4-fluoro-phenyl]-amide,
4-Chloro-pyridine-2-carboxylic acid [3-((S)-2-amino-4-methyl-5,6-dihydro-4H-[1,3]oxazin-4-yl)-4-fluoro-phenyl]-amide,
5-Chloro-thiophene-2-carboxylic acid [3-((S)-2-amino-4-methyl-5,6-dihydro-4H-[1,3]oxazin-4-yl)-4-fluoro-phenyl]-amide,
Thieno[2,3-c]pyridine-7-carboxylic acid [3-((S)-2-amino-4-methyl-5,6-dihydro-4H-[1,3]oxazin-4-yl)-4-fluoro-phenyl]-amide,
3-Phenyl-pyridine-2-carboxylic acid [3-((S)-2-amino-4-methyl-5,6-dihydro-4H-[1,3]oxazin-4-yl)-4-fluoro-phenyl]-amide, Benzo[b]thiophene-2-carboxylic acid [3-((S)-2-amino-4-methyl-5,6-dihydro-4H-[1,3]oxazin-4-yl)-4-fluoro-phenyl]-amide,
5-Chloro-pyrazine-2-carboxylic acid [3-((S)-2-amino-4-methyl-5,6-dihydro-4H-[1,3]oxazin-4-yl)-4-fluoro-phenyl]-amide,
5-Methyl-pyridine-2-carboxylic acid [3-((S)-2-amino-4-methyl-5,6-dihydro-4H-[1,3]oxazin-4-yl)-4-fluoro-phenyl]-amide,
3-Trifluoromethyl-pyridine-2-carboxylic acid [3-((S)-2-amino-4-methyl-5,6-dihydro-4H-[1,3]oxazin-4-yl)-4-fluoro-phenyl]-amide,
5-Methyl-thiophene-2-carboxylic acid [3-((S)-2-amino-4-methyl-5,6-dihydro-4H-[1,3]oxazin-4-yl)-4-fluoro-phenyl]-amide,
Pyridine-2-carboxylic acid [3-((S)-2-amino-4-ethyl-5,6-dihydro-4H-[1,3]oxazin-4-yl)-4-fluoro-phenyl]-amide,
5-Chloro-pyridine-2-carboxylic acid [3-((S)-2-amino-4-ethyl-5,6-dihydro-4H-[1,3]oxazin-4-yl)-4-fluoro-phenyl]-amide,
5-Methyl-thiophene-2-carboxylic acid [3-((S)-2-amino-4-ethyl-5,6-dihydro-4H-[1,3]oxazin-4-yl)-4-fluoro-phenyl]-amide,
5-Chloro-thiophene-2-carboxylic acid [3-((S)-2-amino-4-ethyl-5,6-dihydro-4H-[1,3]oxazin-4-yl)-4-fluoro-phenyl]-amide,
3,5-Dichloro-pyridine-2-carboxylic acid [3-((S)-2-amino-4-ethyl-5,6-dihydro-4H-[1,3]oxazin-4-yl)-4-fluoro-phenyl]-amide,
5-Chloro-3-methyl-pyridine-2-carboxylic acid [3-((S)-2-amino-4-ethyl-5,6-dihydro-4H-[1,3]oxazin-4-yl)-4-fluoro-phenyl]-amide,
2-Methyl-oxazole-4-carboxylic acid [3-((S)-2-amino-4-ethyl-5,6-dihydro-4H-[1,3]oxazin-4-yl)-4-fluoro-phenyl]-amide,
5-Cyano-pyridine-2-carboxylic acid [3-((S)-2-amino-4-methyl-5,6-dihydro-4H-[1,3]oxazin-4-yl)-4-fluoro-phenyl]-amide,
5-Chloro-3-methyl-pyridine-2-carboxylic acid [3-((S)-2-amino-4-methyl-5,6-dihydro-4H-[1,3]oxazin-4-yl)-4-fluoro-phenyl]-amide,
3-Methoxy-pyridine-2-carboxylic acid [3-((S)-2-amino-4-methyl-5,6-dihydro-4H-[1,3]oxazin-4-yl)-4-fluoro-phenyl]-amide,
2-Methyl-thiazole-4-carboxylic acid [3-((S)-2-amino-4-methyl-5,6-dihydro-4H-[1,3]oxazin-4-yl)-4-fluoro-phenyl]-amide,
1-Methyl-1H-pyrazole-3-carboxylic acid [3-((S)-2-amino-4-methyl-5,6-dihydro-4H-[1,3]oxazin-4-yl)-4-fluoro-phenyl]-amide,
5-Methoxy-pyridine-2-carboxylic acid [3-((S)-2-amino-4-methyl-5,6-dihydro-4H-[1,3]oxazin-4-yl)-4-fluoro-phenyl]-amide,
3-Chloro-5-trifluoromethyl-pyridine-2-carboxylic acid [3-((S)-2-amino-4-methyl-5,6-dihydro-4H-[1,3]oxazin-4-yl)-4-fluoro-phenyl]-amide,
6-Chloro-pyridine-2-carboxylic acid [3-((S)-2-amino-4-methyl-5,6-dihydro-4H-[1,3]oxazin-4-yl)-4-fluoro-phenyl]-amide,
3,5-Difluoro-pyridine-2-carboxylic acid [3-((S)-2-amino-4-methyl-5,6-dihydro-4H-[1,3]oxazin-4-yl)-4-fluoro-phenyl]-amide,
3-Methyl-thiophene-2-carboxylic acid [3-((S)-2-amino-4-methyl-5,6-dihydro-4H-[1,3]oxazin-4-yl)-4-fluoro-phenyl]-amide,
3-Chloro-5-fluoro-pyridine-2-carboxylic acid [3-((S)-2-amino-4-methyl-5,6-dihydro-4H-[1,3]oxazin-4-yl)-4-fluoro-phenyl]-amide,
5-Chloro-pyridine-2-carboxylic acid [3-((S)-6-amino-8-methyl-5-oxa-7-aza-spiro[2.5]oct-6-en-8-yl)-4-fluoro-phenyl]-amide,
3-Fluoro-pyridine-2-carboxylic acid [3-((S)-6-amino-8-methyl-5-oxa-7-aza-spiro[2.5]oct-6-en-8-yl)-4-fluoro-phenyl]-amide,
5-Chloro-3-methyl-pyridine-2-carboxylic acid [3-((S)-6-amino-8-methyl-5-oxa-7-aza-spiro[2.5]oct-6-en-8-yl)-4-fluoro-phenyl]-amide,
5-Methoxy-pyridine-2-carboxylic acid [3-((S)-6-amino-8-methyl-5-oxa-7-aza-spiro[2.5]oct-6-en-8-O-4-fluoro-phenyl]-amide,
5-Fluoro-pyridine-2-carboxylic acid [3-((S)-6-amino-8-methyl-5-oxa-7-aza-spiro[2.5]oct-6-en-8-yl)-4-fluoro-phenyl]-amide,
5-Cyano-pyridine-2-carboxylic acid [3-((S)-6-amino-8-methyl-5-oxa-7-aza-spiro[2.5]oct-6-en-8-yl)-4-fluoro-phenyl]-amide,
5-Difluoromethoxy-pyridine-2-carboxylic acid [3-((S)-6-amino-8-methyl-5-oxa-7-aza-spiro[2.5]oct-6-en-8-yl)-4-fluoro-phenyl]-amide,
Pyridine-2-carboxylic acid [3-((S)-6-amino-8-methyl-5-oxa-7-aza-spiro[2.5]oct-6-en-8-yl)-4-fluoro-phenyl]-amide,
5-Chloro-pyrimidine-2-carboxylic acid [3-((S)-6-amino-8-methyl-5-oxa-7-aza-spiro[2.5]oct-6-en-8-O-4-fluoro-phenyl]-amide,
N-[3-((S)-2-Amino-4-methyl-5,6-dihydro-4H-[1,3]oxazin-4-yl)-4-fluoro-phenyl]-2,3,3,3-tetrafluoro-propionamide,
2,2-Difluoro-cyclopropanecarboxylic acid [3-((S)-2-amino-4-methyl-5,6-dihydro-4H-[1,3]oxazin-4-yl)-4-fluoro-phenyl]-amide,
(S)—N-(3-(6-amino-8-methyl-5-oxa-7-azaspiro[2.5]oct-6-en-8-yl)-4-fluorophenyl)-2,6-difluorobenzamide,
(S)—N-(3-(6-amino-8-methyl-5-oxa-7-azaspiro[2.5]oct-6-en-8-yl)-4-fluorophenyl)-3-chloropicolinamide,
(S)—N-(3-(6-amino-8-methyl-5-oxa-7-azaspiro[2.5]oct-6-en-8-yl)-4-fluorophenyl)-3,5-difluoropicolinamide,
(S)—N-(3-(6-amino-8-methyl-5-oxa-7-azaspiro[2.5]oct-6-en-8-yl)-4-fluorophenyl)-3-chloro-5-(trifluoromethyl)picolinamide,
(S)—N-(3-(6-amino-8-methyl-5-oxa-7-azaspiro[2.5]oct-6-en-8-yl)-4-fluorophenyl)-3-(trifluoromethyl)picolinamide,
(S)—N-(3-(6-amino-8-methyl-5-oxa-7-azaspiro[2.5]oct-6-en-8-yl)-4-fluorophenyl)-3-chloro-5-fluoropicolinamide,
(S)—N-(3-(6-amino-8-methyl-5-oxa-7-azaspiro[2.5]oct-6-en-8-yl)-4-fluorophenyl)-3,5-dichloropicolinamide,
(S)—N-(3-(6-amino-8-methyl-5-oxa-7-azaspiro[2.5]oct-6-en-8-yl)-4-fluorophenyl)-1-(trifluoromethyl)cyclopropanecarboxamide,
N-(3-((S)-6-amino-8-methyl-5-oxa-7-azaspiro[2.5]oct-6-en-8-yl)-4-fluorophenyl)-2,2-difluorocyclopropanecarboxamide,
(S)—N-(3-(6-amino-8-methyl-5-oxa-7-azaspiro[2.5]oct-6-en-8-yl)-4-fluorophenyl)-4-chloro-1-methyl-1H-pyrazole-3-carboxamide,
(S)—N-(3-(6-amino-8-methyl-5-oxa-7-azaspiro[2.5]oct-6-en-8-yl)-4-fluorophenyl)-5-chloro-4-methylisoxazole-3-carboxamide,
1-Trifluoromethyl-cyclopropanecarboxylic acid [3-((S)-2-amino-4-methyl-5,6-dihydro-4H-[1,3]oxazin-4-yl)-4-fluoro-phenyl]-amide, N-[3-((S)-2-Amino-4-methyl-5,6-dihydro-4H-[1,3]oxazin-4-yl)-4-fluoro-phenyl]-3,3,3-trifluoro-propionamide,
(S)—N-(3-(2-amino-4-methyl-5,6-dihydro-4H-1,3-oxazin-4-yl)-4-fluorophenyl)-3-(2,2,2-trifluoroethoxy)picolinamide,
5-Difluoromethoxy-pyridine-2-carboxylic acid [3-((S)-2-amino-4-methyl-5,6-dihydro-4H-[1,3]oxazin-4-yl)-4-fluoro-phenyl]-amide,
(S)—N-(3-(2-amino-4-methyl-5,6-dihydro-4H-1,3-oxazin-4-yl)-4-fluorophenyl)-3-methyloxetane-3-carboxamide,
(S)—N-(3-(2-amino-4-methyl-5,6-dihydro-4H-1,3-oxazin-4-yl)-4-fluorophenyl)-4-methylisoxazole-3-carboxamide, and
4-Chloro-1H-pyrazole-3-carboxylic acid [3-((S)-2-amino-4-methyl-5,6-dihydro-4H-[1,3]oxazin-4-yl)-4-fluoro-phenyl]-amide,
or pharmaceutically acceptable salts thereof.

In a particular embodiment, the invention relates to compounds of formula I as herein described, selected from the group consisting of
3,5-Dichloro-pyridine-2-carboxylic acid [3-((S)-2-amino-4-ethyl-5,6-dihydro-4H-[1,3]oxazin-4-yl)-4-fluoro-phenyl]-amide,
5-Chloro-3-methyl-pyridine-2-carboxylic acid [3-((S)-2-amino-4-ethyl-5,6-dihydro-4H-[1,3]oxazin-4-yl)-4-fluoro-phenyl]-amide,
2-Methyl-oxazole-4-carboxylic acid [3-((S)-2-amino-4-ethyl-5,6-dihydro-4H-[1,3]oxazin-4-yl)-4-fluoro-phenyl]-amide,
5-Cyano-pyridine-2-carboxylic acid [3-((S)-2-amino-4-methyl-5,6-dihydro-4H-[1,3]oxazin-4-yl)-4-fluoro-phenyl]-amide,
5-Chloro-3-methyl-pyridine-2-carboxylic acid [3-((S)-2-amino-4-methyl-5,6-dihydro-4H-[1,3]oxazin-4-yl)-4-fluoro-phenyl]-amide,
2-Methyl-thiazole-4-carboxylic acid [3-((S)-2-amino-4-methyl-5,6-dihydro-4H-[1,3]oxazin-4-yl)-4-fluoro-phenyl]-amide,
1-Methyl-1H-pyrazole-3-carboxylic acid [3-((S)-2-amino-4-methyl-5,6-dihydro-4H-[1,3]oxazin-4-yl)-4-fluoro-phenyl]-amide,
6-Chloro-pyridine-2-carboxylic acid [3-((S)-2-amino-4-methyl-5,6-dihydro-4H-[1,3]oxazin-4-yl)-4-fluoro-phenyl]-amide,
3,5-Difluoro-pyridine-2-carboxylic acid [3-((S)-2-amino-4-methyl-5,6-dihydro-4H-[1,3]oxazin-4-yl)-4-fluoro-phenyl]-amide,
5-Chloro-3-methyl-pyridine-2-carboxylic acid [3-((S)-6-amino-8-methyl-5-oxa-7-aza-spiro[2.5]oct-6-en-8-yl)-4-fluoro-phenyl]-amide,
(S)—N-(3-(6-amino-8-methyl-5-oxa-7-azaspiro[2.5]oct-6-en-8-yl)-4-fluorophenyl)-3,5-dichloropicolinamide, and
(S)—N-(3-(6-amino-8-methyl-5-oxa-7-azaspiro[2.5]oct-6-en-8-yl)-4-fluorophenyl)-4-chloro-1-methyl-1H-pyrazole-3-carboxamide,
or pharmaceutically acceptable salts thereof.

In a particular embodiment, the invention relates to compounds of formula I as herein described, selected from the group consisting of
3,5-dichloro-pyridine-2-carboxylic acid [3-((S)-2-amino-4-methyl-5,6-dihydro-4H-[1,3]oxazin-4-yl)-4-fluoro-phenyl]-amide,
5-chloro-pyridine-2-carboxylic acid [3-((S)-2-amino-4-methyl-5,6-dihydro-4H-[1,3]oxazin-4-yl)-4-fluoro-phenyl]-amide,
5-fluoro-pyridine-2-carboxylic acid [3-((S)-2-amino-4-methyl-5,6-dihydro-4H-[1,3]oxazin-4-yl)-4-fluoro-phenyl]-amide,
pyridine-2-carboxylic acid [3-((S)-2-amino-4-methyl-5,6-dihydro-4H-[1,3]oxazin-4-yl)-4-fluoro-phenyl]-amide,
5-trifluoromethyl-pyridine-2-carboxylic acid [3-((S)-2-amino-4-methyl-5,6-dihydro-4H-[1,3]oxazin-4-yl)-4-fluoro-phenyl]-amide,
3-fluoro-pyridine-2-carboxylic acid [3-((S)-2-amino-4-methyl-5,6-dihydro-4H-[1,3]oxazin-4-yl)-4-fluoro-phenyl]-amide,
5-fluoro-thiophene-2-carboxylic acid [3-((S)-2-amino-4-methyl-5,6-dihydro-4H-[1,3]oxazin-4-yl)-4-fluoro-phenyl]-amide,
2-methyl-oxazole-4-carboxylic acid [3-((S)-2-amino-4-methyl-5,6-dihydro-4H-[1,3]oxazin-4-yl)-4-fluoro-phenyl]-amide,
4-chloro-pyridine-2-carboxylic acid [3-((S)-2-amino-4-methyl-5,6-dihydro-4H-[1,3]oxazin-4-yl)-4-fluoro-phenyl]-amide,
5-chloro-thiophene-2-carboxylic acid [3-(S)-2-amino-4-methyl-5,6-dihydro-4H-[1,3]oxazin-4-yl)-4-fluoro-phenyl]-amide,
thieno[2,3-c]pyridine-7-carboxylic acid [3-(S)-2-amino-4-methyl-5,6-dihydro-4H-[1,3]oxazin-4-yl)-4-fluoro-phenyl]-amide,
3-phenyl-pyridine-2-carboxylic acid [3-((S)-2-amino-4-methyl-5,6-dihydro-4H-[1,3]oxazin-4-yl)-4-fluoro-phenyl]-amide,
benzo[b]thiophene-2-carboxylic acid [3-((S)-2-amino-4-methyl-5,6-dihydro-4H-[1,3]oxazin-4-yl)-4-fluoro-phenyl]-amide,
5-chloro-pyrazine-2-carboxylic acid [3-((S)-2-amino-4-methyl-5,6-dihydro-4H-[1,3]oxazin-4-yl)-4-fluoro-phenyl]-amide,
5-methyl-pyridine-2-carboxylic acid [3-((S)-2-amino-4-methyl-5,6-dihydro-4H-[1,3]oxazin-4-yl)-4-fluoro-phenyl]-amide,
3-trifluoromethyl-pyridine-2-carboxylic acid [3-((S)-2-amino-4-methyl-5,6-dihydro-4H-[1,3]oxazin-4-yl)-4-fluoro-phenyl]-amide,
5-methyl-thiophene-2-carboxylic acid [3-((S)-2-amino-4-methyl-5,6-dihydro-4H-[1,3]oxazin-4-yl)-4-fluoro-phenyl]-amide, pyridine-2-carboxylic acid [3-((S)-2-amino-4-ethyl-5,6-dihydro-4H-[1,3]oxazin-4-yl)-4-fluoro-phenyl]-amide,
5-chloro-pyridine-2-carboxylic acid [3-((S)-2-amino-4-ethyl-5,6-dihydro-4H-[1,3]oxazin-4-yl)-4-fluoro-phenyl]-amide,
5-methyl-thiophene-2-carboxylic acid [3-((S)-2-amino-4-ethyl-5,6-dihydro-4H-[1,3]oxazin-4-yl)-4-fluoro-phenyl]-amide,
5-chloro-thiophene-2-carboxylic acid [3-((S)-2-amino-4-ethyl-5,6-dihydro-4H-[1,3]oxazin-4-yl)-4-fluoro-phenyl]-amide,
3,5-dichloro-pyridine-2-carboxylic acid [3-((S)-2-amino-4-ethyl-5,6-dihydro-4H-[1,3]oxazin-4-yl)-4-fluoro-phenyl]-amide,
5-chloro-3-methyl-pyridine-2-carboxylic acid [3-((S)-2-amino-4-ethyl-5,6-dihydro-4H-[1,3]oxazin-4-yl)-4-fluoro-phenyl]-amide,
2-methyl-oxazole-4-carboxylic acid [3-((S)-2-amino-4-ethyl-5,6-dihydro-4H-[1,3]oxazin-4-yl)-4-fluoro-phenyl]-amide,
5-cyano-pyridine-2-carboxylic acid [3-((S)-2-amino-4-methyl-5,6-dihydro-4H-[1,3]oxazin-4-yl)-4-fluoro-phenyl]-amide, 5-chloro-3-methyl-pyridine-2-carboxylic acid [3-((S)-2-amino-4-methyl-5,6-dihydro-4H-[1,3]oxazin-4-yl)-4-fluoro-phenyl]-amide, 3-methoxy-pyridine-2-carboxylic acid [3-((S)-2-amino-4-methyl-5,6-dihydro-4H-[1,3]oxazin-4-yl)-4-fluoro-phenyl]-amide, 2-methyl-thiazole-4-carboxylic acid [3-((S)-2-amino-4-methyl-5,6-dihydro-4H-[1,3]oxazin-4-yl)-4-fluoro-phenyl]-amide, 1-methyl-1H-pyrazole-3-carboxylic acid [3-((S)-2-amino-4-methyl-5,6-dihydro-4H-[1,3]oxazin-4-yl)-4-fluoro-phenyl]-amide, 5-methoxy-pyridine-2-carboxylic acid [3-((S)-2-amino-4-methyl-5,6-dihydro-4H-[1,3]oxazin-4-yl)-4-fluoro-phenyl]-amide, 3-chloro-5-trifluoromethyl-pyridine-2-carboxylic acid [3-((S)-2-amino-4-methyl-5,6-dihydro-4H-[1,3]oxazin-4-yl)-4-fluoro-phenyl]-amide, 6-chloro-pyridine-2-carboxylic acid [3-((S)-2-amino-4-methyl-5,6-dihydro-4H-[1,3]oxazin-4-yl)-4-fluoro-phenyl]-amide, 3,5-difluoro-pyridine-2-carboxylic acid [3-((S)-2-amino-4-methyl-5,6-dihydro-4H-[1,3]oxazin-4-yl)-4-fluoro-phenyl]-amide, 3-methyl-thiophene-2-carboxylic acid [3-((S)-2-amino-4-methyl-5,6-dihydro-4H-[1,3]oxazin-4-yl)-4-fluoro-phenyl]-amide, 3-chloro-5-fluoro-pyridine-2-carboxylic acid [3-((S)-2-amino-4-methyl-5,6-dihydro-4H-[1,3]oxazin-4-yl)-4-fluoro-phenyl]-amide, or pharmaceutically acceptable salts thereof.

In a particular embodiment, the invention relates to a process of synthesizing compounds of formula I as herein described, which process comprises reacting an amine of the formula II

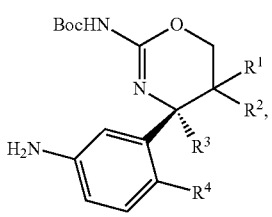

wherein $R^1$ to $R^4$ are as defined herein and Boc is the protecting group tert-butyloxycarbonyl, with a carboxylic acid of the formula III

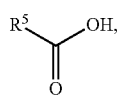

wherein $R^5$ is as defined herein, in the presence of a coupling reagent under basic conditions to obtain a compound of the formula IV

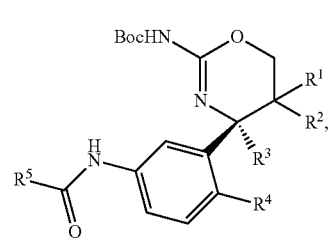

and deprotecting the compound of formula IV with the help of a mineral acid to obtain the compound of formula I

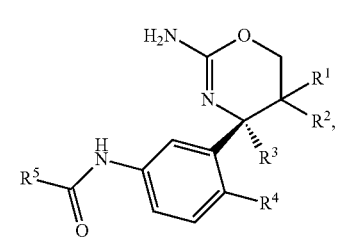

wherein $R^1$ to $R^5$ are as defined herein.

In a particular embodiment, the invention relates to pharmaceutical compositions comprising a compound of formula I as described herein and a pharmaceutically acceptable carrier and/or adjuvant.

In a particular embodiment, the invention relates to compounds of formula I as described herein for use as medicaments.

In a particular embodiment, the invention relates to compounds of formula I as described herein for use as medicaments for the treatment or prevention of diseases which are associated with inhibition of BACE2 activity.

In a particular embodiment, the invention relates to compounds of formula I as described herein for use as medicaments for the treatment or prevention of diabetes, particularly type 2 diabetes.

In a particular embodiment, the invention relates to compounds of formula I as described herein for use as medicaments for the treatment or prevention of type 2 diabetes.

In a particular embodiment, the invention relates to a method for the treatment of diseases which are associated with the inhibition of BACE 2 activity, particularly for the treatment of type 2 diabetes, which method comprises administering a therapeutically active amount of a compound of formula I as described herein to a human being or animal.

In a particular embodiment, the invention relates to the use of compounds of formula I as described herein for the preparation of medicaments for the treatment or prevention of diseases which are associated with the inhibition of BACE2 activity.

In a particular embodiment, the invention relates to the use of compounds of formula I as described herein for the preparation of medicaments for the treatment or prevention of diabetes, particularly type 2 diabetes.

Particularly, $R^3$ signifies $C_{1-7}$-alkyl. Compounds of formula I of the present invention are particular, wherein $R^3$ is methyl or ethyl.

Another group of particular compounds are those, wherein or $R^2$ and $R^3$ together with the C atoms they are attached to form a $C_{3-7}$-cycloalkyl or a 3- to 7-membered O-heterocyclyl ring, with those compounds being more particular, wherein $R^2$ and $R^3$ together with the C atoms they are attached to form a 3- to 7-membered O-heterocyclyl ring.

Furthermore, compounds of formula I according to the invention are particular, wherein $R^4$ is hydrogen or halogen. More particularly, $R^4$ is halogen. Especially particular are compounds of formula I, wherein $R^4$ is hydrogen or fluoro, with those compounds of formula I, wherein $R^4$ is fluoro being most particular.

In addition, compounds of formula I according to the present invention are particular, wherein $R^5$ is heteroaryl, said heteroaryl being unsubstituted or substituted by one, two or three groups selected from the group consisting of $C_{1-7}$-alkyl, halogen, halogen-$C_{1-7}$-alkyl, $C_{1-7}$-alkoxy, halogen-$C_{1-7}$-alkoxy, cyano, hydroxy-$C_{1-7}$-alkyl, oxo and phenyl.

Particularly particular compounds of formula I of the present invention are the following:

3,5-dichloro-pyridine-2-carboxylic acid [3-((S)-2-amino-4-methyl-5,6-dihydro-4H-[1,3]oxazin-4-yl)-4-fluoro-phenyl]-amide, 5-fluoro-pyridine-2-carboxylic acid [3-((S)-2-amino-4-methyl-5,6-dihydro-4H-[1,3]oxazin-4-yl)-4-fluoro-phenyl]-amide, 3,5-dichloro-pyridine-2-carboxylic acid [3-((S)-2-amino-4-ethyl-5,6-dihydro-4H-[1,3]oxazin-4-yl)-4-fluoro-phenyl]-amide, 5-chloro-3-methyl-pyridine-2-carboxylic acid [3-((S)-2-amino-4-ethyl-5,6-dihydro-4H-[1,3]oxazin-4-yl)-4-fluoro-phenyl]-amide, 2-methyl-oxazole-4-carboxylic acid [3-((S)-2-amino-4-ethyl-5,6-dihydro-4H-[1,3]oxazin-4-yl)-4-fluoro-phenyl]-amide, 5-cyano-pyridine-2-carboxylic acid [3-((S)-2-amino-4-methyl-5,6-dihydro-4H-[1,3]oxazin-4-yl)-4-fluoro-phenyl]-amide, 5-chloro-3-methyl-pyridine-2-carboxylic acid [3-((S)-2-amino-4-methyl-5,6-dihydro-4H-[1,3]oxazin-4-yl)-4-fluoro-phenyl]-amide, 2-methyl-thiazole-4-carboxylic acid [3-((S)-2-amino-4-methyl-5,6-dihydro-4H-[1,3]oxazin-4-yl)-4-fluoro-phenyl]-amide, 1-methyl-1H-pyrazole-3-carboxylic acid [3-((S)-2-amino-4-methyl-5,6-dihydro-4H-[1,3]oxazin-4-yl)-4-fluoro-phenyl]-amide, 6-chloro-pyridine-2-carboxylic acid [3-((S)-2-amino-4-methyl-5,6-dihydro-4H-[1,3]oxazin-4-yl)-4-fluoro-phenyl]-amide, 3,5-difluoro-pyridine-2-carboxylic acid [3-((S)-2-amino-4-methyl-5,6-dihydro-4H-[1,3]oxazin-4-yl)-4-fluoro-phenyl]-amide, or pharmaceutically acceptable salts thereof.

The pharmaceutically acceptable salts of the compounds of formula I also individually constitute particular compounds of the present invention.

Especially particular are the salts of compounds of formula I with HCl, formic acid and trifluoroacetic acid ($CF_3COOH$), i.e. the chloride salts, the formate salts and trifluoroacetate salts.

The skilled person in the art will recognize that the compounds of formula I can exist in tautomeric forms, e.g. in the following tautomeric form:

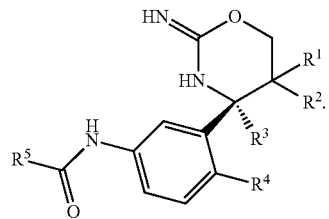

I-A

All tautomeric forms are encompassed in the present invention.

Compounds of formula I possess one asymmetric carbon atom and can exist in the form of optically pure enantiomers and mixtures of enantiomers such as, for example, racemates. The optically active forms can be obtained for example by resolution of the racemates, by asymmetric synthesis or asymmetric chromatography (chromatography with a chiral adsorbens or eluant). The invention embraces all of these forms.

It will be appreciated, that the compounds of general formula I in this invention may be derivatised at functional groups to provide derivatives which are capable of conversion back to the parent compound in vivo. Physiologically acceptable and metabolically labile derivatives, which are capable of producing the parent compounds of general formula I in vivo are also within the scope of this invention.

The term "protecting group" denotes the group which selectively blocks a reactive site in a multifunctional compound such that a chemical reaction can be carried out selectively at another unprotected reactive site in the meaning conventionally associated with it in synthetic chemistry. Protecting groups can be removed at the appropriate point. Exemplary protecting groups are amino-protecting groups, carboxy-protecting groups or hydroxy-protecting groups. The term "protecting group" in context with amines denotes groups intended to protect an amino group and includes benzyl, benzyloxycarbonyl (carbobenzyloxy, CBZ), Fmoc (9-Fluorenylmethyloxycarbonyl), p-methoxybenzyloxycarbonyl, p-nitrobenzyloxycarbonyl, tert-butoxycarbonyl (BOC), and trifluoroacetyl. Further examples of these groups are found in T. W. Greene and P. G. M. Wuts, "Protective Groups in Organic Synthesis", 2nd ed., John Wiley & Sons, Inc., New York, N.Y., 1991, chapter 7; E. Haslam, "Protective Groups in Organic Chemistry", J. G. W. McOmie, Ed., Plenum Press, New York, N.Y., 1973, Chapter 5, and T. W. Greene, "Protective Groups in Organic Synthesis", John Wiley and Sons, New York, N.Y., 1981.

The term "half maximal inhibitory concentration" (IC50) denotes the concentration of a particular compound required for obtaining 50% inhibition of a biological process in vitro. IC50 values can be converted logarithmically to pIC50 values (−log IC50), in which higher values indicate exponentially greater potency. The IC50 value is not an absolute value but depends on experimental conditions e.g. concentrations employed. The IC50 value can be converted to an absolute inhibition constant (Ki) using the Cheng-Prusoff equation (Biochem. Pharmacol. (1973) 22:3099).

The term "inhibitor" denotes a compound which competes with, reduces or prevents the binding of a particular ligand to particular receptor or which reduces or prevents the inhibition of the function of a particular protein.

The term "therapeutically effective amount" denotes an amount of a compound of the present invention that, when administered to a subject, (i) treats or prevents the particular disease, condition or disorder, (ii) attenuates, ameliorates or eliminates one or more symptoms of the particular disease, condition, or disorder, or (iii) prevents or delays the onset of one or more symptoms of the particular disease, condition or disorder described herein. The therapeutically effective amount will vary depending on the compound, disease state being treated, the severity or the disease treated, the age and relative health of the subject, the route and form of administration, the judgement of the attending medical or veterinary practitioner, and other factors.

The term "treating" or "treatment" of a disease state includes (1) preventing the disease state, i.e. causing the clinical symptoms of the disease state not to develop in a subject that may be exposed to or predisposed to the disease state, but does not yet experience or display symptoms of the disease state, (2) inhibiting the disease state, i.e., arresting the development of the disease state or its clinical symptoms, or (3) relieving the disease state, i.e., causing temporary or permanent regression of the disease state or its clinical symptoms.

Appropriate coupling agents are carbodiimides or uronium salts, such as for example N,N'-carbonyldiimidazole (CDI), N,N'-dicyclohexylcarbodiimide (DCC), N-(3-dimethylaminopropyl)-N'-ethyl-carbodiimide-hydrochloride (EDCI), O-(benzotriazol-1-yl)-N,N,N,N-tetramethyluronium tetrafluoroborate (TBTU) and 1-[bis(dimethylamino)methylene]-1H-1,2,3-triazolo[4,5-b]pyridinium-3-oxide hexafluorophosphate (HATU). The term "under basic conditions" means the presence of a base, particularly an alkylamine such as diisopropylethylamine (DIEA) or triethylamine (TEA), or a tertiary amine such as N-methylmorpholine or 4-(dimethylamino)-pyridine. The reaction is carried out in a suitable solvent such as for example N,N-dimethylformamide (DMF) or dimethylacetamide (DMAc), at temperatures between 0° C. and ambient temperature.

Particular mineral acids for the deprotection are sulfuric acid or hydrochloric acid, more particularly hydrochloric acid in a solvent such as an ether, particularly diethyl ether or 1,4-dioxane, or neat trifluoroacetic acid.

The invention further relates to compounds of formula I as defined above obtainable according to a process as defined above.

In more detail, compounds of formula I according to the present invention can be prepared by the methods and procedures given below. Typical procedures for the preparation of compounds of formula I is illustrated in Schemes 1 and 2.

Scheme 1:
Synthesis of compounds of formula I

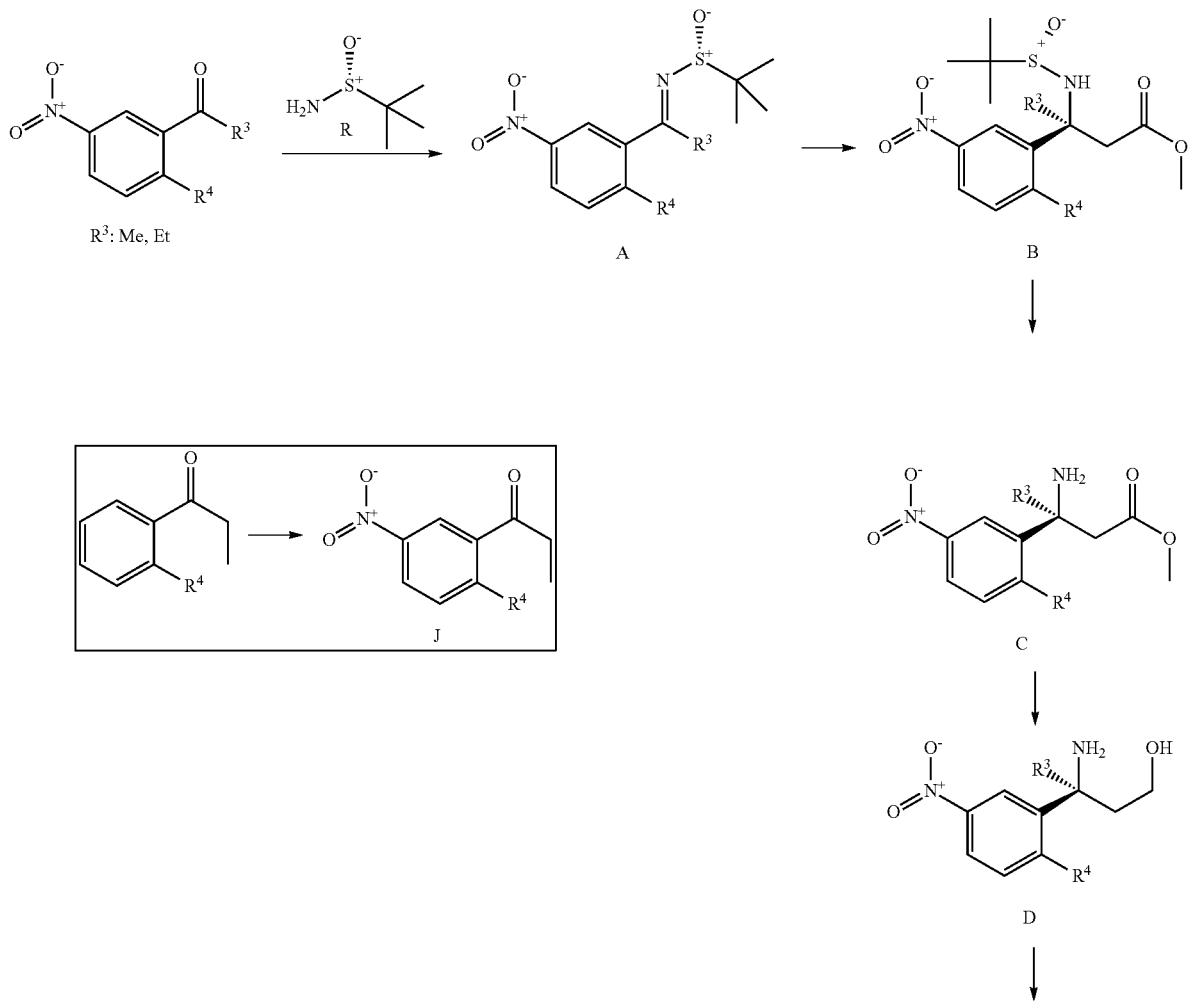

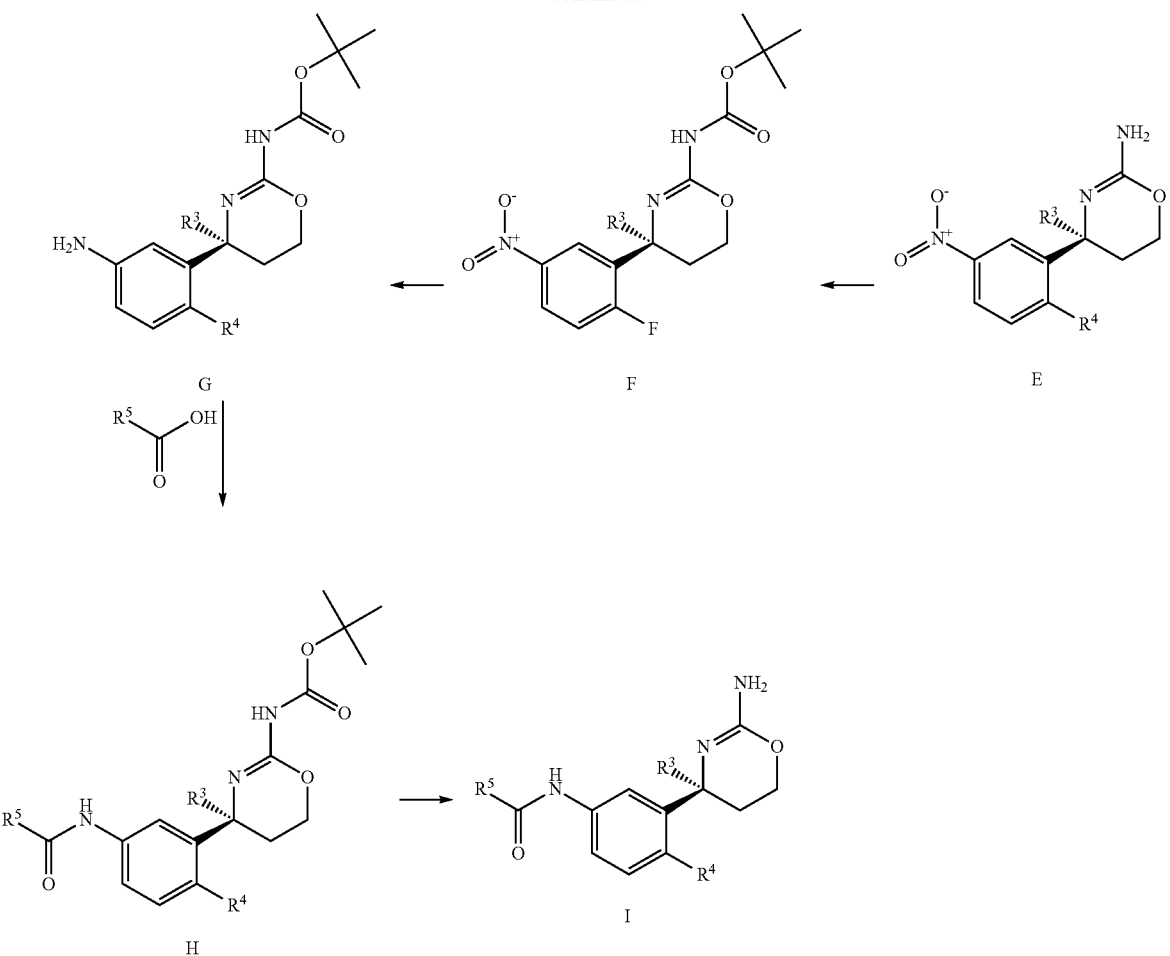
Scheme 2:
Alternative synthesis of compounds of formula I
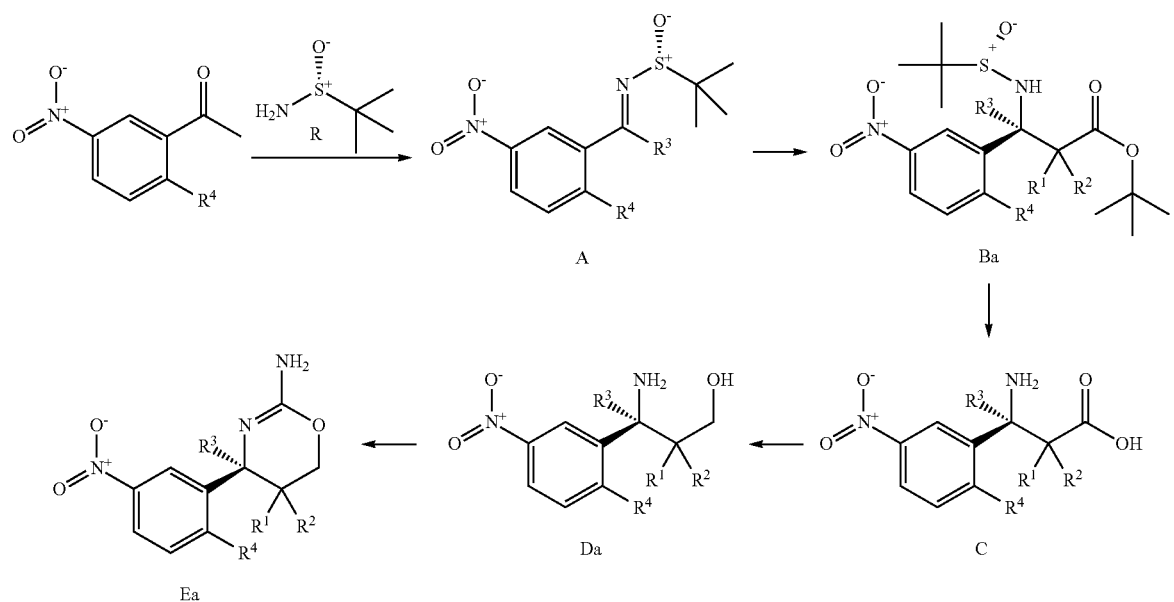

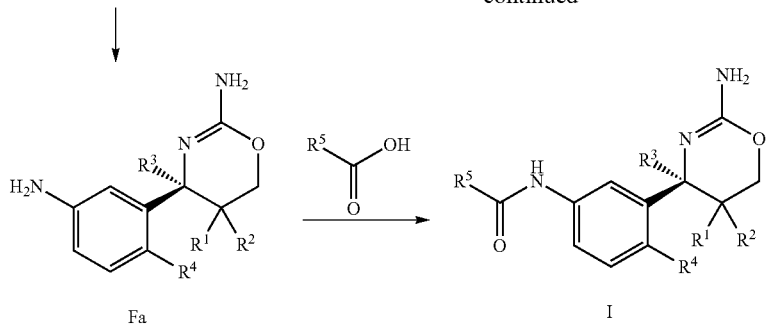

Scheme 3:
Alternative synthesis of compounds of formula I (X = O/C)

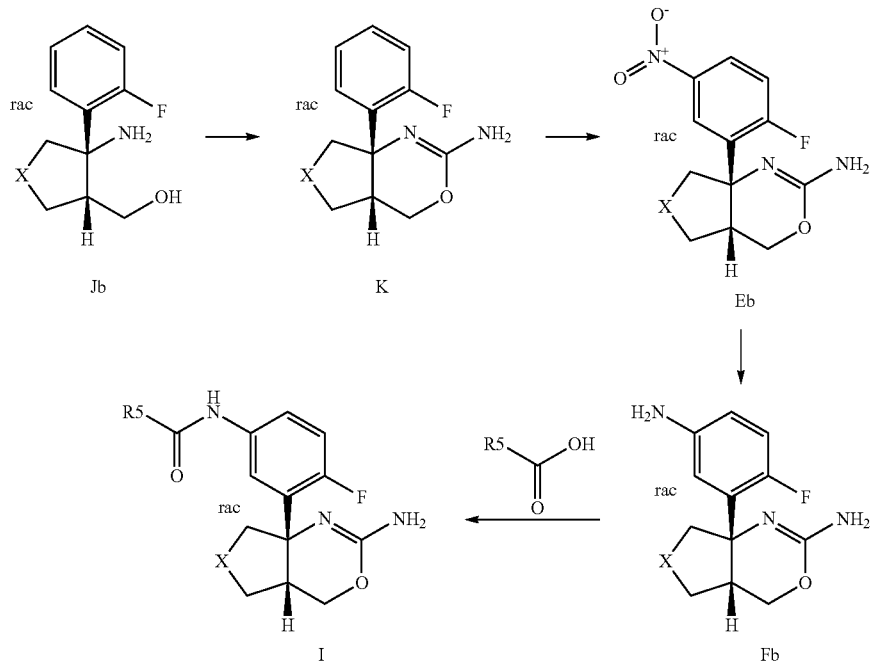

Sulfinyl imines of general formula A can be prepared in analogy to T. P. Tang & J. A. Ellman, J. Org. Chem. 1999, 64, 12, by condensation of an aryl ketone and a sulfinamide, e.g. an alkyl sulfinamide, most particularly (R)-(+)-tert-butylsulfinamide in the presence of a Lewis acid such as e.g. a titanium(IV)alkoxyde, more particularly titanium(IV)ethoxide in a solvent such as an ether, e.g. diethyl ether or more particularly THF.

The conversion of the sulfinyl imine A to the sulfinamide ester B or Ba proceeds stereoselectively by the chiral directing group as described by Tang & Ellman. The sulfinyl imine A can be reacted with a titanium enolate generated from e.g. an alkyl acetate, particularly methyl acetate, LDA and chlorotriisopropoxytitanium at low temperature, particularly at −78° C. in a solvent such as an ether, e.g. diethyl ether or more particularly THF.

Hydrolysis of the chiral directing group in the sulfinamide ester B to give the amino ester C can be accomplished with a mineral acid, e.g. sulfuric acid or particularly hydrochloric acid in a solvent such as an ether, e.g. diethyl ether or more particularly 1,4-dioxane.

Aminoalcohol D can be prepared by the reduction of the methylester with an alkali hydride, particularly lithium borohydride or lithium aluminium hydride in a solvent such as an ether, e.g. diethyl ether or more particularly THF.

Aminooxazine E can be prepared by a two-step procedure involving first the reaction of amino alcohol D and cyanogenbromide in a solvent such as an ether, particularly THF, followed by reaction with a mineral acid, particularly hydrochloric acid in a solvent such as THF.

Boc-protected Aminooxazine F can be prepared by reaction of aminooxazine with di-tert-butyl-dicarbonate with an alkylamine such as TEA or particularly diisopropylamine in a solvent such as an ether, particularly THF.

The reduction of the nitro group in the Boc-protected Aminooxazine F to the aniline G can be accomplished by hydrogenation using a catalysts such as Pd/C in protic solvents, such as alcohols, preferably ethanol or methanol.

Amide coupling of the aniline G and a carboxylic acid to give the amide H can be effected with a carbodiimide, e.g. DCC or EDCI in a solvent such as dichloromethane. Deprotection of the tert-butyloxycarbonyl group in H is effected with trifluoroacetic acid in a solvent such as dichloromethane.

Alternatively, hydrolysis of the chiral directing group and the t-butyl ester in the sulfinamide ester Ba to give the amino acid Ca can be accomplished with a mineral acid, e.g. sulfuric acid or particularly hydrochloric acid in a solvent such as an ether, e.g. diethyl ether or 1,4-dioxane or an ester e.g. methyl acetate or more particularly ethyl acetate.

The reduction of the amino acid Ca to give the amino alcohol Da can be effected with an alkali hydride, e.g. lithium borohydride or lithium aluminium hydride or a borane, preferably $BH_3$-THF complex in an ether as solvent, e.g. diethyl ether or more particularly THF.

Ring closure of the amino alcohol Da to give the amino oxazine Ea can be prepared by a two-step procedure involving first the reaction of the amino alcohol Da and cyanogenbromide in a solvent such as an ether, particularly THF, followed by reaction with a mineral acid, particularly hydrochloric acid in a solvent such as THF.

The reduction of the nitro group in the intermediate Ea to give the aniline Fa can be accomplished by hydrogenation using a catalyst such as Pd/C in protic solvents, such as alcohols, particularly methanol or more particularly ethanol.

Coupling of the aniline Fa and a carboxylic acid to give the amide I was best accomplished with 4-(4,6-dimethoxy-1,3,5-triazin-2-yl)-4-methyl-morpholinium chloride in a protic solvent such as an alcohol, particularly methanol.

Alternatively, aminooxazines K can be prepared from an amino alcohol such as Jb (preparation described in WO 2009091016) by a two-step procedure involving first the reaction of amino alcohol J and cyanogenbromide in a solvent such as an ether, particularly THF, followed by reaction with a mineral acid, particularly hydrochloric acid in a solvent such as THF.

Introduction of the nitro group in K to give Eb was best performed according to the standard procedure involving sulfuric acid and nitric acid at low temperature, preferably at 0° C.

The reduction of the nitro group in aminooxazine Eb to the aniline Fb can be accomplished by hydrogenation using a catalyst such as Pd/C in protic solvents, such as alcohols, particularly methanol or more particularly ethanol.

Amide coupling of the aniline Fb and a carboxylic acid to give the amides I can be effected with a carbodiimide, e.g. DCC, EDCI or preferably DMTMM in a suitable solvent such as methanol.

As described herein before, the compounds of formula I of the present invention can be used as medicaments for the treatment of diseases which are associated with the inhibition of BACE2.

As described herein before, the compounds of formula I of the present invention can be used as medicaments for the treatment of diseases which are associated with the inhibition of BACE2.

As described herein before, the compounds of formula I of the invention will be useful in preserving and restoring beta-cell function and stimulating insulin secretion in diabetic patients and in non-diabetic patients who have impaired glucose tolerance or who are in a pre-diabetic condition. They may be useful in treating type 1 diabetes or in delaying or preventing a patient with type 2 diabetes from needing insulin therapy. The compounds of formula I are further useful to ameliorate hyperinsulinemia, which often occurs in diabetic or pre-diabetic patients and in reducing the risks associated with metabolic syndrome, they may also be useful in treating vascular diseases such as hypertension.

Thus, the expression 'diseases which are associated with the inhibition of BACE2 activity' means diseases such as metabolic and cardiovascular diseases, in particular diabetes, more particularly type 2 diabetes, gestational diabetes, impaired fasting glucose, impaired glucose tolerance, insulin resistance, pre-diabetes, metabolic syndrome, diabetes type 1, complications of diabetes including diabetic nephropathy, diabetic retinopathy and diabetic neuropathy, chronic kidney disease, dyslipidemia, atherosclerosis, myocardial infarction, hypertension and further metabolic and cardiovascular disorders.

In a particular aspect, the expression 'diseases which are associated with the inhibition of BACE2 activity' relates to diabetes, particularly type II diabetes, impaired glucose tolerance, pre-diabetes, metabolic syndrome and hypertension. More particularly, the expression 'diseases which are associated with the inhibition of BACE2 activity' relates to diabetes, most particularly type 2 diabetes.

The invention also relates to pharmaceutical compositions comprising a compound as defined above and a pharmaceutically acceptable carrier and/or adjuvant. More specifically, the invention relates to pharmaceutical compositions useful for the treatment of diseases which are associated with the inhibition of BACE2 activity.

Further, the invention relates to compounds of formula I as defined above for use as medicaments, particularly as medicaments for the treatment or prevention of diseases which are associated with the inhibition of BACE2 activity. Especially particular are compounds of formula I for use in diabetes, particularly type 2 diabetes.

In another aspect, the invention relates to a method for the treatment or prevention of diseases which are associated with the inhibition of BACE2 activity, which method comprises administering a therapeutically active amount of a compound of formula I to a human being or animal. A method for the treatment of diabetes, particularly type 2 diabetes, is particular.

The invention further relates to the use of compounds of formula I as defined above for the treatment of diseases which are associated with the inhibition of BACE2 activity.

In addition, the invention relates to the use of compounds of formula I as defined above for the preparation of medicaments for the treatment or prevention of diseases which are associated with the inhibition of BACE2 activity. The use of compounds of formula I as defined above for the preparation of medicaments for the treatment or prevention of diabetes, particularly, type 2 diabetes, is especially particular.

The compounds of formula I and their pharmaceutically acceptable salts can be used as medicaments, e.g., in the form of pharmaceutical preparations for enteral, parenteral or topical administration. They can be administered, for example, perorally, e.g., in the form of tablets, coated tablets, dragées, hard and soft gelatine capsules, solutions, emulsions or suspensions, rectally, e.g., in the form of suppositories, parenterally, e.g., in the form of injection solutions or suspensions or infusion solutions, or topically, e.g., in the form of ointments, creams or oils. Oral administration is particular.

The production of the pharmaceutical preparations can be effected in a manner which will be familiar to any person skilled in the art by bringing the described compounds of formula I and their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatine capsules. Suitable carrier materials for soft gelatine capsules are, for example, vegetable oils, waxes, fats and semi-solid and liquid polyols (depending on the nature of the active ingredient no carriers might, however, be required in the case of soft gelatine capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavour-improving agents, salts for varying the osmotic pressure, buffer substances, solubilizers, colorants and masking agents and antioxidants come into consideration as pharmaceutical adjuvants.

The dosage of the compounds of formula I can vary within wide limits depending on the disease to be controlled, the age and the individual condition of the patient and the mode of administration, and will, of course, be fitted to the individual requirements in each particular case. For adult patients a daily dosage of about 1 to 1000 mg, especially about 1 to 300 mg, comes into consideration. Depending on severity of the disease and the precise pharmacokinetic profile the compound could be administered with one or several daily dosage units, e.g., in 1 to 3 dosage units.

The pharmaceutical preparations conveniently contain about 1-500 mg, particularly 1-100 mg, of a compound of formula I.

The following examples serve to illustrate the present invention in more detail. They are, however, not intended to limit its scope in any manner.

EXAMPLES

Abbreviations

DCC=N,N'-diisopropyl-carbodiimide, DIEA=diisopropylethylamine, DMAc=dimethylacetamide, DMAP=4-dimethylaminopyridine, DMF=N,N-dimethylformamide, DMSO=dimethyl sulfoxide, EDCI=N-(3-dimethylaminopropyl)-N'-ethyl-carbodiimide hydrochloride, HATU=1-[bis(dimethylamino)methylene]-1H-1,2,3-triazolo[4,5-b]pyridinium-3-oxide hexafluorophosphate, HCl=hydrogen chloride, HPLC=high performance liquid chromatography, LDA=lithium diisopropylamide, MS=mass spectrum, NMR=nuclear magnetic resonance, TEA=triethylamine, and THF=tetrahydrofuran.

Synthesis of the intermediate 1-(2-Fluoro-5-nitro-phenyl)-propan-1-one J

To a solution of the 1-(2-Fluoro-phenyl)-propan-1-one (99 mmol) in concentrated sulfuric acid (80 ml) cooled down to −30° C. was added slowly fuming nitric acid (8 ml) over 20 min and the solution was stirred at −30° C. for 15 min. The mixture was slowly poured into a stirred mixture of 200 ml of water and 400 g ice. The aqueous phase was extracted with ethyl acetate, the organic layer was extracted again with water and aqueous $NaHCO_3$ 1M. The organic layer was dried over $Na_2SO_4$, evaporated and the residue was chromatographed on silica using a mixture of heptane and ethylacetate as eluent to afford 16.5 g of the pure nitro intermediate J. MS (ESI): m/z=198.1 $[M+H]^+$.

A. Synthesis of the intermediate sulfinyl imines A

General Procedure

To a solution of the (R)-(+)-tert-butylsulfinamide (89.8 mmol) in THF (400 ml) was added subsequently the ketone (98.7 mmol) and titanium(IV) ethoxide (178.4 mmol) and the solution was stirred at reflux temperature for 5 h. The mixture was cooled to 22° C., treated with brine (400 ml), the suspension was stirred for 10 min and filtered over dicalite. The layers were separated, the aqueous layer was extracted with ethyl acetate, the combined organic layers were washed with water, dried and evaporated. The residue was chromatographed on silica using a mixture of heptane and ethyl acetate as eluent to give the pure sulfinyl imine A.

Intermediate A1 ($R^3$=Me): Starting from 1-(2-fluoro-5-nitro-phenyl)-ethanone (89.7 mmol), the product (R)-2-methyl-propane-2-sulfinic acid [1-(2-fluoro-5-nitro-phenyl)-(E)-ethylidene]-amide (21.56 g) was obtained as a pale yellow solid. MS (ESI): m/z=287.0 $[M+H]^+$.

Intermediate A2 ($R^3$=Et): Starting from 1-(2-fluoro-5-nitro-phenyl)-propan-1-one (91 mmol), the product (R)-2-methyl-propane-2-sulfinic acid [1-(2-fluoro-5-nitro-phenyl)-(E)-propylidene]-amide (21.9 g) was obtained as a pale yellow solid. MS (ESI): m/z=301.1 $[M+H]^+$.

B. Synthesis of the intermediate sulfinamide esters B

General Procedure

To a solution of diisopropylamide (7.95 ml) in THF (100 ml) was added at −78° C. n-butyllithium (1.6 M solution in hexane, 35.4 ml) and stirring was continued at −78° C. for 30 min. The solution was treated with methyl acetate (4.51 ml) and after 30 min a solution of chlorotriisopropoxytitanium (15.6 g) in THF (20 ml) was added and stirring was continued at −78° C. for 30 min. The mixture was treated with a solution of the sulfinyl imine A (17.1 mmol) in THF (10 ml) and stirring was continued at −78° C. for 3 h. The mixture was quenched with saturated aqueous $NH_4Cl$ solution (150 ml) and the mixture was filtered over dicalite. The layers were separated, the aqueous layer was extracted with ethyl acetate, the combined organic layers were washed with water, dried and evaporated. The residue was chromatographed on silica using a mixture of heptane and ethylacetate as eluent to give the pure sulfinamide ester B.

Intermediate B1 ($R^3$=Me): Starting from (R)-2-methyl-propane-2-sulfinic acid [1-(2-fluoro-5-nitro-phenyl)-(E)-ethylidene]-amide (17 mmol), the product (S)-3-(2-fluoro-5-nitro-phenyl)-3-((R)-2-methyl-propane-2-sulfinylamino)-butyric acid methyl ester (4.09 g) was obtained as a pale yellow solid. MS (ESI): m/z=361.0 $[M+H]^+$.

Intermediate B2 ($R^3$=Et): Starting from (R)-2-methyl-propane-2-sulfinic acid [1-(2-fluoro-5-nitro-phenyl)-(E)-propylidene]-amide (36 mmol), the product (S)-3-(2-fluoro-5-nitro-phenyl)-3-((R)-2-methyl-propane-2-sulfinylamino)-pentanoic acid methyl ester (3.73 g) was obtained as a pale yellow solid. MS (ESI): m/z=375.3 $[M+H]^+$.

Intermediate Ba3 ($R^{1,2}$=cyclopropyl, $R^3$=Me): To a solution of diisopropylamine (24.5 ml) in THF (300 ml) was added at −20° C. n-butyllithium (1.6 M solution in hexane, 109 ml), the mixture was warmed to 0° C. for 30 min and cooled to −78° C. The solution was treated with a solution of cyclopropanecarboxylic acid tert-butyl ester (24.8 g, preparation described in St. W. Wright et al., Tetrahedron Lett. 38, 7345 1997) in THF (50 ml) and after stirring for 4 h at −78° C. a solution of (R)-2-methyl-propane-2-sulfinic acid [1-(2-fluoro-5-nitro-phenyl)-(E)-ethylidene]-amide (50.0 g) in THF (50 ml) was added and stirring was continued for 4 h. The mixture was quenched with brine, extracted with ethyl acetate, the organic layer was dried and evaporated. The residue was purified by chromatography over silica using cyclohexane/ethylacetate (4:1) to give 1-[(S)-1-(2-fluoro-5-nitro-phenyl)-1-(R)-2-methyl-propane-2-sulfinylamino)-ethyl]-cyclopropanecarboxylic acid tert-butyl ester (17.3 g) as a pale brown oil. MS (ESI): m/z=429.3 [M+H]$^+$.

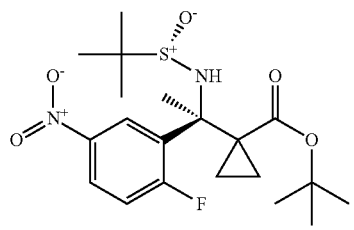

C. Synthesis of the intermediate amino esters C

General Procedure

A solution of the sulfinamide ester B (4.21 mmol) in methanol (40 ml) was treated with a solution of HCl in 1,4-dioxane (4 M, 53 ml) and stirring was continued at 22° C. for 2 h. The mixture was evaporated and the residue was partitioned between ethyl acetate and aqueous $Na_2CO_3$ 2M. The organic layer was dried and evaporated to give a residue which was chromatographed on silica using a mixture of heptane and ethal acetate as eluent to give the pure aminoester C.

Intermediate C1 ($R^3$=Me): Starting from (S)-3-(2-fluoro-5-nitro-phenyl)-3-(R)-2-methyl-propane-2-sulfinylamino)-butyric acid methyl ester (12 mmol), the product (S)-3-amino-3-(2-fluoro-5-nitro-phenyl)-butyric acid methyl ester (2.76 g) was obtained as a pale yellow solid.

MS (ESI): m/z=257.3 [M+H]$^+$.

Intermediate C2 ($R^3$=Et): Starting from (S)-3-(2-fluoro-5-nitro-phenyl)-3-((R)-2-methyl-propane-2-sulfinylamino)-pentanoic acid methyl ester (7 mmol), the product (S)-3-amino-3-(2-fluoro-5-nitro-phenyl)-pentanoic acid methyl ester (1.31 g) was obtained as a pale yellow solid. MS (ESI): m/z=271.1 [M+H]$^+$.

Intermediate Ca3: ($R^{1,2}$=cyclopropyl, $R^3$=Me): A solution of 1-[(S)-1-(2-fluoro-5-nitro-phenyl)-1-((R)-2-methyl-propane-2-sulfinylamino)-ethyl]-cyclopropanecarboxylic acid tert-butyl ester (3.0 g) in HCl/AcOEt (2M, 35 ml) was heated in a sealed tube to 65° C. for 5.5 h. The suspension was diluted with diisopropyl ether (70 ml), stirred for 1 h, filtered and the residue was dried to give the hydrochloride of 1-[(S)-1-amino-1-(2-fluoro-5-nitro-phenyl)-ethyl]-cyclopropanecarboxylic acid (2.03 g) as a pale brown solid. MS (ESI): m/z=269.2 [M+H]$^+$.

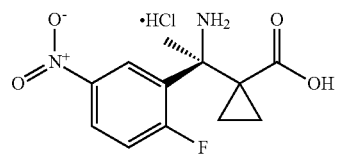

D. Synthesis of the intermediate amino alcohol D

Procedure for intermediate D1 ($R^3$=Me): (S)-3-Amino-3-(2-fluoro-5-nitro-phenyl)-butan-1-ol: A solution of the (S)-3-amino-3-(2-fluoro-5-nitro-phenyl)-butyric acid methyl ester (11.0 mmol) in 300 mL ether cooled down to −35° C. was treated with lithium aluminiumhydride (33.0 mmol) and stirring was continued at −35° C. for 90 min. The reaction mixture was then cooled down to −55° C., quenched by addition of 60 g of $Na_2SO_4 \times 10$ $H_2O$ and vigorously stirred. Filtration on dicalite, filter cake washed with Ether and collected filtrate was concentrated under vacuo to afford an oil. The residue was chromatographed on silica using a mixture of heptane and ethyl acetate as eluent to give 1.53 g of the pure amino alcohol D1. MS (ESI): m/z=229.4 [M+H]$^+$.

Procedure for intermediate D2 ($R^3$=Et): (S)-3-Amino-3-(2-fluoro-5-nitro-phenyl)-pentan-1-ol: A solution of the (S)-3-amino-3-(2-fluoro-5-nitro-phenyl)-pentanoic acid methyl ester (4.4 mmol) in 24 mL dry THF cooled down to 0° C. was treated with lithium borohydride (9.0 mmol) and stirring was continued at 0° C. for 15 min. The reaction mixture was then let to warm up to room temperature and stirred for an additional 5 h. The reaction was quenched by addition of water, reaction volume was reduced in vacuo and diluted with ethylacetate. The organic phase was extracted with aqueous NaOH 1M, dried over $Na_2SO_4$ and evaporated to give a residue which was chromatographed on silica using a mixture of dichloromethane and a solution 10% $NH_4OH$ in MeOH as eluent to give 0.76 g of the (S)-3-amino-3-(2-fluoro-5-nitro-phenyl)-pentan-1-ol. MS (ESI): m/z=243.0 [M+H]$^+$.

Procedure for intermediate Da3 ($R^{1,2}$=cyclopropyl, $R^3$=Me): A solution of the hydrochloride of 1-[(S)-1-amino-1-(2-fluoro-5-nitro-phenyl)-ethyl]-cyclopropanecarboxylic acid (1.8 g) in THF (10 ml) was cooled to 0° C. and treated with a solution of BH3-THF complex in THF (1M, 22.7 ml) and stirring was continued at 0° C. for 3 h. The reaction mixture was pored into crashed ice/saturated aqueous NaHCO3 (1/1, 200 ml), extracted with ethyl acetate, the organic layer was dried and evaporated to give crude {1-[(S)-1-amino-1-(2-fluoro-5-nitro-phenyl)-ethyl]-cyclopropyl}-methanol as a pale yellow solid. MS (ESI): m/z=255.2 [M+H]$^+$.

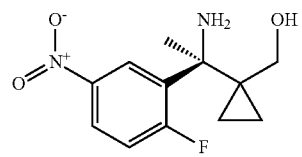

E. Synthesis of the intermediate amino oxazine E

General Procedure

To a solution of the amino alcohol D (5.4 mmol) in 30 mL dry THF was added bromocyanogen (6.2 mmol), sodium acetate (6.2 mmol) and the resulting reaction mixture was stirred at 80° C. overnight. The reaction mixture was let to cool down to room temperature, followed by addition of HCl 4.0M in Dioxane (10 mL) and stirred for 20 min. The reaction volume reduced in vacuo, diluted with ethyl acetate and partitioned with aq. Na2CO3 2M solution. The organic layer was dried and evaporated down to dryness to give a residue which was chromatographed on silica using a mixture of heptane and ethyl acetate as eluent to afford pure amino oxazine E.

Intermediate E1 ($R^3$=Me): Starting from (S)-3-amino-3-(2-fluoro-5-nitro-phenyl)-butan-1-ol (5 mmol), the product (S)-4-(2-fluoro-5-nitro-phenyl)-4-methyl-5,6-dihydro-4H-[1,3]oxazin-2-ylamine (1.04 g) was obtained as a pale yellow solid. MS (ESI): m/z=254.0 [M+H]$^+$.

Intermediate E2 ($R^3$=Et): Starting from (S)-3-amino-3-(2-fluoro-5-nitro-phenyl)-pentan-1-ol (2 mmol), the product (S)-4-ethyl-4-(2-fluoro-5-nitro-phenyl)-5,6-dihydro-4H-[1,3]oxazin-2-ylamine (0.253 g) was obtained as a pale yellow solid. MS (ESI): m/z=268.1 [M+H]$^+$.

Intermediate Ea3 ($R^{1,2}$=cyclopropyl, $R^3$=Me): To a solution of {1-[(S)-1-amino-1-(2-fluoro-5-nitro-phenyl)-ethyl]-cyclopropyl}-methanol (0.50 g) in dry THF (20 ml) was added bromocyanogen (0.24 g) and sodium acetate (0.19 g) and the mixture was stirred at 80° C. overnight. The mixture was cooled to 22° C., diluted with HCl in dioxane (4M, 2.4 ml) and stirring was continued for 1 h. The mixture was partitioned between aqueous saturated Na2CO3 and ethyl acetate, the organic layer was dried, evaporated and the residue purified by chromatography over silca-NH2 using ethyl acetate to give (S)-8-(2-fluoro-5-nitro-phenyl)-8-methyl-5-oxa-7-aza-spiro[2.5]oct-6-en-6-ylamine (0.30 g) as a pale yellow solid. MS (ESI): m/z=280.1 [M+H]$^+$.

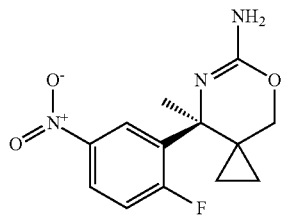

F. Synthesis of the intermediate Boc-protected amino oxazine F

General Procedure

To a solution of the amino oxazine E (1.7 mmol) in 25 mL dry THF was added di-tert-butyl dicarbonate (2.0 mmol), diisopropylethylamine (2.0 mmol) and the resulting reaction mixture was stirred at 40° C. overnight. The reaction mixture was let to cool down to room temperature and the reaction mixture was concentrated in vacuo to give a white foam. The residue was chromatographed on silica using a mixture of heptane and ethyl acetate as eluent to give pure Boc-protected amino oxazine F.

Intermediate F1 ($R^3$=Me): Starting from (S)-4-(2-fluoro-5-nitro-phenyl)-4-methyl-5,6-dihydro-4H-[1,3]oxazin-2-ylamine (2 mmol), the product [(S)-4-(2-fluoro-5-nitro-phenyl)-4-methyl-5,6-dihydro-4H-[1,3]oxazin-2-yl]-carbamic acid tert-butyl ester (0.473 g) was obtained as a pale yellow solid. MS (ESI): m/z=354.1 [M+H]$^+$.

Intermediate F2 ($R^3$=Et): Starting from (S)-4-ethyl-4-(2-fluoro-5-nitro-phenyl)-5,6-dihydro-4H-[1,3]oxazin-2-ylamine (1 mmol), the product [(S)-4-ethyl-4-(2-fluoro-5-nitro-phenyl)-5,6-dihydro-4H-[1,3]oxazin-2-yl]-carbamic acid tert-butyl ester (0.296 g) was obtained as a pale yellow solid. MS (ESI): m/z=368.1 [M+H]$^+$.

F. Synthesis of the intermediate aniline Fa

Intermediate Fa3 ($R^{1,2}$=cyclopropyl, $R^3$=Me): A suspension of (S)-8-(2-fluoro-5-nitro-phenyl)-8-methyl-5-oxa-7-aza-spiro[2.5]oct-6-en-6-ylamine (279 mg) in ethyl alcohol (25 ml), NEt3 (0.10 ml) and Pd/C (10%, 50 mg) was hydrogenated at normal pressure and 22° C. for 1 h. The mixture was filtered, the filtrate evaporated and the residue triturated with ether to give (S)-8-(5-amino-2-fluoro-phenyl)-8-methyl-5-oxa-7-aza-spiro[2.5]oct-6-en-6-ylamine (213 mg) as a pale yellow solid. MS (ESI): m/z=250.1 [M+H]$^+$.

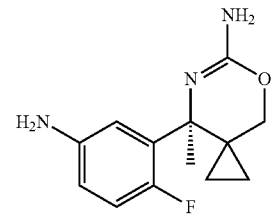

Synthesis of the intermediate anilines G

General Procedure

A suspension of the Boc-protected amino oxazine F (3.3 mmol) in ethanol (100 ml) and Pd/C (10%, 100 mg) was hydrogenated at normal pressure and 22° C. for 2 h. The mixture was filtered on dicalite, the filtrate evaporated and the residue was chromatographed on silica using a mixture of dichloromethane and methanol as eluent to give the pure aniline F.

Intermediate G1 ($R^3$=Me): Starting from [(S)-4-(2-fluoro-5-nitro-phenyl)-4-methyl-5,6-dihydro-4H-[1,3]oxazin-2-yl]-carbamic acid tert-butyl ester (1.34 mmol), the product [(S)-4-(5-amino-2-fluoro-phenyl)-4-methyl-5,6-dihydro-4H-[1,3]oxazin-2-yl]-carbamic acid tert-butyl ester 0.43 g) was obtained as a pale yellow solid. MS (ESI): m/z=324.5 [M+H]$^+$.

Intermediate G ($R^3$=Et): Starting from [(S)-4-ethyl-4-(2-fluoro-5-nitro-phenyl)-5,6-dihydro-4H-[1,3]oxazin-2-yl]-carbamic acid tert-butyl ester (0.8 mmol), the product [(S)-4-(5-Amino-2-fluoro-phenyl)-4-ethyl-5,6-dihydro-4H-[1,3]oxazin-2-yl]-carbamic acid tert-butyl ester (0.247 g) was obtained as a pale yellow solid. MS (ESI): m/z=338.2 [M+H]$^+$.

Synthesis of the amides H and I

General Procedure

To a solution of the aniline G (0.32 mmol) in dry dichloromethane (5 ml) was added subsequently EDCI (0.35 mmol), the carboxylic acid (0.35 mmol) and stirring was continued at 22° C. for 16 h. The mixture was purified on prep. RP-18 HPLC using a gradient of acetonitrile and water (containing 0.1% of triethylamine) to give the t-butyloxycarbonyl protected intermediate H.

A solution of t-butyloxycarbonyl protected intermediate H (0.27 mmol) in 4.0 ml dry dichloromethane was added CF3COOH (1 ml) and stirring was continued at 22° C. for 90 min. The mixture was evaporated, the residue was dissolved in DMSO and purified by prep. RP-18 HPLC using a gradient of acetonitrile and water (containing 0.1% of triethylamine) to give the pure amide I in yields of 10-70%.

General procedure for the coupling of the intermediate aniline Fa and a carboxylic acid to give the final product I To a solution of the carboxylic acid (0.12 mmole) in methanol (0.6 ml) was added at 0° C. 4-(4,6-dimethoxy-1,3,5-triazin-2-yl)-4-methyl-morpholinium chloride (0.12 mmole) and the solution was stirred for 60 min. The mixture was treated with the aniline Fa (0.12 mmole) and stirring was continued at 0° C. for 24 h. The mixture was evaporated and the residue partitioned between aqueous saturated $Na_2CO_3$ and ethyl acetate, the organic layer was dried and evaporated and the residue purified on prep. RP-18 HPLC using a gradient of acetonitrile and water (containing 0.1% of triethylamine) or $NH_2$-silica using ethyl actetate/n-heptane to give the pure final product I.

Example 1

3,5-Dichloro-pyridine-2-carboxylic acid [3-((S)-2-amino-4-methyl-5,6-dihydro-4H-[1,3]oxazin-4-yl)-4-fluoro-phenyl]-amide

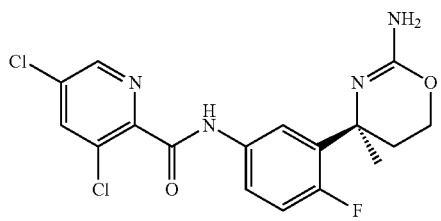

The coupling of [(S)-4-(5-amino-2-fluoro-phenyl)-4-methyl-5,6-dihydro-4H-[1,3]oxazin-2-yl]-carbamic acid tert-butyl ester from experiment F1 ($R^3$=Me) and 3,5-dichloro-pyridine-2-carboxylic acid followed by deprotection using procedure H yielded the title compound.

MS (ESI): m/z=398.1 $[M+H]^+$.

Example 2

5-Chloro-pyridine-2-carboxylic acid [3-((S)-2-amino-4-methyl-5,6-dihydro-4H-[1,3]oxazin-4-yl)-4-fluoro-phenyl]-amide

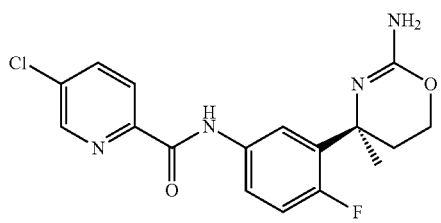

The coupling of [(S)-4-(5-amino-2-fluoro-phenyl)-4-methyl-5,6-dihydro-4H-[1,3]oxazin-2-yl]-carbamic acid tert-butyl ester from experiment F1 ($R^3$=Me) and 5-chloro-pyridine-2-carboxylic acid followed by deprotection using procedure H yielded the title compound. MS (ESI): m/z=363.1 $[M+H]^+$.

Example 3

5-Fluoro-pyridine-2-carboxylic acid [3-((S)-2-amino-4-methyl-5,6-dihydro-4H-[1,3]oxazin-4-yl)-4-fluoro-phenyl]-amide

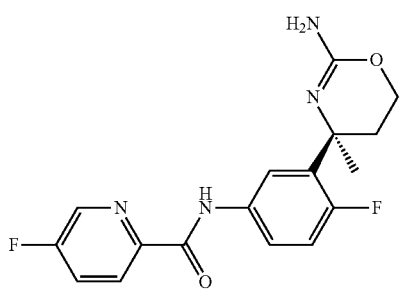

The coupling of [(S)-4-(5-amino-2-fluoro-phenyl)-4-methyl-5,6-dihydro-4H-[1,3]oxazin-2-yl]-carbamic acid tert-butyl ester from experiment F1 ($R^3$=Me) and 5-fluoro-pyridine-2-carboxylic acid followed by deprotection using procedure H yielded the title compound. MS (ESI): m/z=347.0 $[M+H]^+$.

Example 4

Pyridine-2-carboxylic acid [3-((S)-2-amino-4-methyl-5,6-dihydro-4H-[1,3]oxazin-4-yl)-4-fluoro-phenyl]-amide

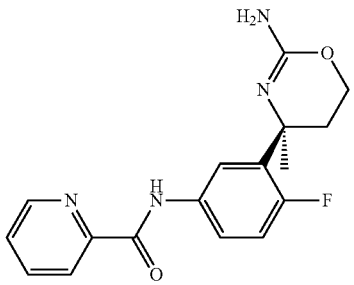

The coupling of [(S)-4-(5-amino-2-fluoro-phenyl)-4-methyl-5,6-dihydro-4H-[1,3]oxazin-2-yl]-carbamic acid tert-butyl ester from experiment F1 ($R^3$=Me) and pyridine-2-carboxylic acid followed by deprotection using procedure H yielded the title compound. MS (ESI): m/z=329.0 $[M+H]^+$.

Example 5

5-Trifluoromethyl-pyridine-2-carboxylic acid [3-((S)-2-amino-4-methyl-5,6-dihydro-4H-[1,3]oxazin-4-yl)-4-fluoro-phenyl]-amide

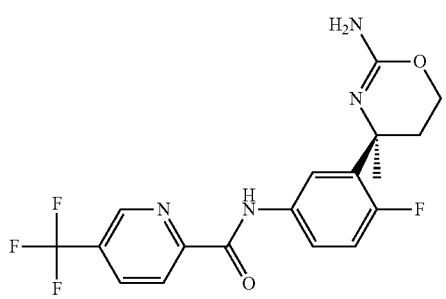

The coupling of [(S)-4-(5-amino-2-fluoro-phenyl)-4-methyl-5,6-dihydro-4H-[1,3]oxazin-2-yl]-carbamic acid tert-butyl ester from experiment F1 ($R^3$=Me) and 5-trifluoromethyl-pyridine-2-carboxylic acid followed by deprotection using procedure H yielded the title compound.

MS (ESI): m/z=397.0 [M+H]$^+$.

Example 6

3-Fluoro-pyridine-2-carboxylic acid [3-((S)-2-amino-4-methyl-5,6-dihydro-4H-[1,3]oxazin-4-yl)-4-fluoro-phenyl]-amide

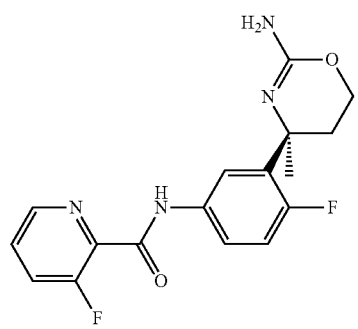

The coupling of [(S)-4-(5-amino-2-fluoro-phenyl)-4-methyl-5,6-dihydro-4H-[1,3]oxazin-2-yl]-carbamic acid tert-butyl ester from experiment F ($R^3$=Me) and 3-fluoro-pyridine-2-carboxylic acid followed by deprotection using procedure H yielded the title compound.

MS (ESI): m/z=347.1.0 [M+H]$^+$.

Example 7

5-Fluoro-thiophene-2-carboxylic acid [3-((S)-2-amino-4-methyl-5,6-dihydro-4H-[1,3]oxazin-4-yl)-4-fluoro-phenyl]-amide

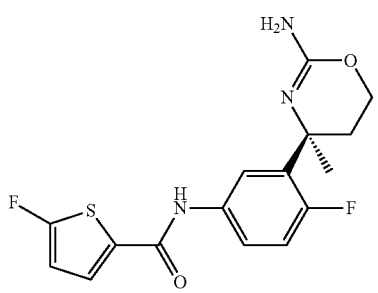

The coupling of [(S)-4-(5-amino-2-fluoro-phenyl)-4-methyl-5,6-dihydro-4H-[1,3]oxazin-2-yl]-carbamic acid tert-butyl ester from experiment F1 ($R^3$=Me) and 5-fluoro-thiophene-2-carboxylic acid followed by deprotection using procedure H yielded the title compound. MS (ESI): m/z=352.0 [M+H]$^+$.

Example 8

2-Methyl-oxazole-4-carboxylic acid [3-(S)-2-amino-4-methyl-5,6-dihydro-4H-[1,3]oxazin-4-yl)-4-fluoro-phenyl]-amide

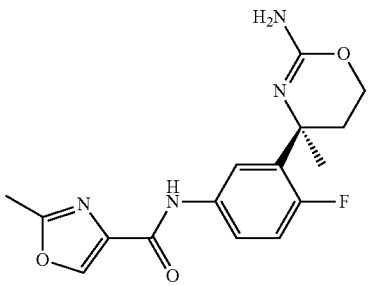

The coupling of [(S)-4-(5-amino-2-fluoro-phenyl)-4-methyl-5,6-dihydro-4H-[1,3]oxazin-2-yl]-carbamic acid tert-butyl ester from experiment F1 ($R^3$=Me) and 2-methyl-oxazole-4-carboxylic acid followed by deprotection using procedure H yielded the title compound. MS (ESI): m/z=333.0 [M+H]$^+$.

Example 9

4-Chloro-pyridine-2-carboxylic acid [3-(S)-2-amino-4-methyl-5,6-dihydro-4H-[1,3]oxazin-4-yl)-4-fluoro-phenyl]-amide

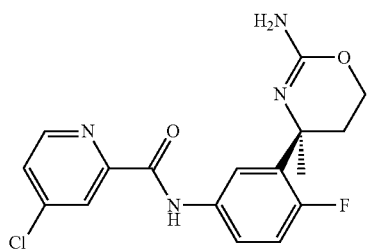

The coupling of [(S)-4-(5-amino-2-fluoro-phenyl)-4-methyl-5,6-dihydro-4H-[1,3]oxazin-2-yl]-carbamic acid tert-butyl ester from experiment F1 ($R^3$=Me) and 4-chloro-pyridine-2-carboxylic acid followed by deprotection using procedure H yielded the title compound.

MS (ESI): m/z=363.1 [M+H]$^+$.

Example 10

5-Chloro-thiophene-2-carboxylic acid [3-((S)-2-amino-4-methyl-5,6-dihydro-4H-[1,3]oxazin-4-yl)-4-fluoro-phenyl]-amide

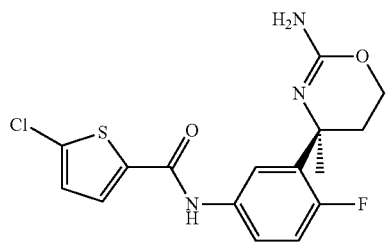

The coupling of [(S)-4-(5-amino-2-fluoro-phenyl)-4-methyl-5,6-dihydro-4H-[1,3]oxazin-2-yl]-carbamic acid tert-butyl ester from experiment F ($R^3$=Me) and 5-chloro-thiophene-2-carboxylic acid followed by deprotection using procedure H yielded the title compound.

MS (ESI): m/z=368.0 [M+H]$^+$.

Example 11

Thieno[2,3-c]pyridine-7-carboxylic acid [3-((S)-2-amino-4-methyl-5,6-dihydro-4H-[1,3]oxazin-4-yl)-4-fluoro-phenyl]-amide

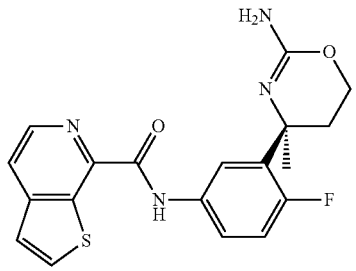

The coupling of [(S)-4-(5-amino-2-fluoro-phenyl)-4-methyl-5,6-dihydro-4H-[1,3]oxazin-2-yl]-carbamic acid tert-butyl ester from experiment F ($R^3$=Me) and thieno[2,3-c]pyridine-7-carboxylic acid followed by deprotection using procedure H yielded the title compound.

MS (ESI): m/z=385.0 [M+H]$^+$.

Example 12

3-Phenyl-pyridine-2-carboxylic acid [3-((S)-2-amino-4-methyl-5,6-dihydro-4H-[1,3]oxazin-4-yl)-4-fluoro-phenyl]-amide

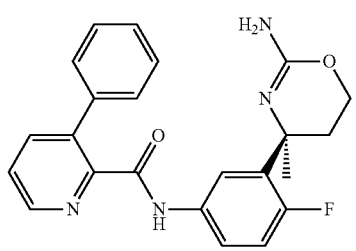

The coupling of [(S)-4-(5-amino-2-fluoro-phenyl)-4-methyl-5,6-dihydro-4H-[1,3]oxazin-2-yl]-carbamic acid tert-butyl ester from experiment F1 ($R^3$=Me) and 3-phenyl-pyridine-2-carboxylic acid followed by deprotection using procedure H yielded the title compound.

MS (ESI): m/z=405.0 [M+H]$^+$.

Example 13

Benzo[b]thiophene-2-carboxylic acid [3-((S)-2-amino-4-methyl-5,6-dihydro-4H-[1,3]oxazin-4-yl)-4-fluoro-phenyl]-amide

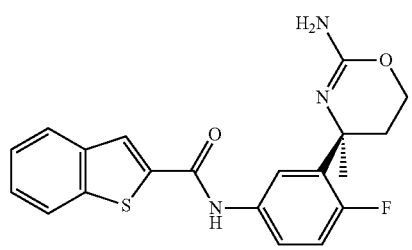

The coupling of [(S)-4-(5-amino-2-fluoro-phenyl)-4-methyl-5,6-dihydro-4H-[1,3]oxazin-2-yl]-carbamic acid tert-butyl ester from experiment F1 ($R^3$=Me) and benzo[b]thiophene-2-carboxylic acid followed by deprotection using procedure H yielded the title compound.

MS (ESI): m/z=384.1 [M+H]$^+$.

Example 14

5-Chloro-pyrazine-2-carboxylic acid [3-(S)-2-amino-4-methyl-5,6-dihydro-4H-[1,3]oxazin-4-yl)-4-fluoro-phenyl]-amide

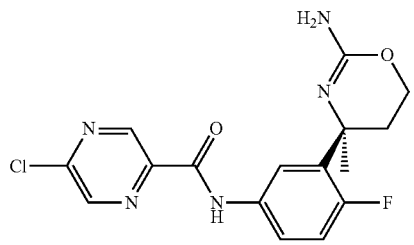

The coupling of [(S)-4-(5-amino-2-fluoro-phenyl)-4-methyl-5,6-dihydro-4H-[1,3]oxazin-2-yl]-carbamic acid tert-butyl ester from experiment F1 ($R^3$=Me) and 5-chloro-pyrazine-2-carboxylic acid followed by deprotection using procedure H yielded the title compound.

MS (ESI): m/z=364.0 [M+H]$^+$.

Example 15

5-Methyl-pyridine-2-carboxylic acid [3-(S)-2-amino-4-methyl-5,6-dihydro-4H-[1,3]oxazin-4-yl)-4-fluoro-phenyl]-amide

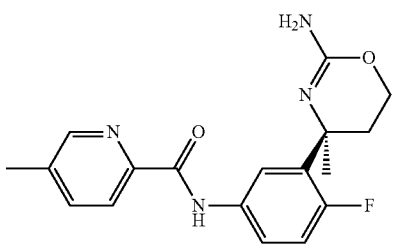

The coupling of [(S)-4-(5-amino-2-fluoro-phenyl)-4-methyl-5,6-dihydro-4H-[1,3]oxazin-2-yl]-carbamic acid tert-butyl ester from experiment F1 ($R^3$=Me) and 5-methyl-pyridine-2-carboxylic acid followed by deprotection using procedure H yielded the title compound.

MS (ESI): m/z=343.1 [M+H]$^+$.

Example 16

3-Trifluoromethyl-pyridine-2-carboxylic acid [3-((S)-2-amino-4-methyl-5,6-dihydro-4H-[1,3]oxazin-4-yl)-4-fluoro-phenyl]-amide

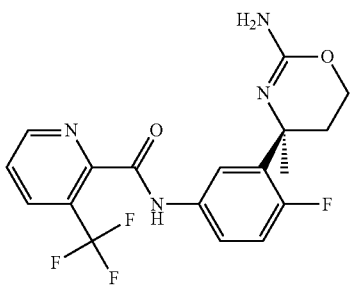

The coupling of [(S)-4-(5-amino-2-fluoro-phenyl)-4-methyl-5,6-dihydro-4H-[1,3]oxazin-2-yl]-carbamic acid tert-butyl ester from experiment F1 ($R^3$=Me) and 3-trifluoromethyl-pyridine-2-carboxylic acid followed by deprotection using procedure H yielded the title compound. MS (ESI): m/z=397.0 [M+H]$^+$.

Example 17

5-Methyl-thiophene-2-carboxylic acid [3-((S)-2-amino-4-methyl-5,6-dihydro-4H-[1,3]oxazin-4-yl)-4-fluoro-phenyl]-amide

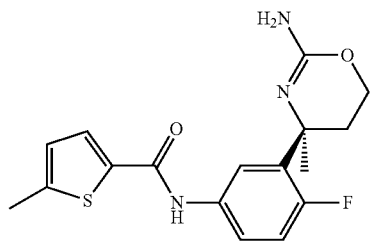

The coupling of [(S)-4-(5-amino-2-fluoro-phenyl)-4-methyl-5,6-dihydro-4H-[1,3]oxazin-2-yl]-carbamic acid tert-butyl ester from experiment F1 ($R^3$=Me) and 5-methyl-thiophene-2-carboxylic acid followed by deprotection using procedure H yielded the title compound.
MS (ESI): m/z=348.1.0 [M+H]$^+$.

Example 18 Pyridine-2-carboxylic acid [3-((S)-2-amino-4-ethyl-5,6-dihydro-4H-[1,3]oxazin-4-yl)-4-fluoro-phenyl]-amide

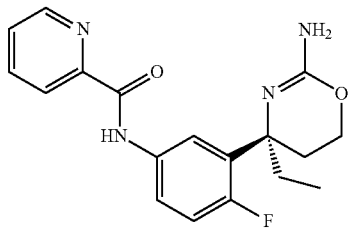

The coupling of [(S)-4-(5-amino-2-fluoro-phenyl)-4-ethyl-5,6-dihydro-4H-[1,3]oxazin-2-yl]-carbamic acid tert-butyl ester from experiment F2 ($R^3$=Et) and pyridine-2-carboxylic acid followed by deprotection using procedure H yielded the title compound.
MS (ESI): m/z=343.1 [M+H]$^+$.

Example 19

5-Chloro-pyridine-2-carboxylic acid [3-((S)-2-amino-4-ethyl-5,6-dihydro-4H-[1,3]oxazin-4-yl)-4-fluoro-phenyl]-amide

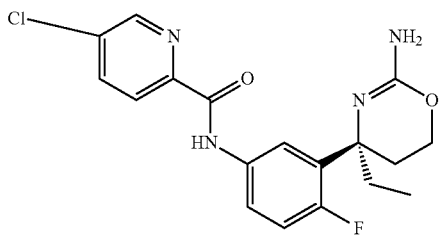

The coupling of [(S)-4-(5-amino-2-fluoro-phenyl)-4-ethyl-5,6-dihydro-4H-[1,3]oxazin-2-yl]-carbamic acid tert-butyl ester from experiment F2 ($R^3$=Et) and 5-chloro-pyridine-2-carboxylic acid followed by deprotection using procedure H yielded the title compound.
MS (ESI): m/z=377.0 [M+H]$^+$.

Example 20

5-Methyl-thiophene-2-carboxylic acid [3-(S)-2-amino-4-ethyl-5,6-dihydro-4H-[1,3]oxazin-4-yl)-4-fluoro-phenyl]-amide

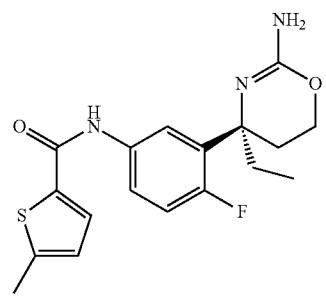

The coupling of [(S)-4-(5-amino-2-fluoro-phenyl)-4-ethyl-5,6-dihydro-4H-[1,3]oxazin-2-yl]-carbamic acid tert-butyl ester from experiment F2 ($R^3$=Et) and 5-methyl-thiophene-2-carboxylic acid followed by deprotection using procedure H yielded the title compound.
MS (ESI): m/z=362.0 [M+H]$^+$.

Example 21

5-Chloro-thiophene-2-carboxylic acid [3-(S)-2-amino-4-ethyl-5,6-dihydro-4H-[1,3]oxazin-4-yl)-4-fluoro-phenyl]-amide

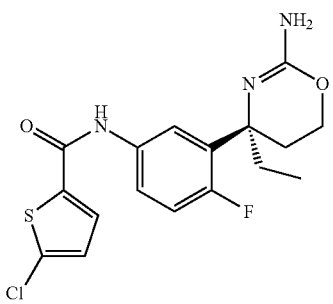

The coupling of [(S)-4-(5-amino-2-fluoro-phenyl)-4-ethyl-5,6-dihydro-4H-[1,3]oxazin-2-yl]-carbamic acid tert-butyl ester from experiment F2 ($R^3$=Et) and 5-chloro-thiophene-2-carboxylic acid followed by deprotection using procedure H yielded the title compound.
MS (ESI): m/z=382.1 [M+H]$^+$.

Example 22

3,5-Dichloro-pyridine-2-carboxylic acid [3-(S)-2-amino-4-ethyl-5,6-dihydro-4H-[1,3]oxazin-4-yl)-4-fluoro-phenyl]-amide

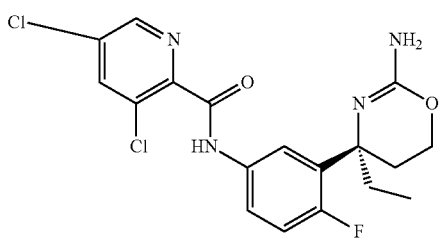

The coupling of [(S)-4-(5-amino-2-fluoro-phenyl)-4-ethyl-5,6-dihydro-4H-[1,3]oxazin-2-yl]-carbamic acid tert-butyl ester from experiment F2 ($R^3$=Et) and 3,5-Dichloro-pyridine-2-carboxylic acid followed by deprotection using procedure H yielded the title compound.

MS (ESI): m/z=411.0 [M+H]$^+$.

Example 23

5-Chloro-3-methyl-pyridine-2-carboxylic acid [3-(S)-2-amino-4-ethyl-5,6-dihydro-4H-[1,3]oxazin-4-yl)-4-fluoro-phenyl]-amide

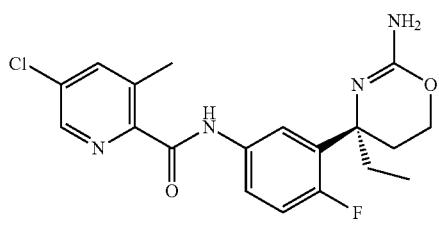

The coupling of [(S)-4-(5-amino-2-fluoro-phenyl)-4-ethyl-5,6-dihydro-4H-[1,3]oxazin-2-yl]-carbamic acid tert-butyl ester from experiment F2 ($R^3$=Et) and 5-chloro-3-methyl-pyridine-2-carboxylic acid followed by deprotection using procedure H yielded the title compound.

MS (ESI): m/z=391.1 [M+H]$^+$.

Example 24

2-Methyl-oxazole-4-carboxylic acid [3-(S)-2-amino-4-ethyl-5,6-dihydro-4H-[1,3]oxazin-4-yl)-4-fluoro-phenyl]-amide

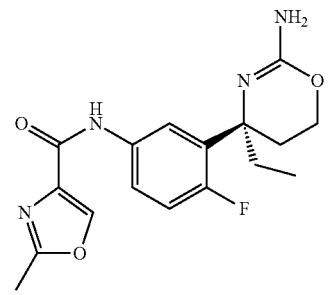

The coupling of [(S)-4-(5-amino-2-fluoro-phenyl)-4-ethyl-5,6-dihydro-4H-[1,3]oxazin-2-yl]-carbamic acid tert-butyl ester from experiment F2 ($R^3$=Et) and 2-methyl-oxazole-4-carboxylic acid followed by deprotection using procedure H yielded the title compound.

MS (ESI): m/z=347.0 [M+H]$^+$.

Example 25

5-Cyano-pyridine-2-carboxylic acid [3-(S)-2-amino-4-methyl-5,6-dihydro-4H-[1,3]oxazin-4-yl)-4-fluoro-phenyl]-amide

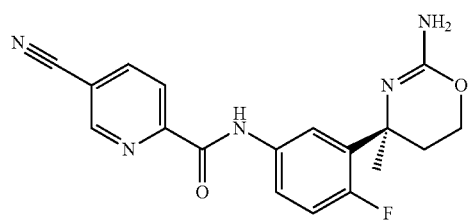

The coupling of [(S)-4-(5-amino-2-fluoro-phenyl)-4-methyl-5,6-dihydro-4H-[1,3]oxazin-2-yl]-carbamic acid tert-butyl ester from experiment F1 ($R^1$=Me) and 5-cyano-pyridine-2-carboxylic acid followed by deprotection using procedure H yielded the title compound.

MS (ESI): m/z=354.1 [M+H]$^+$.

Example 26

5-Chloro-3-methyl-pyridine-2-carboxylic acid [3-((S)-2-amino-4-methyl-5,6-dihydro-4H-[1,3]oxazin-4-yl)-4-fluoro-phenyl]-amide

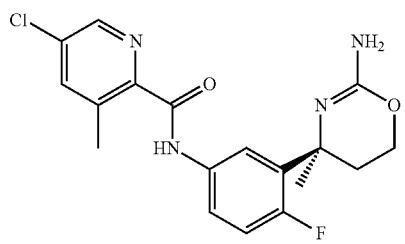

The coupling of [(S)-4-(5-amino-2-fluoro-phenyl)-4-methyl-5,6-dihydro-4H-[1,3]oxazin-2-yl]-carbamic acid tert-butyl ester from experiment F1 ($R^1$=Me) and 5-chloro-3-methyl-pyridine-2-carboxylic acid followed by deprotection using procedure H yielded the title compound. MS (ESI): m/z=377.0 [M+H]$^+$.

Example 27

3-Methoxy-pyridine-2-carboxylic acid [3-((S)-2-amino-4-methyl-5,6-dihydro-4H-[1,3]oxazin-4-yl)-4-fluoro-phenyl]-amide

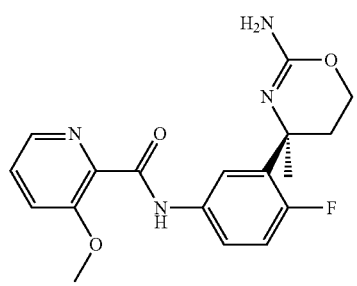

The coupling of [(S)-4-(5-amino-2-fluoro-phenyl)-4-methyl-5,6-dihydro-4H-[1,3]oxazin-2-yl]-carbamic acid tert-butyl ester from experiment F ($R^1$=Me) and 3-methoxy-pyridine-2-carboxylic acid followed by deprotection using procedure H yielded the title compound.
MS (ESI): m/z=359.0 [M+H]$^+$.

Example 28

2-Methyl-thiazole-4-carboxylic acid [3-(S)-2-amino-4-methyl-5,6-dihydro-4H-[1,3]oxazin-4-yl)-4-fluoro-phenyl]-amide

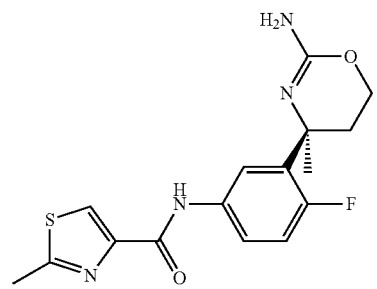

The coupling of [(S)-4-(5-amino-2-fluoro-phenyl)-4-methyl-5,6-dihydro-4H-[1,3]oxazin-2-yl]-carbamic acid tert-butyl ester from experiment F1 ($R^3$=Me) and 2-methyl-thiazole-4-carboxylic acid followed by deprotection using procedure H yielded the title compound.
MS (ESI): m/z=349.0 [M+H]$^+$.

Example 29

1-Methyl-1H-pyrazole-3-carboxylic acid [3-(S)-2-amino-4-methyl-5,6-dihydro-4H-[1,3]oxazin-4-yl)-4-fluoro-phenyl]-amide

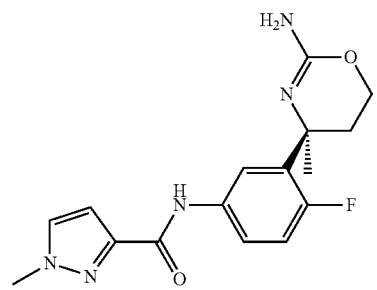

The coupling of [(S)-4-(5-amino-2-fluoro-phenyl)-4-methyl-5,6-dihydro-4H-[1,3]oxazin-2-yl]-carbamic acid tert-butyl ester from experiment F1 ($R^3$=Me) and 1-methyl-1H-pyrazole-3-carboxylic acid followed by deprotection using procedure H yielded the title compound.
MS (ESI): m/z=332.0 [M+H]$^+$.

Example 30

5-Methoxy-pyridine-2-carboxylic acid [3-((S)-2-amino-4-methyl-5,6-dihydro-4H-[1,3]oxazin-4-yl)-4-fluoro-phenyl]-amide

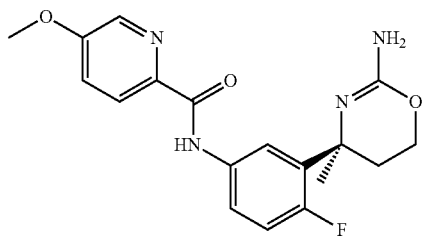

The coupling of [(S)-4-(5-amino-2-fluoro-phenyl)-4-methyl-5,6-dihydro-4H-[1,3]oxazin-2-yl]-carbamic acid tert-butyl ester from experiment F1 ($R^1$=Me) and 5-methoxy-pyridine-2-carboxylic acid followed by deprotection using procedure H yielded the title compound.

MS (ESI): m/z=359.0 [M+H]$^+$.

Example 31

3-Chloro-5-trifluoromethyl-pyridine-2-carboxylic acid [3-((S)-2-amino-4-methyl-5,6-dihydro-4H-[1,3]oxazin-4-yl)-4-fluoro-phenyl]-amide

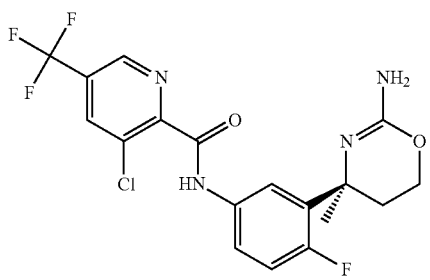

The coupling of [(S)-4-(5-amino-2-fluoro-phenyl)-4-methyl-5,6-dihydro-4H-[1,3]oxazin-2-yl]-carbamic acid tert-butyl ester from experiment F1 ($R^1$=Me) and 3-chloro-5-trifluoromethyl-pyridine-2-carboxylic acid followed by deprotection using procedure H yielded the title compound.

MS (ESI): m/z=431.0 [M+H]$^+$.

Example 32

6-Chloro-pyridine-2-carboxylic acid [3-((S)-2-amino-4-methyl-5,6-dihydro-4H-[1,3]oxazin-4-yl)-4-fluoro-phenyl]-amide

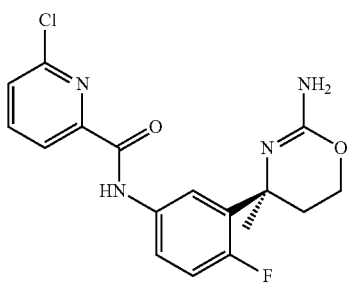

The coupling of [(S)-4-(5-amino-2-fluoro-phenyl)-4-methyl-5,6-dihydro-4H-[1,3]oxazin-2-yl]-carbamic acid tert-butyl ester from experiment F1 ($R^1$=Me) and 6-chloro-pyridine-2-carboxylic acid followed by deprotection using procedure H yielded the title compound.

MS (ESI): m/z=363.0 [M+H]$^+$.

Example 33

3,5-Difluoro-pyridine-2-carboxylic acid [3-((S)-2-amino-4-methyl-5,6-dihydro-4H-[1,3]oxazin-4-yl)-4-fluoro-phenyl]-amide

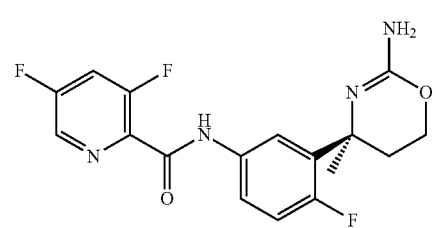

The coupling of [(S)-4-(5-amino-2-fluoro-phenyl)-4-methyl-5,6-dihydro-4H-[1,3]oxazin-2-yl]-carbamic acid tert-butyl ester from experiment F1 ($R^1$=Me) and 3,5-difluoro-pyridine-2-carboxylic acid followed by deprotection using procedure H yielded the title compound.

MS (ESI): m/z=365.0 [M+H]$^+$.

Example 34

3-Methyl-thiophene-2-carboxylic acid [3-(S)-2-amino-4-methyl-5,6-dihydro-4H-[1,3]oxazin-4-yl)-4-fluoro-phenyl]-amide

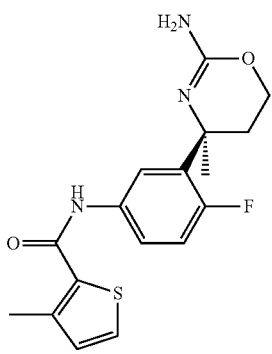

The coupling of [(S)-4-(5-amino-2-fluoro-phenyl)-4-methyl-5,6-dihydro-4H-[1,3]oxazin-2-yl]-carbamic acid tert-butyl ester from experiment F1 ($R^1$=Me) and 3-methyl-thiophene-2-carboxylic acid followed by deprotection using procedure H yielded the title compound.
MS (ESI): m/z=384.0 [M+H]$^+$.

Example 35

3-Chloro-5-fluoro-pyridine-2-carboxylic acid [3-(S)-2-amino-4-methyl-5,6-dihydro-4H-[1,3]oxazin-4-yl)-4-fluoro-phenyl]-amide

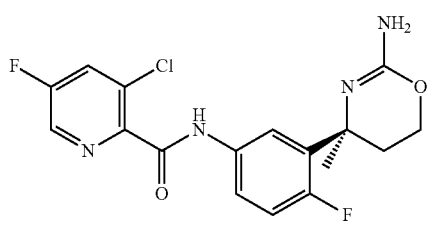

The coupling of [(S)-4-(5-amino-2-fluoro-phenyl)-4-methyl-5,6-dihydro-4H-[1,3]oxazin-2-yl]-carbamic acid tert-butyl ester from experiment F1 ($R^1$=Me) and 3-chloro-5-fluoro-pyridine-2-carboxylic acid followed by deprotection using procedure H yielded the title compound. MS (ESI): m/z=381.0 [M+H]$^+$.

Example 36

5-Chloro-pyridine-2-carboxylic acid [3-((S)-6-amino-8-methyl-5-oxa-7-aza-spiro[2.5]oct-6-en-8-yl)-4-fluoro-phenyl]-amide

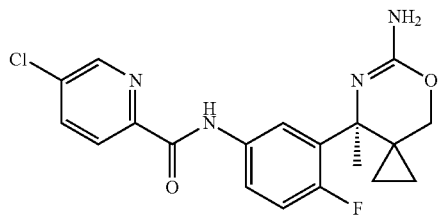

The coupling of (S)-8-(5-amino-2-fluoro-phenyl)-8-methyl-5-oxa-7-aza-spiro[2.5]oct-6-en-6-ylamine and 5-chloro-pyridine-2-carboxylic acid yielded the title compound as a white solid. MS (ESI): m/z=389.2 [M+H]$^+$.

Example 37

3-Fluoro-pyridine-2-carboxylic acid [3-((S)-6-amino-8-methyl-5-oxa-7-aza-spiro[2.5]oct-6-en-8-yl)-4-fluoro-phenyl]-amide

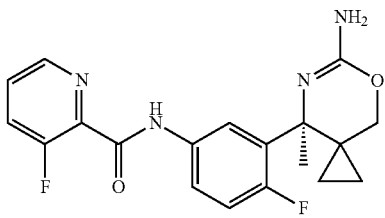

The coupling of (S)-8-(5-amino-2-fluoro-phenyl)-8-methyl-5-oxa-7-aza-spiro[2.5]oct-6-en-6-ylamine and 3-fluoro-pyridine-2-carboxylic acid yielded the title compound as a colorless solid. MS (ESI): m/z=373.2 [M+H]$^+$.

Example 38

5-Chloro-3-methyl-pyridine-2-carboxylic acid [3-((S)-6-amino-8-methyl-5-oxa-7-aza-Spiro[2.5]oct-6-en-8-yl)-4-fluoro-phenyl]amide

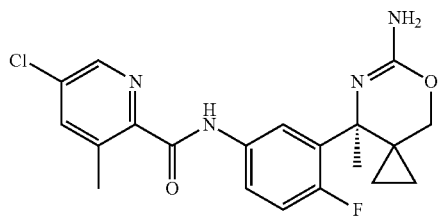

The coupling of (S)-8-(5-amino-2-fluoro-phenyl)-8-methyl-5-oxa-7-aza-spiro[2.5]oct-6-en-6-ylamine and 5-chloro-3-methyl-pyridine-2-carboxylic acid yielded the title compound as a colorless solid. MS (ESI): m/z=403.4 [M+H]⁺.

Example 39

5-Methoxy-pyridine-2-carboxylic acid [3-(S)-6-amino-8-methyl-5-oxa-7-aza-spiro[2.5]oct-6-en-8-yl)-4-fluoro-phenyl]-amide

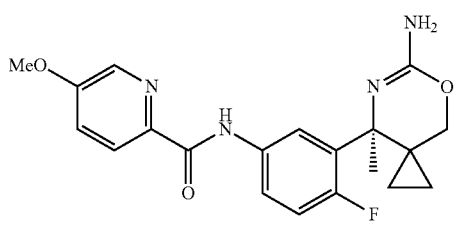

The coupling of (S)-8-(5-amino-2-fluoro-phenyl)-8-methyl-5-oxa-7-aza-spiro[2.5]oct-6-en-6-ylamine and 5-methoxy-pyridine-2-carboxylic acid yielded the title compound as a colorless oil. MS (ESI): m/z=385.3 [M+H]⁺.

Example 40

5-Fluoro-pyridine-2-carboxylic acid [3-((S)-6-amino-8-methyl-5-oxa-7-aza-spiro[2.5]oct-6-en-8-yl)-4-fluoro-phenyl]-amide

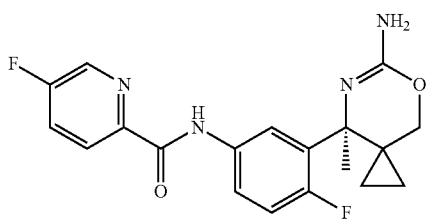

The coupling of (S)-8-(5-amino-2-fluoro-phenyl)-8-methyl-5-oxa-7-aza-spiro[2.5]oct-6-en-6-ylamine and 5-fluoro-pyridine-2-carboxylic acid yielded the title compound as a colorless oil. MS (ESI): m/z=373.2 [M+H]⁺.

Example 41

5-Cyano-pyridine-2-carboxylic acid [3-((S)-6-amino-8-methyl-5-oxa-7-aza-spiro[2.5]oct-6-en-8-yl)-4-fluoro-phenyl]-amide

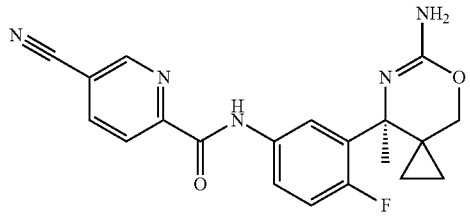

The coupling of (S)-8-(5-amino-2-fluoro-phenyl)-8-methyl-5-oxa-7-aza-spiro[2.5]oct-6-en-6-ylamine and 5-cyano-pyridine-2-carboxylic acid yielded the title compound as a colorless solid. MS (ESI): m/z=380.2 [M+H]⁺.

Example 42

5-Difluoromethoxy-pyridine-2-carboxylic acid [3-((S)-6-amino-8-methyl-5-oxa-7-aza-Spiro[2.5]oct-6-en-8-yl)-4-fluoro-phenyl]-amide

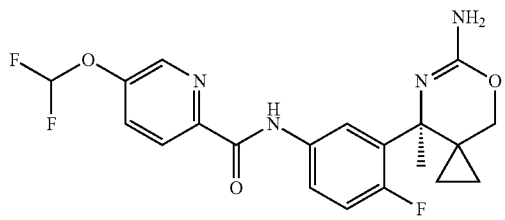

The coupling of (S)-8-(5-amino-2-fluoro-phenyl)-8-methyl-5-oxa-7-aza-spiro[2.5]oct-6-en-6-ylamine and 5-difluoromethoxy-pyridine-2-carboxylic acid (prepared according to Suzuki, Y. et al., Int. Patent Appl. WO2009091016) yielded the title compound as a colorless solid.

MS (ESI): m/z=421.1 [M+H]⁺.

Example 43 Pyridine-2-carboxylic acid [3-((S)-6-amino-8-methyl-5-oxa-7-aza-spiro[2.5]oct-6-en-8-yl)-4-fluoro-phenyl]-amide

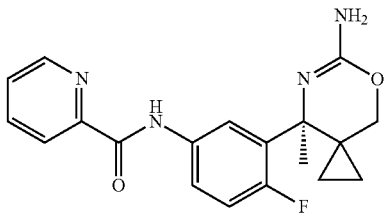

The coupling of (S)-8-(5-amino-2-fluoro-phenyl)-8-methyl-5-oxa-7-aza-spiro[2.5]oct-6-en-6-ylamine and pyridine-2-carboxylic acid yielded the title compound as a colorless solid.

MS (ESI): m/z=355.2 [M+H]⁺.

Example 44

5-Chloro-pyrimidine-2-carboxylic acid [3-((S)-6-amino-8-methyl-5-oxa-7-aza-spiro[2.5]oct-6-en-8-yl)-4-fluoro-phenyl]-amide

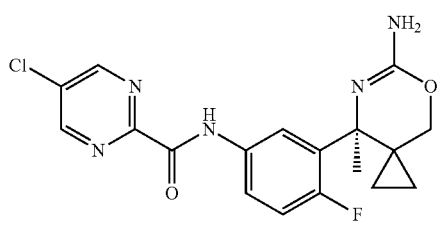

The coupling of (S)-8-(5-amino-2-fluoro-phenyl)-8-methyl-5-oxa-7-aza-spiro[2.5]oct-6-en-6-ylamine and 5-chloro-pyrimidine-2-carboxylic acid yielded the title compound as a colorless solid. MS (ESI): m/z=390.2 [M+H]⁺.

Example 45

N-[3-((S)-2-Amino-4-methyl-5,6-dihydro-4H-[1,3]oxazin-4-yl)-4-fluoro-phenyl]-2,3,3,3-tetrafluoro-propionamide

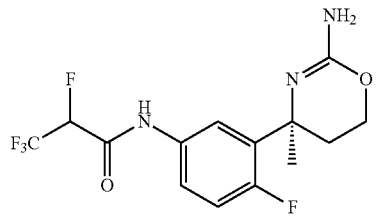

The coupling of (S)-4-(5-Amino-2-fluoro-phenyl)-4-methyl-5,6-dihydro-4H-[1,3]oxazin-2-ylamine and 2,3,3,3-tetrafluoro-propionic acid yielded the title compound as colorless solid.

MS (ESI): m/z=352.1 [M+H]⁺.

Example 46

2,2-Difluoro-cyclopropanecarboxylic acid [3-((S)-2-amino-4-methyl-5,6-dihydro-4H-[1,3]oxazin-4-yl)-4-fluoro-phenyl]-amide

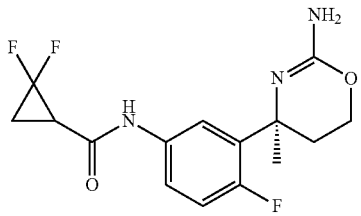

The coupling of (S)-4-(5-Amino-2-fluoro-phenyl)-4-methyl-5,6-dihydro-4H-[1,3]oxazin-2-ylamine and 2,2-difluoro-cyclopropanecarboxylic acid yielded the title compound as colorless solid. MS (ESI): m/z=328.2 [M+H]⁺.

Example 47

(S)—N-(3-(6-Amino-8-methyl-5-oxa-7-azaspiro[2.5]oct-6-en-8-yl)-4-fluorophenyl)-2,6-difluorobenzamide

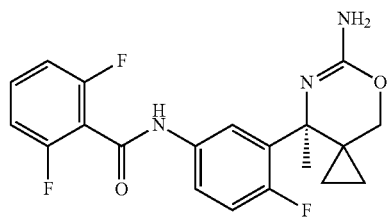

The coupling of (S)-8-(5-amino-2-fluoro-phenyl)-8-methyl-5-oxa-7-aza-spiro[2.5]oct-6-en-6-ylamine and 2,6-difluoro-benzoic acid yielded the title compound as a yellow solid.

MS (ESI): m/z=390.3 [M+H]⁺.

Example 48

(S)—N-(3-(6-Amino-8-methyl-5-oxa-7-azaspiro[2.5]oct-6-en-8-yl)-4-fluorophenyl)-3-chloropicolinamide

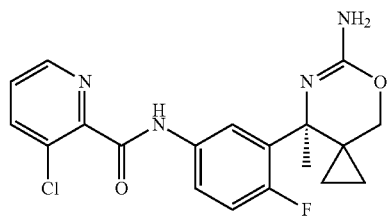

The coupling of (S)-8-(5-amino-2-fluoro-phenyl)-8-methyl-5-oxa-7-aza-spiro[2.5]oct-6-en-6-ylamine and 3-chloro-pyridine-2-carboxylic acid yielded the title compound as a yellow solid. MS (ESI): m/z=389.2 [M+H]⁺.

Example 49

(S)—N-(3-(6-Amino-8-methyl-5-oxa-7-azaspiro[2.5]oct-6-en-8-yl)-4-fluorophenyl)-3,5-difluoropicolinamide

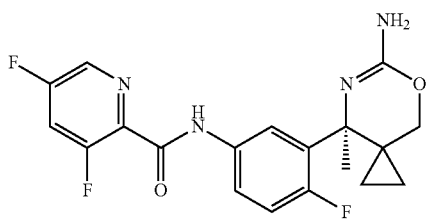

The coupling of (S)-8-(5-amino-2-fluoro-phenyl)-8-methyl-5-oxa-7-aza-spiro[2.5]oct-6-en-6-ylamine and 3,5-difluoro-pyridine-2-carboxylic acid yielded the title compound as a yellow solid. MS (ESI): m/z=391.3 [M+H]⁺.

Example 50

(S)—N-(3-(6-Amino-8-methyl-5-oxa-7-azaspiro[2.5]oct-6-en-8-yl)-4-fluorophenyl)-3-chloro-5-(trifluoromethyl)picolinamide

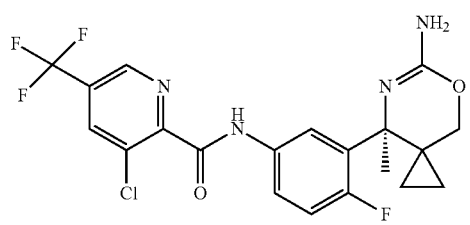

The coupling of (S)-8-(5-amino-2-fluoro-phenyl)-8-methyl-5-oxa-7-aza-spiro[2.5]oct-6-en-6-ylamine and 3-chloro-5-trifluoromethyl-pyridine-2-carboxylic acid yielded the title compound as a yellow solid. MS (ESI): m/z=457.3 [M+H]⁺.

Example 51

(S)—N-(3-(6-Amino-8-methyl-5-oxa-7-azaspiro[2.5]oct-6-en-8-yl)-4-fluorophenyl)-3-(trifluoromethyl)picolinamide

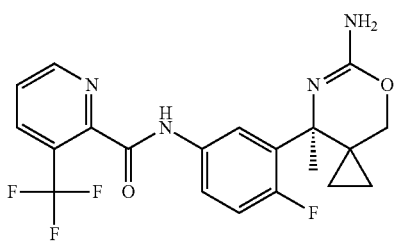

The coupling of (S)-8-(5-amino-2-fluoro-phenyl)-8-methyl-5-oxa-7-aza-spiro[2.5]oct-6-en-6-ylamine and 3-trifluoromethyl-pyridine-2-carboxylic acid yielded the title compound as a yellow solid. MS (ESI): m/z=423.2 [M+H]⁺.

Example 52

(S)—N-(3-(6-Amino-8-methyl-5-oxa-7-azaspiro[2.5]oct-6-en-8-yl)-4-fluorophenyl)-3-chloro-5-fluoropicolinamide

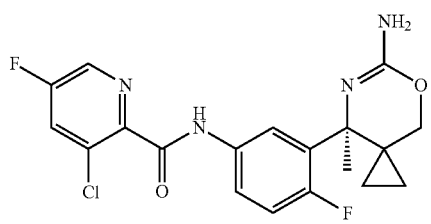

The coupling of (S)-8-(5-amino-2-fluoro-phenyl)-8-methyl-5-oxa-7-aza-spiro[2.5]oct-6-en-6-ylamine and 3-chloro-5-fluoro-pyridine-2-carboxylic acid yielded the title compound as a yellow solid. MS (ESI): m/z=407.3 [M+H]⁺.

Example 53

(S)—N-(3-(6-Amino-8-methyl-5-oxa-7-azaspiro[2.5]oct-6-en-8-yl)-4-fluorophenyl)-3,5-dichloropicolinamide

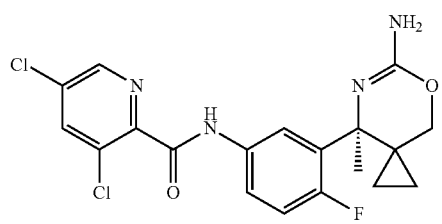

The coupling of (S)-8-(5-amino-2-fluoro-phenyl)-8-methyl-5-oxa-7-aza-spiro[2.5]oct-6-en-6-ylamine and 3,5-dichloro-pyridine-2-carboxylic acid yielded the title compound as a pale yellow solid. MS (ESI): m/z=423.1 [M+H]⁺.

Example 54

(S)—N-(3-(6-Amino-8-methyl-5-oxa-7-azaspiro[2.5]oct-6-en-8-yl)-4-fluorophenyl)-1-(trifluoromethyl)cyclopropanecarboxamide

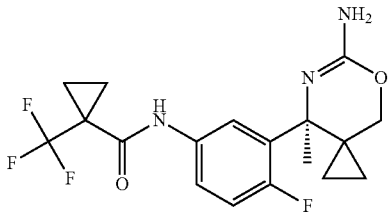

The coupling of (S)-8-(5-amino-2-fluoro-phenyl)-8-methyl-5-oxa-7-aza-spiro[2.5]oct-6-en-6-ylamine and 1-trifluoromethyl-cyclopropanecarboxylic acid yielded the title compound as a pale yellow solid. MS (ESI): m/z=386.4 [M+H]$^+$.

Example 55

N-(3-((S)-6-Amino-8-methyl-5-oxa-7-azaspiro[2.5]oct-6-en-8-yl)-4-fluorophenyl)-2,2-difluorocyclopropanecarboxamide

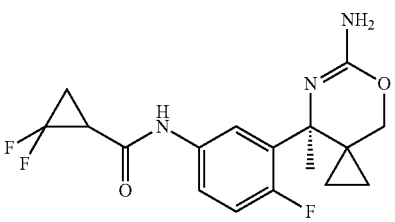

The coupling of (S)-8-(5-amino-2-fluoro-phenyl)-8-methyl-5-oxa-7-aza-spiro[2.5]oct-6-en-6-ylamine and rac-2,2-difluoro-cyclopropanecarboxylic acid yielded a mixture of epimers of the title compound as a yellow solid. MS (ESI): m/z=354.2 [M+H]$^+$.

Example 56

(S)—N-(3-(6-Amino-8-methyl-5-oxa-7-azaspiro[2.5]oct-6-en-8-yl)-4-fluorophenyl)-4-chloro-1-methyl-1H-pyrazole-3-carboxamide

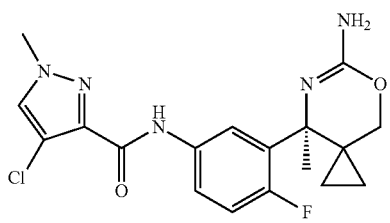

The coupling of (S)-8-(5-amino-2-fluoro-phenyl)-8-methyl-5-oxa-7-aza-spiro[2.5]oct-6-en-6-ylamine and 4-chloro-1-methyl-1H-pyrazole-3-carboxylic acid yielded the title compound as a yellow solid. MS (ESI): m/z=392.2 [M+H]$^+$.

Example 57

(S)—N-(3-(6-Amino-8-methyl-5-oxa-7-azaspiro[2.5]oct-6-en-8-yl)-4-fluorophenyl)-5-chloro-4-methylisoxazole-3-carboxamide

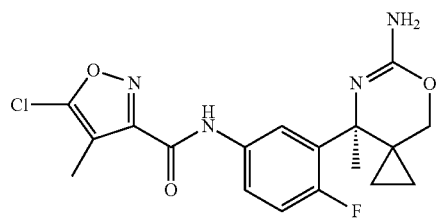

The coupling of (S)-8-(5-amino-2-fluoro-phenyl)-8-methyl-5-oxa-7-aza-spiro[2.5]oct-6-en-6-ylamine and 5-chloro-4-methyl-isoxazole-3-carboxylic acid yielded the title compound as a pale yellow solid. MS (ESI): m/z=393.2 [M+H]$^+$.

Example 58

1-Trifluoromethyl-cyclopropanecarboxylic acid [3-((S)-2-amino-4-methyl-5,6-dihydro-4H-[1,3]oxazin-4-yl)-4-fluoro-phenyl]-amide

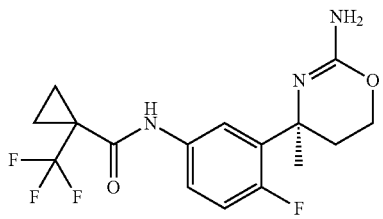

The coupling of (S)-4-(5-Amino-2-fluoro-phenyl)-4-methyl-5,6-dihydro-4H-[1,3]oxazin-2-ylamine and 1-trifluoromethyl-cyclopropanecarboxylic acid yielded the title compound as colorless solid. MS (ESI): m/z=360.1 [M+H]$^+$.

Example 59

N-[3-((S)-2-Amino-4-methyl-5,6-dihydro-4H-[1,3]oxazin-4-yl)-4-fluoro-phenyl]-3,3,3-trifluoro-propionamide

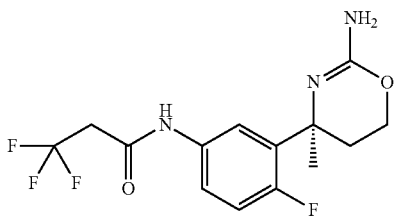

The coupling of (S)-4-(5-Amino-2-fluoro-phenyl)-4-methyl-5,6-dihydro-4H-[1,3]oxazin-2-ylamine and 3,3,3-trifluoro-propionic acid yielded the title compound as colorless solid. MS (ESI): m/z=334.3 [M+H]$^+$.

Example 60

(S)—N-(3-(2-Amino-4-methyl-5,6-dihydro-4H-1,3-oxazin-4-yl)-4-fluorophenyl)-3-(2,2,2-trifluoroethoxy)picolinamide

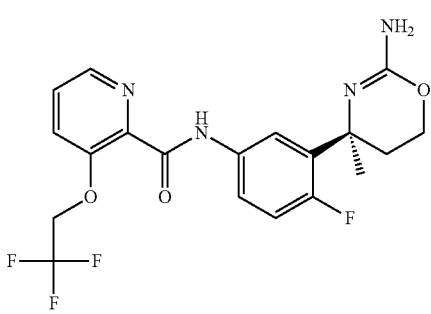

The 3-(2,2,2-trifluoro-ethoxy)-pyridine-2-carboxylic acid was prepared as follows:

a) To a solution of 3-hydroxy-pyridine-2-carboxylic acid methyl ester (200 mg, 1.3 mmol) in N,N-dimethylformamide (2.0 ml) was added at 22° C. sodium hydride (55% in oil, 64 mg) and stirring was continued until gas evolution ceased. The suspension was cooled to 0° C. and treated with trifluoroethyl trifluormethanesulfonate (728 mg) and stirring was continued at 22° C. for 2 hours. The mixture was partitioned between saturated sodium hydrogen-carbonate solution and ethyl acetate, and the organic layer was dried and evaporated. The residue was purified by chromatography on silica using n-heptane and ethyl acetate (3:1) as the eluent to give 3-(2,2,2-trifluoro-ethoxy)-pyridine-2-carboxylic acid methyl ester as a pale green oil. MS (ESI): m/z=236.2 [M+H]$^+$.

b) A solution of 3-(2,2,2-trifluoro-ethoxy)-pyridine-2-carboxylic acid methyl ester (216 mg, 0.9 mmol) in methanol (1 ml) was treated with a solution of lithium hydroxide (78 mg, 3.3 mmol) in water (0.1 ml) and stirring was continued at 22° C. for 2 hours. The solution was evaporated and the residue triturated with 1N aqueous hydrochloric acid. The suspension was filtered, the residue washed with water and dried to give 3-(2,2,2-trifluoro-ethoxy)-pyridine-2-carboxylic acid as a colorless solid. MS (ESI): m/z=220.0 [M−H]$^-$.

c) The coupling of [(S)-4-(5-amino-2-fluoro-phenyl)-4-methyl-5,6-dihydro-4H-[1,3]oxazin-2-yl]-carbamic acid tent-butyl ester and 3-(2,2,2-trifluoro-ethoxy)-pyridine-2-carboxylic acid yielded the title compound as a white powder. MS (ESI): m/z=427.1 [M+H]$^+$.

Example 61

5-Difluoromethoxy-pyridine-2-carboxylic acid [3-((S)-2-amino-4-methyl-5,6-dihydro-4H-[1,3]oxazin-4-yl)-4-fluoro-phenyl]-amide

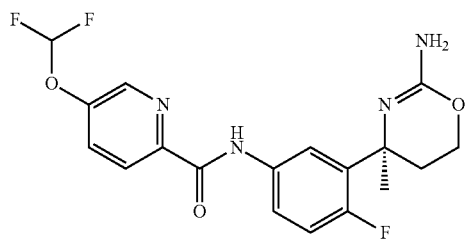

The coupling of (S)-4-(5-Amino-2-fluoro-phenyl)-4-methyl-5,6-dihydro-4H-[1,3]oxazin-2-ylamine and 5-difluoromethoxy-pyridine-2-carboxylic acid yielded the title compound as colorless solid. MS (ESI): m/z=395.0 [M+H]$^+$.

Example 62

3-Methyl-oxetane-3-carboxylic acid [3-((S)-2-amino-4-methyl-5,6-dihydro-4H-[1,3]oxazin-4-yl)-4-fluoro-phenyl]-amide

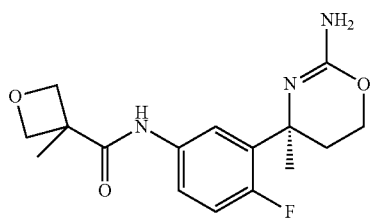

The coupling of (S)-4-(5-Amino-2-fluoro-phenyl)-4-methyl-5,6-dihydro-4H-[1,3]oxazin-2-ylamine and 3-methyl-oxetane-3-carboxylic acid yielded the title compound as colorless solid.
MS (ESI): m/z=322.0 [M+H]$^+$.

Example 63

4-Methyl-isoxazole-3-carboxylic acid [3-(S)-2-amino-4-methyl-5,6-dihydro-4H-[1,3]oxazin-4-yl)-4-fluoro-phenyl]-amide

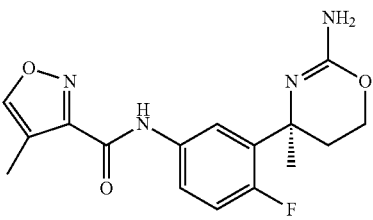

The coupling of (S)-4-(5-Amino-2-fluoro-phenyl)-4-methyl-5,6-dihydro-4H-[1,3]oxazin-2-ylamine and 4-methyl-isoxazole-3-carboxylic acid yielded the title compound as colorless solid. MS (ESI): m/z=333.3 [M+H]⁺.

Example 64

4-Chloro-1H-pyrazole-3-carboxylic acid [3-(S)-2-amino-4-methyl-5,6-dihydro-4H-[1,3]oxazin-4-yl)-4-fluoro-phenyl]-amide

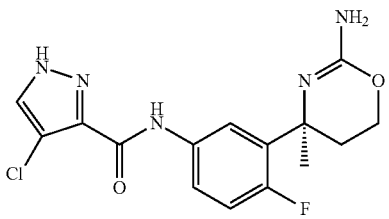

The coupling of (S)-4-(5-Amino-2-fluoro-phenyl)-4-methyl-5,6-dihydro-4H-[1,3]oxazin-2-ylamine and 4-chloro-1H-pyrazole-3-carboxylic acid yielded the title compound as colorless solid. MS (ESI): m/z=352.0 [M+H]⁺.

Example 65

5-Chloro-pyridine-2-carboxylic acid [3-((4aS,7aS)-2-amino-4a,5-dihydro-4H-furo[3,4-d][1,3]oxazin-7a-yl)-4-fluoro-phenyl]-amide

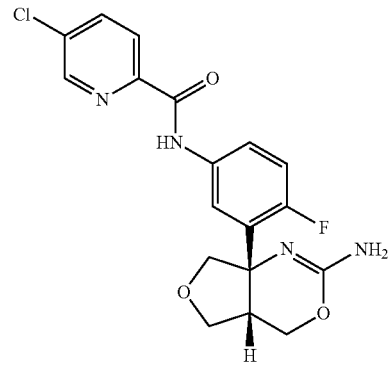

Synthesis of the Intermediate K

To a solution of rac-(4S,4aS)-7a-(2-fluoro-phenyl)-4a,5,7,7a-tetrahydro-4H-furo[3,4-d][1,3]oxazin-2-ylamine (1.7 mmole, intermediate J, preparation described in WO 2009091016) in THF (20 ml) was added subsequently sodium acetate (1.9 mmole) and cyanogen bromide (1.9 mmole) and the reaction mixture was heated at 80° C. for 8 h. The reaction mixture was quenched with water (20 ml), the aqueous layer was extracted with EtOAc, the organic layer was washed with brine, dried over Na2SO4, filtered and the filtrate was evaporated. The residue was purified by chromatography on silica using dichloromethane/methanol (99:1) to give rac-(4S,4aS)-7a-(2-fluoro-phenyl)-4a,5,7,7a-tetrahydro-4H-furo[3,4-d][1,3]oxazin-2-ylamine (56 mg) as a colorless gum.

Synthesis of Intermediate Ea

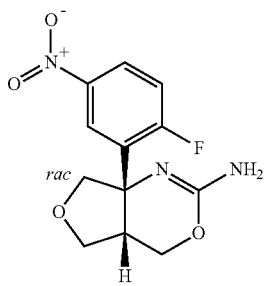

To a solution of rac-(4S,4aS)-7a-(2-fluoro-phenyl)-4a,5,7,7a-tetrahydro-4H-furo[3,4-d][1,3]oxazin-2-ylamine (0.21 mmol) in sulfuric acid (98%, 1 ml) was added at 0° C. fuming nitric acid (0.014 ml) and the reaction mixture was allowed to warm to 25° C. over 30 min. The mixture was slowly added to 5 ml ice cold water, the pH was adjusted to 7 using aqueous 2N NaOH and extracted with dichloromethane. The organic layer was washed with brine, dried over Na2SO4, filtered and the filtrate was evaporated to give crude rac-(4S,4aS)-7a-(2-fluoro-5-nitro-phenyl)-4a,5,7,7a-tetrahydro-4H-furo[3,4-d][1,3]oxazin-2-ylamine (50 mg) as a light yellow foam.

Synthesis of intermediate Fa

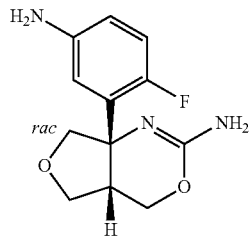

To a solution of rac-(4S,4aS)-7a-(2-fluoro-5-nitro-phenyl)-4a,5,7,7a-tetrahydro-4H-furo[3,4-d][1,3]oxazin-2-ylamine (0.18 mmol) in methanol (5 ml) and triethylamine (0.25 ml) was added Pd/C (10%, 189 mg) and the mixture was hydrogenated at atmospheric pressure for 1 h. The mixture was filtered over dicalite, the filtrate evaporated and the residue purified by chromatography on silica using a gradient of dichloromethane/methanol to yield pure rac-(4S,4aS)-7a-(5-mino-2-fluoro-phenyl)-4a,5,7,7a-tetrahydro-4H-furo[3,4-d][1,3]oxazin-2-ylamine (12 mg) as a colorless waxy solid. MS (ESI): m/z=252.2 [M+H]$^+$.

To a solution of 5-chloro-pyridine-2-carboxylic acid (0.048 mmole) in MeOH (0.3 ml) was added at 0° C. 4-(4,6-dimethoxy-1,3,5-triazin-2-yl)-4-methyl-morpholinium chloride (DMTMM, 0.062 mmole), the reaction mixture was stirred at 0° C. for 5 min. followed by the addition of a solution of rac-(4S,4aS)-7a-(5-amino-2-fluoro-phenyl)-4a,5,7,7a-tetrahydro-4H-furo[3,4-d][1,3]oxazin-2-ylamine (0.048 mmole) in MeOH (0.4 ml) at 0° C. and stirring was continued at this temperature for 4 h. The reaction mixture was evaporated, the residue partitioned between aqueous NaOH (1N, 0.3 ml) and EtOAc, the organic layers was dried over Na2SO4, filtered and the filtrate was evaporated. The residue was triturated with diethyl ether and dried to give the pure title compound (10 mg) as a white solid. MS (ESI): m/z=391.1 [M+H]$^+$.

Example 66

The following test was carried out in order to determine the activity of the compounds of the present invention.

Assay for BACE Inhibition by Measuring Cellular TMEM27 Cleavage

The assay uses the principle of inhibition of human TMEM27 cleavage by endogenous cellular BACE2 in the Ins1e rat cell line and shedding from the cell surface into the culture medium, followed by detection in an ELISA assay. Inhibition of BACE2 prevents the cleavage and shedding in a dose-dependent manner.

The stable cell line "INS-TMEM27" represents an INS1e-derived cell line with inducible expression (using the TetOn system) of full-length hTMEM27 in a doxycycline-dependent manner. The cells were cultured throughout the experiment in RPMI1640+Glutamax (Invitrogen) Penicillin/Streptomycin, 10% Fetal bovine serum, 100 mM pyruvate, 5 mM beta-mercaptoethanol, 100 micrograms/ml G418 and 100 microgram/ml hygromycin and were grown in adherent culture at 37° C. in a standard $CO_2$ cell culture incubator.

INS-TMEM27 cells were seeded in 96-well plates. After 2 days in culture, BACE2 inhibitor was added in a range of concentrations as required by the assay and after a further two hours, doxycycline was added to a final concentration of 500 ng/ml. The cells were incubated for a further 46 hours and the supernatant harvested for detection of shed TMEM27.

An ELISA assay (using a pair of mouse anti-human-TMEM27 antibodies, raised against the extracellular domain of TMEM27) was used for detection of TMEM27 in the culture medium. An $IC_{50}$ for BACE2 inhibition was calculated using the ELISA readout for each inhibitor concentration with standard curve-fitting software XLfit (IDBS) for the Excel spreadsheet program.

The particular compounds according to formula I have an inhibitory activity in the above assay ($IC_{50}$) particularly of 5 nM to 50 µM, more particularly of 5 nM to 1 µM.

For example, the following compounds showed the following $IC_{50}$ (BACE2) values in the assay described above:

TABLE 1

IC$_{50}$ values of selected examples

| Ex. | $IC_{50}$ [nM] |
|---|---|
| 1 | 4 |
| 2 | 10 |
| 3 | 6 |
| 4 | 230 |
| 5 | 89 |
| 6 | 19 |
| 7 | 340 |
| 8 | 19 |
| 9 | 143 |
| 10 | 915 |
| 11 | 28 |
| 12 | 34 |
| 13 | 52 |
| 14 | 190 |
| 15 | 4.5 |
| 16 | 22 |
| 17 | 11 |
| 18 | 35 |
| 19 | 8 |
| 20 | 48 |
| 21 | 240 |

TABLE 1-continued

IC$_{50}$ values of selected examples

| Ex. | IC$_{50}$ [nM] |
|---|---|
| 22 | 7 |
| 23 | 9 |
| 24 | 1 |
| 25 | 5 |
| 26 | 1 |
| 27 | 23 |
| 28 | 4 |
| 29 | 3 |
| 30 | 12 |
| 31 | 11 |
| 32 | 4 |
| 33 | 7 |
| 34 | 350 |
| 35 | 11 |
| 36 | 16 |
| 37 | 40 |
| 38 | 5.1 |
| 39 | 91 |
| 40 | 39 |
| 41 | 52 |
| 42 | 210 |
| 43 | 18 |
| 44 | 7.1 |
| 45 | 400 |
| 46 | 70 |
| 47 | 620 |
| 48 | 36 |
| 49 | 14 |
| 50 | 190 |
| 51 | 73 |
| 52 | 16 |
| 53 | 6 |
| 54 | 810 |
| 55 | 2100 |
| 56 | 6 |
| 57 | 6410 |
| 58 | 700 |
| 59 | 830 |
| 60 | 143 |
| 61 | 474 |
| 62 | 9130 |
| 63 | 104 |
| 64 | 464 |
| 65 | 60 |

Example 67

Film coated tablets containing the following ingredients can be manufactured in a conventional manner:

| Ingredients | Per tablet | |
|---|---|---|
| Kernel: | | |
| Compound of formula I | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxyde (yellow) | 0.8 mg | 1.6 mg |
| Titan dioxide | 0.8 mg | 1.6 mg |

The active ingredient is sieved and mixed with microcrystalline cellulose and the mixture is granulated with a solution of polyvinylpyrrolidone in water. The granulate is mixed with sodium starch glycolate and magnesiumstearate and compressed to yield kernels of 120 or 350 mg respectively. The kernels are lacquered with an aqueous solution/suspension of the above mentioned film coat.

Example 68

Capsules containing the following ingredients can be manufactured in a conventional manner:

| Ingredients | Per capsule |
|---|---|
| Compound of formula I | 25.0 mg |
| Lactose | 150.0 mg |
| Maize starch | 20.0 mg |
| Talc | 5.0 mg |

The components are sieved and mixed and filled into capsules of size 2.

Example 69

Injection solutions can have the following composition:

| | |
|---|---|
| Compound of formula I | 3.0 mg |
| Polyethylene Glycol 400 | 150.0 mg |
| Acetic Acid | q.s. ad pH 5.0 |
| Water for injection solutions | ad 1.0 ml |

The active ingredient is dissolved in a mixture of Polyethylene Glycol 400 and water for injection (part). The pH is adjusted to 5.0 by Acetic Acid. The volume is adjusted to 1.0 ml by addition of the residual amount of water. The solution is filtered, filled into vials using an appropriate overage and sterilized.

Example 70

Soft gelatin capsules containing the following ingredients can be manufactured in a conventional manner:

| Capsule contents | |
|---|---|
| Compound of formula I | 5.0 mg |
| Yellow wax | 8.0 mg |
| Hydrogenated Soya bean oil | 8.0 mg |
| Partially hydrogenated plant oils | 34.0 mg |
| Soya bean oil | 110.0 mg |
| Weight of capsule contents | 165.0 mg |
| Gelatin capsule | |
| Gelatin | 75.0 mg |
| Glycerol 85 % | 32.0 mg |
| Karion 83 | 8.0 mg (dry matter) |
| Titan dioxide | 0.4 mg |
| Iron oxide yellow | 1.1 mg |

The active ingredient is dissolved in a warm melting of the other ingredients and the mixture is filled into soft gelatin capsules of appropriate size. The filled soft gelatin capsules are treated according to the usual procedures.

Example 71

Sachets containing the following ingredients can be manufactured in a conventional manner:

| | |
|---|---|
| Compound of formula I | 50.0 mg |
| Lactose, fine powder | 1015.0 mg |
| Microcristalline cellulose (AVICEL PH 102) | 1400.0 mg |
| Sodium carboxymethyl cellulose | 14.0 mg |
| Polyvinylpyrrolidone K 30 | 10.0 mg |
| Magnesiumstearate | 10.0 mg |
| Flavoring additives | 1.0 mg |

The active ingredient is mixed with lactose, microcristalline cellulose and sodium carboxymethyl cellulose and granulated with a mixture of polyvinylpyrrolidone in water. The granulate is mixed with magnesium stearate and the flavouring additives and filled into sachets.

The invention claimed is:
1. A compound of formula I,

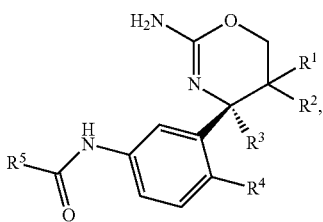

I wherein
$R^1$ is hydrogen or $C_{1-7}$-alkyl;
$R^2$ is hydrogen or $C_{1-7}$-alkyl;
 or $R^1$ and $R^2$ together with the C atom they are attached to form a $C_{3-7}$-cycloalkyl ring;
$R^3$ is $C_{1-7}$-alkyl or $C_{3-7}$-cycloalkyl;
 or $R^2$ and $R^3$ together with the C atoms they are attached to form a $C_{3-7}$-cycloalkyl or a 3- to 7-membered O-heterocyclyl ring;
$R^4$ is selected from the group consisting of hydrogen, $C_{1-7}$-alkyl, halogen, cyano and $C_{1-7}$-alkoxy; and
$R^5$ is selected from the group consisting of:
 i) aryl, unsubstituted or substituted by one, two or three groups selected from the group consisting of $C_{1-7}$-alkyl, halogen, halogen-$C_{1-7}$-alkyl, $C_{1-7}$-alkoxy, halogen-$C_{1-7}$-alkoxy, cyano, hydroxy-$C_{1-7}$-alkyl, oxo and phenyl,
 ii) heteroaryl, unsubstituted or substituted by one, two or three groups selected from the group consisting of $C_{1-7}$-alkyl, halogen, halogen-$C_{1-7}$-alkyl, $C_{1-7}$-alkoxy, halogen-$C_{1-7}$-alkoxy, cyano, hydroxy-$C_{1-7}$-alkyl, oxo and phenyl,
 iii) $C_{1-7}$-alkyl, unsubstituted or substituted by one, two, three, four or five groups individually selected from the group consisting of halogen, halogen-$C_{1-7}$-alkyl, $C_{1-7}$-alkoxy, halogen-$C_{1-7}$-alkoxy, cyano and hydroxy-$C_{1-7}$-alkyl,
 iv) a $C_{3-7}$-cycloalkyl ring, unsubstituted or substituted by one, two or three groups selected from the group consisting of $C_{1-7}$-alkyl, halogen, halogen-$C_{1-7}$-alkyl, $C_{1-7}$-alkoxy, halogen-$C_{1-7}$-alkoxy, cyano and hydroxy-$C_{1-7}$-alkyl, and
 v) 3- to 7-membered O-heterocyclyl ring, unsubstituted or substituted by one, two or three groups selected from the group consisting of $C_{1-7}$-alkyl, halogen, halogen-$C_{1-7}$-alkyl, $C_{1-7}$-alkoxy, halogen-$C_{1-7}$-alkoxy, cyano and hydroxy-$C_{1-7}$-alkyl,
or a pharmaceutically acceptable salt thereof.

2. A compound according to claim 1,

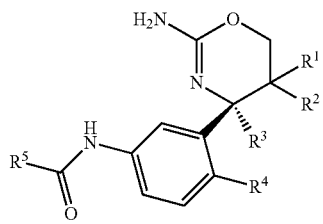

I wherein
$R^1$ is hydrogen or $C_{1-7}$-alkyl;
$R^2$ is hydrogen or $C_{1-7}$-alkyl;
 or $R^1$ and $R^2$ together with the C atom they are attached to form a $C_{3-7}$-cycloalkyl ring;
$R^3$ is $C_{1-7}$-alkyl or $C_{3-7}$-cycloalkyl;
 or $R^2$ and $R^3$ together with the C atoms they are attached to form a $C_{3-7}$-cycloalkyl or a 3- to 7-membered O-heterocyclyl ring;
$R^4$ is selected from the group consisting of hydrogen, $C_{1-7}$-alkyl, halogen, cyano and $C_{1-7}$-alkoxy; and
$R^5$ is aryl or heteroaryl, said aryl or heteroaryl being unsubstituted or substituted by one, two or three groups selected from the group consisting of $C_{1-7}$-alkyl, halogen, halogen-$C_{1-7}$-alkyl, $C_{1-7}$-alkoxy, halogen-$C_{1-7}$-alkoxy, cyano, hydroxy-$C_{1-7}$-alkyl, oxo and phenyl;
or a pharmaceutically acceptable salt thereof.

3. A compound according to claim 1, wherein $R^1$ and $R^2$ together with the C atom they are attached to form a $C_{3-7}$-cycloalkyl ring.

4. A compound according to claim 1, wherein $R^1$ and $R^2$ together with the C atom they are attached to form a cyclopropyl.

5. A compound according to claim 1, wherein $R^1$ and $R^2$ are each hydrogen.

6. A compound according to claim 1, wherein $R^3$ is $C_{1-7}$-alkyl.

7. A compound according to claim 1, wherein $R^3$ is methyl.

8. A compound according to claim 1, wherein $R^3$ is ethyl.

9. A compound according to claim 1, wherein $R^4$ is halogen.

10. A compound according to claim 1, wherein $R^4$ is fluoro.

11. A compound according to claim 1, wherein $R^5$ is heteroaryl, said heteroaryl being unsubstituted or substituted by one, two or three groups selected from the group consisting of $C_{1-7}$-alkyl, halogen, halogen-$C_{1-7}$-alkyl, $C_{1-7}$-alkoxy, halogen-$C_{1-7}$-alkoxy, cyano, hydroxy-$C_{1-7}$-alkyl, oxo and phenyl.

12. A compound according to claim 1, wherein $R^5$ is heteroaryl selected from the group consisting of pyridyl, pyrazinyl, pyrimidinyl, pyridazinyl, 6-oxo-1,6-dihydropyridazinyl, 5-oxo-4,5-dihydropyrazinyl, pyrrolyl, furyl, thienyl, oxazolyl, isoxazolyl, oxadiazolyl, thiadiazolyl, tetrazolyl, pyrazolyl, imidazolyl, triazolyl, thiazolyl, quinolinyl, isoquinolinyl, cinnolinyl, pyrazolo[1,5-a]pyridyl, imidazo[1,2-a]pyridyl, thieno[2,3-c]pyridyl, quinoxalinyl, benzo[b]thienyl, benzothiazolyl, benzotriazolyl, indolyl, indazolyl and 3,4-dihydro-1H-isoquinolinyl, said heteroaryl being unsubstituted or substituted by one, two or three groups selected from the group consisting of $C_{1-7}$-alkyl, halogen, halogen-$C_{1-7}$-alkyl, $C_{1-7}$-alkoxy, halogen-$C_{1-7}$-alkoxy, cyano, hydroxy-$C_{1-7}$-alkyl, oxo and phenyl.

13. A compound according to claim 1, wherein $R^5$ is heteroaryl selected from the group consisting of thienyl, oxazolyl, isoxazolyl, pyrazolyl, pyridyl, pyrimidinyl, pyrazinyl, 6-oxo-1,6-dihydropyridazinyl, 5-oxo-4,5-dihydropyrazinyl and imidazo[1,2-a]pyridyl, said heteroaryl being unsubstituted or substituted by one, two or three groups selected from the group consisting of $C_{1-7}$-alkyl, halogen, halogen-$C_{1-7}$-alkyl, $C_{1-7}$-alkoxy, halogen-$C_{1-7}$-alkoxy, cyano, hydroxy-$C_{1-7}$-alkyl, oxo and phenyl.

14. A compound according to claim 1, wherein $R^5$ is heteroaryl selected from the group consisting of thienyl, oxazolyl, pyridyl, pyrimidinyl and pyrazinyl, said heteroaryl being unsubstituted or substituted by one, two or three groups selected from the group consisting of $C_{1-7}$-alkyl, halogen, halogen-$C_{1-7}$-alkyl, $C_{1-7}$-alkoxy, halogen-$C_{1-7}$-alkoxy, cyano, hydroxy-$C_{1-7}$-alkyl, oxo and phenyl.

15. A compound according to claim 1, wherein $R^5$ is heteroaryl selected from the group consisting of thienyl, oxazolyl, pyridyl, pyrimidinyl and pyrazinyl substituted by one, two or three groups selected from the group consisting of $C_{1-7}$-alkyl, halogen, halogen-$C_{1-7}$-alkyl, $C_{1-7}$-alkoxy, halogen-$C_{1-7}$-alkoxy, cyano, hydroxy-$C_{1-7}$-alkyl, oxo and phenyl.

16. A compound according to claim 1, wherein $R^5$ is heteroaryl selected from the group consisting of 1H-pyrazolyl, benzo[b]thiophenyl, isoxazolyl, oxazolyl, pyrazinyl, pyridinyl, pyrimidinyl, thiazolyl, thieno[2,3-c]pyridinyl and thiophenyl, said heteroaryl being unsubstituted or substituted by one or two groups selected from the group consisting of $C_{1-7}$-alkyl, halogen, halogen-$C_{1-7}$-alkoxy, halogen-$C_{1-7}$-alkyl, $C_{1-7}$-alkoxy, cyano and phenyl.

17. A compound according to claim 1, wherein $R^5$ is heteroaryl selected from the group consisting of 1H-pyrazolyl, thiazolyl, oxazolyl, pyridinyl, substituted by one or two substituents selected from the group consisting of $C_{1-7}$-alkyl, halogen and cyano.

18. A compound according to claim 1, wherein $R^5$ is heteroaryl selected from the group consisting of 1H-pyrazole-3-yl, benzo[b]thiophene-2-yl, isoxazole-3-yl, oxazole-4-yl, pyrazine-2-yl, pyridine-2-yl, pyrimidine-2-yl, thiazol-4-yl, thieno[2,3-c]pyridine-7-yl and thiophene-2-yl, said heteroaryl being unsubstituted or substituted by one or two groups selected from the group consisting of methyl, fluoro, chloro, difluoromethoxy, trifluoroethoxy, trifluoromethyl, methoxy, cyano and phenyl.

19. A compound according to claim 1, wherein $R^5$ is phenyl, said phenyl being unsubstituted or substituted by one, two or three groups selected from the group consisting of $C_{1-7}$-alkyl, halogen, halogen-$C_{1-7}$-alkyl, $C_{1-7}$-alkoxy, halogen-$C_{1-7}$-alkoxy, cyano, hydroxy-$C_{1-7}$-alkyl, oxo and phenyl.

20. A compound according to claim 1, wherein $R^5$ is phenyl, substituted by one or two halogens.

21. A compound according to claim 1, wherein $R^5$ is $C_{1-7}$-alkyl, unsubstituted or substituted by one, two, three, four or five halogens.

22. A compound according to claim 1, wherein $R^5$ is ethyl, substituted by one, two, three, four or five fluoros.

23. A compound according to claim 1, wherein $R^5$ is $C_{3-7}$-cycloalkyl ring, unsubstituted or substituted by one, two or three groups selected from the group consisting of halogen and halogen-$C_{1-7}$-alkyl.

24. A compound according to claim 1, wherein $R^5$ is cyclopropyl, by one or two groups selected from the group consisting of fluoro and trifluoromethyl.

25. A compound according to claim 1, wherein $R^5$ is 3- to 7-membered O-heterocyclyl ring, unsubstituted or substituted by one, two or three groups selected from the group consisting of $C_{1-7}$-alkyl, halogen, halogen-$C_{1-7}$-alkyl, $C_{1-7}$-alkoxy, halogen-$C_{1-7}$-alkoxy, cyano and hydroxy-$C_{1-7}$-alkyl.

26. A compound according to claim 1, wherein $R^5$ is oxetanyl, substituted by methyl.

27. A compound according to claim 1, selected from the group consisting of 3,5-Dichloro-pyridine-2-carboxylic acid [3-((S)-2-amino-4-methyl-5,6-dihydro-4H-[1,3]oxazin-4-yl)-4-fluoro-phenyl]-amide, 5-Chloro-pyridine-2-carboxylic acid [3-((S)-2-amino-4-methyl-5,6-dihydro-4H-[1,3]oxazin-4-yl)-4-fluoro-phenyl]-amide, 5-Fluoro-pyridine-2-carboxylic acid [3-((S)-2-amino-4-methyl-5,6-dihydro-4H-[1,3]oxazin-4-yl)-4-fluoro-phenyl]-amide, Pyridine-2-carboxylic acid [3-((S)-2-amino-4-methyl-5,6-dihydro-4H-[1,3]oxazin-4-yl)-4-fluoro-phenyl]-amide, 5-Trifluoromethyl-pyridine-2-carboxylic acid [3-((S)-2-amino-4-methyl-5,6-dihydro-4H-[1,3]oxazin-4-yl)-4-fluoro-phenyl]-amide, 3-Fluoro-pyridine-2-carboxylic acid [3-((S)-2-amino-4-methyl-5,6-dihydro-4H-[1,3]oxazin-4-yl)-4-fluoro-phenyl]-amide, 5-Fluoro-thiophene-2-carboxylic acid [3-((S)-2-amino-4-methyl-5,6-dihydro-4H-[1,3]oxazin-4-yl)-4-fluoro-phenyl]-amide, 2-Methyl-oxazole-4-carboxylic acid [3-((S)-2-amino-4-methyl-5,6-dihydro-4H-[1,3]oxazin-4-yl)-4-fluoro-phenyl]-amide, 4-Chloro-pyridine-2-carboxylic acid [3-((S)-2-amino-4-methyl-5,6-dihydro-4H-[1,3]oxazin-4-yl)-4-fluoro-phenyl]-amide, 5-Chloro-thiophene-2-carboxylic acid [3-((S)-2-amino-4-methyl-5,6-dihydro-4H-[1,3]oxazin-4-yl)-4-fluoro-phenyl]-amide, Thieno[2,3-c]pyridine-7-carboxylic acid [3-((S)-2-amino-4-methyl-5,6-dihydro-4H-[1,3]oxazin-4-yl)-4-fluoro-phenyl]-amide, 3-Phenyl-pyridine-2-carboxylic acid [3-((S)-2-amino-4-methyl-5,6-dihydro-4H-[1,3]oxazin-4-yl)-4-fluoro-phenyl]-amide, Benzo[b]thiophene-2-carboxylic acid [3-((S)-2-amino-4-methyl-5,6-dihydro-4H-[1,3]oxazin-4-yl)-4-fluoro-phenyl]-amide, 5-Chloro-pyrazine-2-carboxylic acid [3-((S)-2-amino-4-methyl-5,6-dihydro-4H-[1,3]oxazin-4-yl)-4-fluoro-phenyl]-amide, 5-Methyl-pyridine-2-carboxylic acid [3-((S)-2-amino-4-methyl-5,6-dihydro-4H-[1,3]oxazin-4-yl)-4-fluoro-phenyl]-amide, 3-Trifluoromethyl-pyridine-2-carboxylic acid [3-((S)-2-amino-4-methyl-5,6-dihydro-4H-[1,3]oxazin-4-yl)-4-fluoro-phenyl]-amide, 5-Methyl-thiophene-2-carboxylic acid [3-((S)-2-amino-4-methyl-5,6-dihydro-4H-[1,3]oxazin-4-yl)-4-fluoro-phenyl]-amide, Pyridine-2-carboxylic acid [3-((S)-2-amino-4-ethyl-5,6-dihydro-4H-[1,3]oxazin-4-yl)-4-fluoro-phenyl]-amide, 5-Chloro-pyridine-2-carboxylic acid [3-((S)-2-amino-4-ethyl-5,6-dihydro-4H-[1,3]oxazin-4-yl)-4-fluoro-phenyl]-amide, 5-Methyl-thiophene-2-carboxylic acid [3-((S)-2-amino-4-ethyl-5,6-dihydro-4H-[1,3]oxazin-4-yl)-4-fluoro-phenyl]-amide, 5-Chloro-thiophene-2-carboxylic acid [3-((S)-2-amino-4-ethyl-5,6-dihydro-4H-[1,3]oxazin-4-yl)-4-fluoro-phenyl]-amide,
3,5-Dichloro-pyridine-2-carboxylic acid [3-((S)-2-amino-4-ethyl-5,6-dihydro-4H-[1,3]oxazin-4-yl)-4-fluoro-phenyl]-amide,
5-Chloro-3-methyl-pyridine-2-carboxylic acid [3-((S)-2-amino-4-ethyl-5,6-dihydro-4H-[1,3]oxazin-4-yl)-4-fluoro-phenyl]-amide,
2-Methyl-oxazole-4-carboxylic acid [3-((S)-2-amino-4-ethyl-5,6-dihydro-4H-[1,3]oxazin-4-yl)-4-fluoro-phenyl]-amide,
5-Cyano-pyridine-2-carboxylic acid [3-((S)-2-amino-4-methyl-5,6-dihydro-4H-[1,3]oxazin-4-yl)-4-fluoro-phenyl]-amide,
5-Chloro-3-methyl-pyridine-2-carboxylic acid [3-((S)-2-amino-4-methyl-5,6-dihydro-4H-[1,3]oxazin-4-yl)-4-fluoro-phenyl]-amide,
3-Methoxy-pyridine-2-carboxylic acid [3-((S)-2-amino-4-methyl-5,6-dihydro-4H-[1,3]oxazin-4-yl)-4-fluoro-phenyl]-amide,
2-Methyl-thiazole-4-carboxylic acid [3-((S)-2-amino-4-methyl-5,6-dihydro-4H-[1,3]oxazin-4-yl)-4-fluoro-phenyl]-amide,
1-Methyl-1H-pyrazole-3-carboxylic acid [3-((S)-2-amino-4-methyl-5,6-dihydro-4H-[1,3]oxazin-4-yl)-4-fluoro-phenyl]-amide,
5-Methoxy-pyridine-2-carboxylic acid [3-((S)-2-amino-4-methyl-5,6-dihydro-4H-[1,3]oxazin-4-yl)-4-fluoro-phenyl]-amide,
3-Chloro-5-trifluoromethyl-pyridine-2-carboxylic acid [3-((S)-2-amino-4-methyl-5,6-dihydro-4H-[1,3]oxazin-4-yl)-4-fluoro-phenyl]-amide,
6-Chloro-pyridine-2-carboxylic acid [3-((S)-2-amino-4-methyl-5,6-dihydro-4H-[1,3]oxazin-4-yl)-4-fluoro-phenyl]-amide,
3,5-Difluoro-pyridine-2-carboxylic acid [3-((S)-2-amino-4-methyl-5,6-dihydro-4H-[1,3]oxazin-4-yl)-4-fluoro-phenyl]-amide,
3-Methyl-thiophene-2-carboxylic acid [3-((S)-2-amino-4-methyl-5,6-dihydro-4H-[1,3]oxazin-4-yl)-4-fluoro-phenyl]-amide,
3-Chloro-5-fluoro-pyridine-2-carboxylic acid [3-((S)-2-amino-4-methyl-5,6-dihydro-4H-[1,3]oxazin-4-yl)-4-fluoro-phenyl]-amide,
5-Chloro-pyridine-2-carboxylic acid [3-((S)-6-amino-8-methyl-5-oxa-7-aza-spiro[2.5]oct-6-en-8-yl)-4-fluoro-phenyl]-amide,
3-Fluoro-pyridine-2-carboxylic acid [3-((S)-6-amino-8-methyl-5-oxa-7-aza-spiro[2.5]oct-6-en-8-yl)-4-fluoro-phenyl]-amide,
5-Chloro-3-methyl-pyridine-2-carboxylic acid [3-((S)-6-amino-8-methyl-5-oxa-7-aza-spiro[2.5]oct-6-en-8-yl)-4-fluoro-phenyl]-amide,
5-Methoxy-pyridine-2-carboxylic acid [3-((S)-6-amino-8-methyl-5-oxa-7-aza-spiro[2.5]oct-6-en-8-yl)-4-fluoro-phenyl]-amide,
5-Fluoro-pyridine-2-carboxylic acid [3-((S)-6-amino-8-methyl-5-oxa-7-aza-spiro[2.5]oct-6-en-8-yl)-4-fluoro-phenyl]-amide,
5-Cyano-pyridine-2-carboxylic acid [3-((S)-6-amino-8-methyl-5-oxa-7-aza-spiro[2.5]oct-6-en-8-yl)-4-fluoro-phenyl]-amide,
5-Difluoromethoxy-pyridine-2-carboxylic acid [3-((S)-6-amino-8-methyl-5-oxa-7-aza-spiro[2.5]oct-6-en-8-yl)-4-fluoro-phenyl]-amide,
Pyridine-2-carboxylic acid [3-((S)-6-amino-8-methyl-5-oxa-7-aza-spiro[2.5]oct-6-en-8-yl)-4-fluoro-phenyl]-amide,
5-Chloro-pyrimidine-2-carboxylic acid [3-((S)-6-amino-8-methyl-5-oxa-7-aza-spiro[2.5]oct-6-en-8-yl)-4-fluoro-phenyl]-amide,
N-[3-((S)-2-Amino-4-methyl-5,6-dihydro-4H-[1,3]oxazin-4-yl)-4-fluoro-phenyl]-2,3,3,3-tetrafluoro-propionamide,
2,2-Difluoro-cyclopropanecarboxylic acid [3-((S)-2-amino-4-methyl-5,6-dihydro-4H-[1,3]oxazin-4-yl)-4-fluoro-phenyl]-amide,
(S)—N-(3-(6-amino-8-methyl-5-oxa-7-azaspiro[2.5]oct-6-en-8-yl)-4-fluorophenyl)-2,6-difluorobenzamide,
(S)—N-(3-(6-amino-8-methyl-5-oxa-7-azaspiro[2.5]oct-6-en-8-yl)-4-fluorophenyl)-3-chloropicolinamide,
(S)—N-(3-(6-amino-8-methyl-5-oxa-7-azaspiro[2.5]oct-6-en-8-yl)-4-fluorophenyl)-3,5-difluoropicolinamide,
(S)—N-(3-(6-amino-8-methyl-5-oxa-7-azaspiro[2.5]oct-6-en-8-yl)-4-fluorophenyl)-3-chloro-5-(trifluoromethyl)picolinamide,
(S)—N-(3-(6-amino-8-methyl-5-oxa-7-azaspiro[2.5]oct-6-en-8-yl)-4-fluorophenyl)-3-(trifluoromethyl)picolinamide,
(S)—N-(3-(6-amino-8-methyl-5-oxa-7-azaspiro[2.5]oct-6-en-8-yl)-4-fluorophenyl)-3-chloro-5-fluoropicolinamide,
(S)—N-(3-(6-amino-8-methyl-5-oxa-7-azaspiro[2.5]oct-6-en-8-yl)-4-fluorophenyl)-3,5-dichloropicolinamide,
(S)—N-(3-(6-amino-8-methyl-5-oxa-7-azaspiro[2.5]oct-6-en-8-yl)-4-fluorophenyl)-1-(trifluoromethyl)cyclopropanecarboxamide,
N-(3-((S)-6-amino-8-methyl-5-oxa-7-azaspiro[2.5]oct-6-en-8-yl)-4-fluorophenyl)-2,2-difluorocyclopropanecarboxamide,
(S)—N-(3-(6-amino-8-methyl-5-oxa-7-azaspiro[2.5]oct-6-en-8-yl)-4-fluorophenyl)-4-chloro-1-methyl-1H-pyrazole-3-carboxamide,
(S)—N-(3-(6-amino-8-methyl-5-oxa-7-azaspiro[2.5]oct-6-en-8-yl)-4-fluorophenyl)-5-chloro-4-methylisoxazole-3-carboxamide,
1-Trifluoromethyl-cyclopropanecarboxylic acid [3-((S)-2-amino-4-methyl-5,6-dihydro-4H-[1,3]oxazin-4-yl)-4-fluoro-phenyl]-amide,
N-[3-((S)-2-Amino-4-methyl-5,6-dihydro-4H-[1,3]oxazin-4-yl)-4-fluoro-phenyl]-3,3,3-trifluoro-propionamide,
(S)—N-(3-(2-amino-4-methyl-5,6-dihydro-4H-1,3-oxazin-4-yl)-4-fluorophenyl)-3-(2,2,2-trifluoroethoxy)picolinamide,
5-Difluoromethoxy-pyridine-2-carboxylic acid [3-((S)-2-amino-4-methyl-5,6-dihydro-4H-[1,3]oxazin-4-yl)-4-fluoro-phenyl]-amide,
(S)—N-(3-(2-amino-4-methyl-5,6-dihydro-4H-1,3-oxazin-4-yl)-4-fluorophenyl)-3-methyloxetane-3-carboxamide,
(S)—N-(3-(2-amino-4-methyl-5,6-dihydro-4H-1,3-oxazin-4-yl)-4-fluorophenyl)-4-methylisoxazole-3-carboxamide,
4-Chloro-1H-pyrazole-3-carboxylic acid [3-((S)-2-amino-4-methyl-5,6-dihydro-4H-[1,3]oxazin-4-yl)-4-fluoro-phenyl]-amide, and
5-Chloro-pyridine-2-carboxylic acid [3-((4aS,7aS)-2-amino-4a,5-dihydro-4H-furo[3,4-d][1,3]oxazin-7a-yl)-4-fluoro-phenyl]-amide,
or pharmaceutically acceptable salts thereof.

28. A compound according to claim 1, selected from the group consisting of
- 3,5-Dichloro-pyridine-2-carboxylic acid [3-((S)-2-amino-4-ethyl-5,6-dihydro-4H-[1,3]oxazin-4-yl)-4-fluoro-phenyl]-amide,
- 5-Chloro-3-methyl-pyridine-2-carboxylic acid [3-((S)-2-amino-4-ethyl-5,6-dihydro-4H-[1,3]oxazin-4-yl)-4-fluoro-phenyl]-amide,
- 2-Methyl-oxazole-4-carboxylic acid [3-((S)-2-amino-4-ethyl-5,6-dihydro-4H-[1,3]oxazin-4-yl)-4-fluoro-phenyl]-amide,
- 5-Cyano-pyridine-2-carboxylic acid [3-((S)-2-amino-4-methyl-5,6-dihydro-4H-[1,3]oxazin-4-yl)-4-fluoro-phenyl]-amide,
- 5-Chloro-3-methyl-pyridine-2-carboxylic acid [3-((S)-2-amino-4-methyl-5,6-dihydro-4H-[1,3]oxazin-4-yl)-4-fluoro-phenyl]-amide,
- 2-Methyl-thiazole-4-carboxylic acid [3-((S)-2-amino-4-methyl-5,6-dihydro-4H-[1,3]oxazin-4-yl)-4-fluoro-phenyl]-amide,
- 1-Methyl-1H-pyrazole-3-carboxylic acid [3-((S)-2-amino-4-methyl-5,6-dihydro-4H-[1,3]oxazin-4-yl)-4-fluoro-phenyl]-amide,
- 6-Chloro-pyridine-2-carboxylic acid [3-((S)-2-amino-4-methyl-5,6-dihydro-4H-[1,3]oxazin-4-yl)-4-fluoro-phenyl]-amide,
- 3,5-Difluoro-pyridine-2-carboxylic acid [3-((S)-2-amino-4-methyl-5,6-dihydro-4H-[1,3]oxazin-4-yl)-4-fluoro-phenyl]-amide,
- 5-Chloro-3-methyl-pyridine-2-carboxylic acid [3-((S)-6-amino-8-methyl-5-oxa-7-aza-spiro[2.5]oct-6-en-8-yl)-4-fluoro-phenyl]-amide,
- (S)—N-(3-(6-amino-8-methyl-5-oxa-7-azaspiro[2.5]oct-6-en-8-yl)-4-fluorophenyl)-3,5-dichloropicolinamide, and
- (S)—N-(3-(6-amino-8-methyl-5-oxa-7-azaspiro[2.5]oct-6-en-8-yl)-4-fluorophenyl)-4-chloro-1-methyl-1H-pyrazole-3-carboxamide, or pharmaceutically acceptable salts thereof.

29. A compound according to claim 1, selected from the group consisting of
- 3,5-dichloro-pyridine-2-carboxylic acid [3-((S)-2-amino-4-methyl-5,6-dihydro-4H-[1,3]oxazin-4-yl)-4-fluoro-phenyl]-amide,
- 5-chloro-pyridine-2-carboxylic acid [3-((S)-2-amino-4-methyl-5,6-dihydro-4H-[1,3]oxazin-4-yl)-4-fluoro-phenyl]-amide,
- 5-fluoro-pyridine-2-carboxylic acid [3-((S)-2-amino-4-methyl-5,6-dihydro-4H-[1,3]oxazin-4-yl)-4-fluoro-phenyl]-amide,
- pyridine-2-carboxylic acid [3-((S)-2-amino-4-methyl-5,6-dihydro-4H-[1,3]oxazin-4-yl)-4-fluoro-phenyl]-amide,
- 5-trifluoromethyl-pyridine-2-carboxylic acid [3-((S)-2-amino-4-methyl-5,6-dihydro-4H-[1,3]oxazin-4-yl)-4-fluoro-phenyl]-amide,
- 3-fluoro-pyridine-2-carboxylic acid [3-((S)-2-amino-4-methyl-5,6-dihydro-4H-[1,3]oxazin-4-yl)-4-fluoro-phenyl]-amide,
- 5-fluoro-thiophene-2-carboxylic acid [3-((S)-2-amino-4-methyl-5,6-dihydro-4H-[1,3]oxazin-4-yl)-4-fluoro-phenyl]-amide,
- 2-methyl-oxazole-4-carboxylic acid [3-((S)-2-amino-4-methyl-5,6-dihydro-4H-[1,3]oxazin-4-yl)-4-fluoro-phenyl]-amide,
- 4-chloro-pyridine-2-carboxylic acid [3-((S)-2-amino-4-methyl-5,6-dihydro-4H-[1,3]oxazin-4-yl)-4-fluoro-phenyl]-amide,
- 5-chloro-thiophene-2-carboxylic acid [3-((S)-2-amino-4-methyl-5,6-dihydro-4H-[1,3]oxazin-4-yl)-4-fluoro-phenyl]-amide,
- thieno[2,3-c]pyridine-7-carboxylic acid [3-((S)-2-amino-4-methyl-5,6-dihydro-4H-[1,3]oxazin-4-yl)-4-fluoro-phenyl]-amide,
- 3-phenyl-pyridine-2-carboxylic acid [3-((S)-2-amino-4-methyl-5,6-dihydro-4H-[1,3]oxazin-4-yl)-4-fluoro-phenyl]-amide,
- benzo[b]thiophene-2-carboxylic acid [3-((S)-2-amino-4-methyl-5,6-dihydro-4H-[1,3]oxazin-4-yl)-4-fluoro-phenyl]-amide,
- 5-chloro-pyrazine-2-carboxylic acid [3-((S)-2-amino-4-methyl-5,6-dihydro-4H-[1,3]oxazin-4-yl)-4-fluoro-phenyl]-amide,
- 5-methyl-pyridine-2-carboxylic acid [3-((S)-2-amino-4-methyl-5,6-dihydro-4H-[1,3]oxazin-4-yl)-4-fluoro-phenyl]-amide,
- 3-trifluoromethyl-pyridine-2-carboxylic acid [3-((S)-2-amino-4-methyl-5,6-dihydro-4H-[1,3]oxazin-4-yl)-4-fluoro-phenyl]-amide,
- 5-methyl-thiophene-2-carboxylic acid [3-((S)-2-amino-4-methyl-5,6-dihydro-4H-[1,3]oxazin-4-yl)-4-fluoro-phenyl]-amide,
- pyridine-2-carboxylic acid [3-((S)-2-amino-4-ethyl-5,6-dihydro-4H-[1,3]oxazin-4-yl)-4-fluoro-phenyl]-amide,
- 5-chloro-pyridine-2-carboxylic acid [3-((S)-2-amino-4-ethyl-5,6-dihydro-4H-[1,3]oxazin-4-yl)-4-fluoro-phenyl]-amide,
- 5-methyl-thiophene-2-carboxylic acid [3-((S)-2-amino-4-ethyl-5,6-dihydro-4H-[1,3]oxazin-4-yl)-4-fluoro-phenyl]-amide,
- 5-chloro-thiophene-2-carboxylic acid [3-((S)-2-amino-4-ethyl-5,6-dihydro-4H-[1,3]oxazin-4-yl)-4-fluoro-phenyl]-amide,
- 3,5-dichloro-pyridine-2-carboxylic acid [3-((S)-2-amino-4-ethyl-5,6-dihydro-4H-[1,3]oxazin-4-yl)-4-fluoro-phenyl]-amide,
- 5-chloro-3-methyl-pyridine-2-carboxylic acid [3-((S)-2-amino-4-ethyl-5,6-dihydro-4H-[1,3]oxazin-4-yl)-4-fluoro-phenyl]-amide,
- 2-methyl-oxazole-4-carboxylic acid [3-((S)-2-amino-4-ethyl-5,6-dihydro-4H-[1,3]oxazin-4-yl)-4-fluoro-phenyl]-amide,
- 5-cyano-pyridine-2-carboxylic acid [3-((S)-2-amino-4-methyl-5,6-dihydro-4H-[1,3]oxazin-4-yl)-4-fluoro-phenyl]-amide,
- 5-chloro-3-methyl-pyridine-2-carboxylic acid [3-((S)-2-amino-4-methyl-5,6-dihydro-4H-[1,3]oxazin-4-yl)-4-fluoro-phenyl]-amide,
- 3-methoxy-pyridine-2-carboxylic acid [3-((S)-2-amino-4-methyl-5,6-dihydro-4H-[1,3]oxazin-4-yl)-4-fluoro-phenyl]-amide,
- 2-methyl-thiazole-4-carboxylic acid [3-((S)-2-amino-4-methyl-5,6-dihydro-4H-[1,3]oxazin-4-yl)-4-fluoro-phenyl]-amide,
- 1-methyl-1H-pyrazole-3-carboxylic acid [3-((S)-2-amino-4-methyl-5,6-dihydro-4H-[1,3]oxazin-4-yl)-4-fluoro-phenyl]-amide,
- 5-methoxy-pyridine-2-carboxylic acid [3-((S)-2-amino-4-methyl-5,6-dihydro-4H-[1,3]oxazin-4-yl)-4-fluoro-phenyl]-amide,
- 3-chloro-5-trifluoromethyl-pyridine-2-carboxylic acid [3-((S)-2-amino-4-methyl-5,6-dihydro-4H-[1,3]oxazin-4-yl)-4-fluoro-phenyl]-amide, 6-chloro-pyridine-2-carboxylic acid [3-((S)-2-amino-4-methyl-5,6-dihydro-4H-[1,3]oxazin-4-yl)-4-fluoro-phenyl]-amide, 3,5-difluoro-pyridine-2-carboxylic acid [3-((S)-2-amino-4-methyl-5,6-dihydro-4H-[1,3]oxazin-4-yl)-4-fluoro-phenyl]-amide, 3-methyl-thiophene-2-carboxylic acid [3-((S)-2-amino-4-methyl-5,6-dihydro-4H-[1,3]oxazin-4-yl)-4-fluoro-phenyl]-amide, and 3-chloro-5-fluoro-pyridine-2-carboxylic acid [3-((S)-2-amino-4-methyl-5,6-dihydro-4H-[1,3]oxazin-4-yl)-4-fluoro-phenyl]-amide, or pharmaceutically acceptable salts thereof.

30. A pharmaceutical composition comprising a compound according to claim 1 and a pharmaceutically acceptable carrier and/or adjuvant.

\* \* \* \* \*